(12) United States Patent
Taghizadeh

(10) Patent No.: US 10,420,802 B2
(45) Date of Patent: Sep. 24, 2019

(54) TOPICAL FORMULATION FOR SKIN CARE

(71) Applicant: Aesthetics Biomedical, Inc., Phoenix, AZ (US)

(72) Inventor: Farhan Taghizadeh, Albuquerque, NM (US)

(73) Assignee: AESTHETICS BIOMEDICAL, INC., Phoenix, AZ (US)

( * ) Notice: Subject to any disclaimer, the term of this patent is extended or adjusted under 35 U.S.C. 154(b) by 0 days.

(21) Appl. No.: 15/373,325

(22) Filed: Dec. 8, 2016

(65) Prior Publication Data
US 2017/0165300 A1    Jun. 15, 2017

Related U.S. Application Data

(60) Provisional application No. 62/265,783, filed on Dec. 10, 2015, provisional application No. 62/299,447, filed on Feb. 24, 2016.

(51) Int. Cl.
| | | |
|---|---|---|
| *A61K 35/36* | (2015.01) | |
| *A61K 35/33* | (2015.01) | |
| *A61Q 19/00* | (2006.01) | |
| *A61K 9/00* | (2006.01) | |
| *A61Q 19/08* | (2006.01) | |
| *A61K 8/98* | (2006.01) | |
| *A61K 35/28* | (2015.01) | |
| *A61K 35/35* | (2015.01) | |
| *A61K 35/407* | (2015.01) | |
| *A61M 35/00* | (2006.01) | |
| *B02C 18/06* | (2006.01) | |
| *C12N 5/077* | (2010.01) | |
| *C12N 5/0775* | (2010.01) | |

(52) U.S. Cl.
CPC .............. *A61K 35/36* (2013.01); *A61K 8/981* (2013.01); *A61K 9/0014* (2013.01); *A61K 35/28* (2013.01); *A61K 35/33* (2013.01); *A61K 35/35* (2013.01); *A61K 35/407* (2013.01); *A61M 35/00* (2013.01); *A61Q 19/00* (2013.01); *A61Q 19/08* (2013.01); *B02C 18/06* (2013.01); *C12N 5/0656* (2013.01); *C12N 5/0668* (2013.01); *A61K 2800/82* (2013.01); *A61K 2800/86* (2013.01); *A61K 2800/87* (2013.01); *A61K 2800/91* (2013.01); *A61M 2202/09* (2013.01); *A61M 2202/097* (2013.01); *C12N 2500/84* (2013.01)

(58) Field of Classification Search
CPC ...... A61K 35/36; A61K 9/0014; A61K 35/33; A61K 35/407; A61K 35/35; A61K 35/28; A61K 8/981; A61K 2800/91; A61K 2800/87; A61K 2800/86; A61K 2800/82; A61M 35/00; A61M 2202/09; A61M 2202/097; B02C 18/06; C12N 5/0656; C12N 5/0668; C12N 2500/84; A61Q 19/00; A61Q 19/08
See application file for complete search history.

(56) References Cited

U.S. PATENT DOCUMENTS

| | | | |
|---|---|---|---|
| 7,767,452 B2 | 8/2010 | Kleinsek et al. | |
| 8,075,920 B2 | 12/2011 | Gammelsaeter et al. | |
| 8,518,879 B2 | 8/2013 | Al-Qahtani et al. | |
| 8,529,957 B2 | 9/2013 | Turzi et al. | |
| 8,945,537 B2 | 2/2015 | Turzi | |
| 9,119,974 B2 | 9/2015 | Al-Qahtani et al. | |
| 9,132,156 B1 | 9/2015 | Werber et al. | |
| 9,517,255 B2 | 12/2016 | Turzi | |
| 2006/0147430 A1 | 7/2006 | Sayre et al. | |
| 2007/0110737 A1* | 5/2007 | Mishra | A61K 8/983 424/93.72 |
| 2007/0122906 A1* | 5/2007 | Mishra | C12N 5/0018 435/372 |
| 2007/0154461 A1 | 7/2007 | Kleinsek | |
| 2008/0050346 A1* | 2/2008 | Jimenez | A61K 8/64 424/93.7 |
| 2009/0175927 A1* | 7/2009 | Gammelsaeter | A61K 8/97 424/449 |
| 2009/0202654 A1* | 8/2009 | Nixon | A61K 8/985 424/574 |
| 2011/0274665 A1* | 11/2011 | Maslowski | A61K 35/36 424/93.7 |
| 2012/0027705 A1 | 2/2012 | Gammelsaeter et al. | |
| 2012/0141399 A1 | 6/2012 | You et al. | |
| 2014/0099383 A1* | 4/2014 | Maslowski | A61K 8/985 424/572 |

(Continued)

FOREIGN PATENT DOCUMENTS

| | | |
|---|---|---|
| EP | 2 818 173 A1 | 12/2014 |
| WO | WO 2009/017321 A2 | 2/2009 |
| WO | WO 2011/101834 A1 | 8/2011 |

OTHER PUBLICATIONS

Mazlyzam et al. Human serum is an advantageous supplement for human dermal fibroblast expansion: clinical implications for tissue engineering of skin. Archives of Medical Research. 39 (2008):743-752.*
Eca et al. Autologous fibroblast culture in the repair of aging skin. Dermatol. Surg. 2012:38 p. 180-184.*
Age spots (live spots). 2017, Mayo clinic. p. 1.*

(Continued)

*Primary Examiner* — Taeyoon Kim

(74) *Attorney, Agent, or Firm* — Knobbe, Martens, Olson & Bear LLP

(57) ABSTRACT

Disclosed herein is a method of preparing a subject's cells for topical treatment of a subject in need. Also provided is a topical formulation and methods of treating a subject suffering a skin disorder and pain using the topical formulation. Also disclosed herein are devices and systems for micronizing an aspirate in preparation of such a topical formulation.

18 Claims, 24 Drawing Sheets

(56) References Cited

U.S. PATENT DOCUMENTS

| | | | |
|---|---|---|---|
| 2015/0023908 A1* | 1/2015 | Al-Qahtani | A61Q 19/08 424/85.2 |
| 2015/0110892 A1 | 4/2015 | Gammelsaeter et al. | |
| 2015/0151858 A1 | 6/2015 | Turzi | |
| 2015/0307844 A1 | 10/2015 | Sturm | |
| 2015/0335686 A1 | 11/2015 | Spencer et al. | |
| 2016/0158286 A1 | 6/2016 | Turzi | |
| 2016/0206550 A1 | 7/2016 | Balasubramanian et al. | |
| 2016/0206551 A1 | 7/2016 | Boss, Jr. | |
| 2016/0220479 A1 | 8/2016 | During et al. | |

OTHER PUBLICATIONS

Kim et al. Can platelet-rich plasma be used for skin rejuvenation? Evaluation of effects of platelet-rich plasma on human dermal fibroblast. Ann. Dermatol. vol. 23, No. 4, 2011: p. 424-431.*

Kumar et al. Autologous therapies in dermatology. J. Clin. Aesthet. Dermatol. 2014;7(12):38-45.*

Ranzato et al. Platelet lysate promotes in vitro wound scratch closure of human dermal fibroblasts: different roles of cell calcium, p38, ERK and PI3K/AKT. J. Cell. Mol. Med. vol. 13. No. 8B, 2009: p. 2030-2038.*

Thangapazham et al. Alteration of Skin Properties with Autologous Dermal Fibroblasts. Int. J. Mol. Sci. 2014, 15, 8407-8427 (Year: 2014).*

Watson et al. The Effect of Therapeutic Human Serum Drops on Corneal Stromal Wound-Healing Activity. Current Eye Research, 33:8, 641-652 (Year: 2008).*

Liu et al. The effect of serum concentration on the growth, proliferation and collagen secretion in mouse L929 fibroblasts. Xi Bao Yu Fen Zi Mian Yi Xue Za Zhi. Jul. 2011;27(7):736-9. English Abstract only (p. 1-2) (Year: 2011).*

Gray et al. Rapid Cell Culture Procedure for Tissue Samples. American Journal of Medical Genetics 28:521-526 (1987) (Year: 1987).*

Reed et al. TGF-PI Induces the Expression of Type I Collagen and Sparc, and Enhances Contraction of Collagen Gels, by Fibroblasts From Young and Aged Donors. Journal of Cellular Physiology 158:169-179 (Year: 1994).*

Fischer et al. Clinical-Grade Human Platelet Lysate Produced at Industrial Scale for Isolation, Expansion, and Cryopreservation of Mesenchymal Stromal Cells. ISSCR Poster Presentation, Vancouver, 2014 (Year: 2014).*

VISIA-CR. Facial Imaging System for Clinical Research. Canfield. downloaded from web.archive.org/web/20151020054613/https://www.canfieldsci.com/imaging-systems/visia-cr/ on Sep. 17, 2018. p. 1-5 (Year: 2015).*

Bernardi et al. Production of human platelet lysate by use of ultrasound for ex vivo expansion of human bone marrowederived mesenchymal stromal cells. Cytotherapy, 2013; 15: 920-929 (Year: 2013).*

Bernardi et al. Fast production of human platelet lysate by platelet rich plasma sonication for the ex vivo expansion of bone marrow-derived mesenchymal stromal cells. Cytotherapy. Volume 16, Issue 4, Supplement, Apr. 2014, p. S104 (Year: 2014).*

Ranzato et al. Platelet lysate promotes in vitro wound scratch closure of human dermal fibroblasts: different roles of cell calcium, P38, ERK and PI3K/AKT. J. Cell. Mol. Med. vol. 13, No. 8B, 2009 pp. 2030-2038 (Year: 2009).*

Flannent et al. Facial skin pores: a multiethnic study. Clinical, Cosmetic and Investigational Dermatology 2015:8 85-93 (Year: 2015).*

Fekete et al. "Platelet lysate from whole blood-derived pooled platelet concentrates and apheresis-derived platelet concentrates for the isolation and expansion of human bone marrow mesenchymal stromal cells: production process, content and identification of active components." Cytotherapy. May 2012; 14(5): 540-554.

Remington's Pharmaceutical Sciences, 18th Ed., Mack Publishing Co., Easton, Pa. (1990).

Riordan et al. "Scalable efficient expansion of mesenchymal stem cells in xeno free media using commercially available reagents" J. Transl. Med 13:232 (2015).

Schallmoser et al. "Preparation of pooled human platelet lysate (pHPL) as an efficient supplement for animal serum-free human stem cell cultures." J Vis Exp. Oct. 30, 2009 ;(32).

Shih et al. "Preparation, quality criteria, and properties of human blood platelet lysate supplements for ex vivo stem cell expansion." New Biotechnology vol. 32, Issue 1, Jan. 25, 2015, p. 199-211.

International Search Report and Written Opinion dated Mar. 28, 2017, received in related application PCT/US2016/065572.

Nelson, Bryn. "A superficial success." Nature Reports Stem Cells (2009).

* cited by examiner

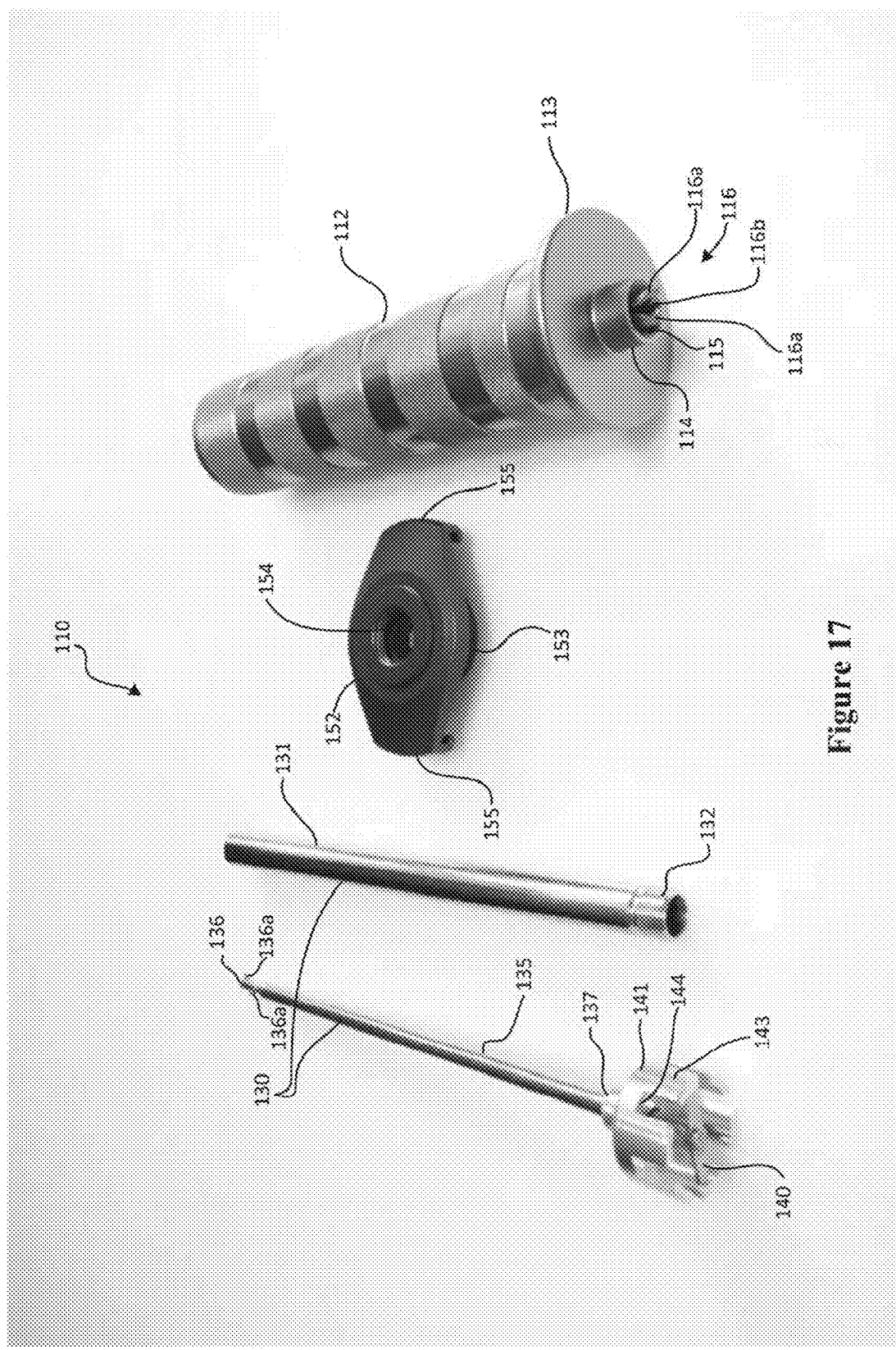

```
                              ┌─ 240
                              ▼
                ┌──────────────────────────┐─ 241
                │  Load an Aspirate into a │
                │       Container          │
                └──────────────┬───────────┘
                               ▼
                ┌──────────────────────────┐─ 243
                │  Insert a Blade into the │
                │        Container         │
                └──────────────┬───────────┘
                               ▼
                ┌──────────────────────────┐─ 245
                │   Connect the Blade to a │
                │ Motor for Causing Rotation│
                │       of the Blade       │
                └──────────────┬───────────┘
                               ▼
                ┌──────────────────────────┐─ 247
                │   Cause the Blade to Rotate│
                │   within the Container to │
                │   Micronize the Aspirate  │
                │   without Use of an Enzyme│
                └──────────────────────────┘
```

Figure 24

TOPICAL FORMULATION FOR SKIN CARE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, the present application claims priority to U.S. Provisional Application Ser. No. 62/265,783, entitled "Topical Formulation for Skin Care," filed Dec. 10, 2015, and U.S. Provisional Application Ser. No. 62/299447, also entitled "Topical Formulation for Skin Care," filed Feb. 24, 2016, the entire contents of which are hereby expressly incorporated by reference in their entireties.

BACKGROUND

Field of the Disclosure

The present disclosure relates to the topical formulations and methods useful for treating skin disorders, pain, and inflammation. In particular, a topical formulation for topical treatment of skin is provided, as well as devices, systems and methods useful in its preparation. Methods of using the topical formulations are also disclosed.

Description

The maintenance and improvement of skin tone, elasticity, and youthful appearance of skin is desirable by many. With age, skin loses elasticity, appears rougher, thins out, and acquires some level of skin damage. This may lead to sagging, discoloration, brown spots, UV damage, and wrinkles. Aside from surgical procedures, such as plastic surgery, to improve the look of skin or injectable treatments such as Botox® or Juvaderm®, many people resort to skin care compositions, including prescription skin treatments, in order to maintain or improve the integrity of their skin and prevent damage. Popular treatments include Retin-A (tretinoin), hydroquinone, glycolic acid, and beta hydroxyl acid to remove a top layer of skin to encourage new skin growth. Many treatments, however, that lead to improved skin tone and elasticity can take weeks to improve the look of skin and can also be very irritating. For example, Retin-A and hydroquinone can lead to sun sensitivity, peeling, dryness and even worsening of acne. Glycolic acid and beta hydroxy acid are not advisable for those with sensitive skin. As such, new developments in skin care are desirable. Described herein is the use of live cells for the treatment of skin disorders, inflammation, and/or pain. Also described herein are devices, systems, and methods useful in the preparation of a formulation for such a treatment.

SUMMARY

Treatments for skin disorders have been limited to drugs that have to be taken orally or for topical use creams and ointments. As described herein, is the use of live cells taken from a subject suffering from a skin disorder or treatment of pain.

In a first aspect, a method of making a cell for topical treatment of a subject in need is provided. The method can include, for example, obtaining cells from the subject, placing cells in growth media, the growth media including human platelet lysate or human serum, and growing the cells up to confluency. In some embodiments, the cell is selected from a group consisting of skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized. In some embodiments, the organ extract is micronized. In some embodiments, the growth media includes human platelet lysate. In some embodiments, the growth media comprises human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage.

In a second aspect, a cell is provided. The cell can be manufactured by a method of any one of the described embodiments herein. The method can include, for example, obtaining cells from the subject, placing cells in growth media, wherein the growth media includes human platelet lysate or human serum and growing the cells up to confluency. In some embodiments, the cell is selected from skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized. In some embodiments, the organ extract is micronized. In some embodiments, the cell is selected from an organ extract, such as a liver or a kidney. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell.

In a third aspect, a topical formulation is provided. The topical formulation can include, for example, the cells made by the methods of any of the embodiments described herein or the cell of any of the embodiments described herein. The cell can be manufactured by a method of any of the described embodiments herein. The method can include obtaining cells from the subject, placing cells in growth media, wherein the growth media includes human platelet lysate or human serum and growing the cells up to confluency. In some embodiments, the cell is selected from skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized.

In some embodiments, the organ extract is micronized. In some embodiments, the cell is selected from an organ extract, such as a liver or a kidney. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media includes human platelet lysate. In some embodiments, the growth media includes human serum. In some embodiments, the growth media includes fibroblast differentiation media.

In a fourth aspect, a formulation for injection is provided. The formulation can have the cell of any one or more of the embodiments described herein. The formulation can be manufactured by any one or more of the methods described herein. The method can include obtaining cells from the subject, placing cells in growth media, wherein the growth media includes human platelet lysate or human serum and growing the cells up to confluency. In some embodiments, the cell is selected from skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized. In some embodiments, the organ extract is micronized. In some embodiments, the cell is selected from an organ extract, such as a liver or a kidney. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media includes human platelet lysate. In some embodiments, the growth media includes human serum. In some embodiments, the growth media includes fibroblast differentiation media. In some embodiments, the cell is from fat aspirate. In some embodiments, the formulation further comprises a pharmaceutical vehicle.

In a fifth aspect, a method of treating a subject suffering from a skin disorder is provided. The method can include, for example, obtaining cells from the subject, placing cells in growth media, the growth media including human platelet lysate or human serum, growing the cells up to confluency, providing the cells to the subject alone or in a topical formulation to the subject, applying the cell or topical formulation to the subject. In some embodiments, the cell or topical formulation is applied onto skin. The cell can be manufactured by a method of any of the embodiments described herein. The method can include obtaining cells from the subject, placing cells in growth media, the growth media including human platelet lysate or human serum and growing the cells up to confluency. In some embodiments, the cell is selected from skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized. In some embodiments, the organ extract is micronized. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media includes human platelet lysate. In some embodiments, the growth media includes human serum. In some embodiments, the growth media includes fibroblast differentiation media. In some embodiments, the skin disorder is selected from a group of psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, and impetigo. In some embodiments, the applying is performed 1, 2, 3 or 4 times a day. In some embodiments, the applying is performed one or more times a day for 1 day, 3 days, 7 days, 14 days, 21 days or 28 days or any number of days in between any two aforementioned numbers of days, for example, 1, 2, 3, 4, 5, 6, 7, 8, 9, 10, 11, 12, 13, 14, 15, 16, 17, 18, 19, 20, 21, 22, 23, 24, 25, 26, 27, or 28 days.

In a sixth aspect, a method of treating a subject suffering from pain is provided, the method can include, for example, obtaining cells from the subject, placing cells in growth media, the growth media including human platelet lysate or human serum, growing the cells up to confluency, providing the cells to the subject alone or in a topical formulation to the subject, applying the cell or topical formulation to the subject, the cell or topical formulation being applied onto skin. The cell can be manufactured by a method of any of the described embodiments herein. The method can include obtaining cells from the subject, placing cells in growth media, the growth media including human platelet lysate or human serum and growing the cells up to confluency. In some embodiments, the cell is selected from skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, the cell is selected from an organ extract, such as a liver or a kidney. In some embodiments, the aspirate or amnio/placental tissue is micronized. In some embodiments, the organ extract is micronized. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media includes human platelet lysate. In some embodiments, the growth media includes human serum. In some embodiments, the growth media includes fibroblast differentiation media. In some embodiments, the pain is from arthritis. In some embodiments, the pain is from a disease. In some embodiments, the applying is performed 1, 2, 3 or 4 times a day. In some embodiments, the applying is performed for 1 day, 3 days, 7 days, 14 days, 21 days or 28 days or any number of days in between any two aforementioned numbers of days.

In a seventh aspect, a method of treating skin is provided. The method can include obtaining cells from the subject, placing the cells in growth media, the growth media including human platelet lysate or human serum, growing the cells up to confluency, providing the cells in an injectable formulation to the subject and injecting the formulation into a facial region or neck region of the subject. The formulation can include a pharmaceutical vehicle.

In an eighth aspect, a system for micronizing an aspirate is provided. The system can be used in the preparation of any of the formulations described above or throughout this disclosure. The system includes a handpiece. The handpiece includes a handle and a motor disposed within the handle. The handpiece also includes a blade positionable within a syringe barrel. The syringe barrel can contain an aspirate. The blade is rotationally coupled to the motor by a drive shaft. The handpiece also includes an end cap positioned along the drive shaft between the blade and the handle. The end cap including an opening through which the drive shaft extends. The end cap can be configured to seal the syringe barrel. In some embodiments, the drive shaft slidingly engages with the opening of the end cap. In some embodiments, the drive shaft includes a hollow, cylindrical outer sheath having a first end that engages the handle. In some embodiments, the drive shaft includes a cylindrical inner shaft configured to rotate within the outer sheath. In some embodiments the inner shaft includes a first end configured to engage an output shaft of the motor, and a second end attached to the blade. In some embodiments, the system further includes a blade guard attached to the second end of the inner shaft. In some embodiments, the system further includes the syringe barrel. In some embodiments, the syringe barrel is a 60 cc syringe barrel. In some embodiments, the system further includes a control box. In some embodiments, the control box includes a motor controller configured for controlling operation of the motor, and a connector for the handpiece to the control box with a handpiece cable. In some embodiments, the control box includes a display and user inputs. In some embodiments, the control box comprises a processor and a memory. In some embodiments, the system includes a foot pedal. In some embodiments, the pedal is connected to the control box with a pedal cable. In some embodiments, the aspirate is a fat aspirate obtained from a patient during liposuction.

In a ninth aspect, a method for micronizing an aspirate is provided. The method can comprise loading an aspirate into a syringe barrel of a syringe, inserting a blade into the syringe barrel, connecting the blade to a handpiece, the handpiece including a motor for causing rotation of the blade, causing the blade to rotate within the syringe barrel to micronize the aspirate. In some embodiments, loading an aspirate comprises withdrawing a plunger of the syringe. In some embodiments, the method further comprises the plunger from the syringe barrel after loading the aspirate into the syringe barrel. In some embodiments, the method further comprises sealing an open end of the syringe barrel with an end cap. In some embodiments, a drive shaft extends through the end cap between the blade and the handpiece. In some embodiments, causing the blade to rotate comprises pressing a pedal. In some embodiments, the method further comprises moving the handpiece relative to the syringe barrel to move the blade through the aspirate.

In a tenth aspect, a method for micronizing an aspirate is provided. The method can comprise loading an aspirate into a container, inserting a blade into the container, connecting the blade to a motor for causing rotation of the blade, causing the blade to rotate within the container to micronize the aspirate, wherein the aspirate is micronized without use of an enzyme. In some embodiments, the enzyme is collagenase. In some embodiments, the container is a syringe barrel of a syringe. In some embodiments, loading an aspirate comprises withdrawing a plunger of the syringe. In some embodiments, the method further comprises the plunger from the syringe barrel after loading the aspirate into the syringe barrel. In some embodiments, the method further comprises sealing an open end of the syringe barrel with an end cap. In some embodiments, a drive shaft extends through the end cap between the blade and a handpiece. In some embodiments, the method further comprises causing the blade to rotate comprises pressing a pedal.

BRIEF DESCRIPTION OF THE DRAWINGS

The features and advantages of the methods, devices and systems described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

Human Platelet Lysate, serum PLUS™ Human Platelet Lysate and lyophilized and reconstituted serum PLUS™ Human Platelet Lysate.

Figure 5:
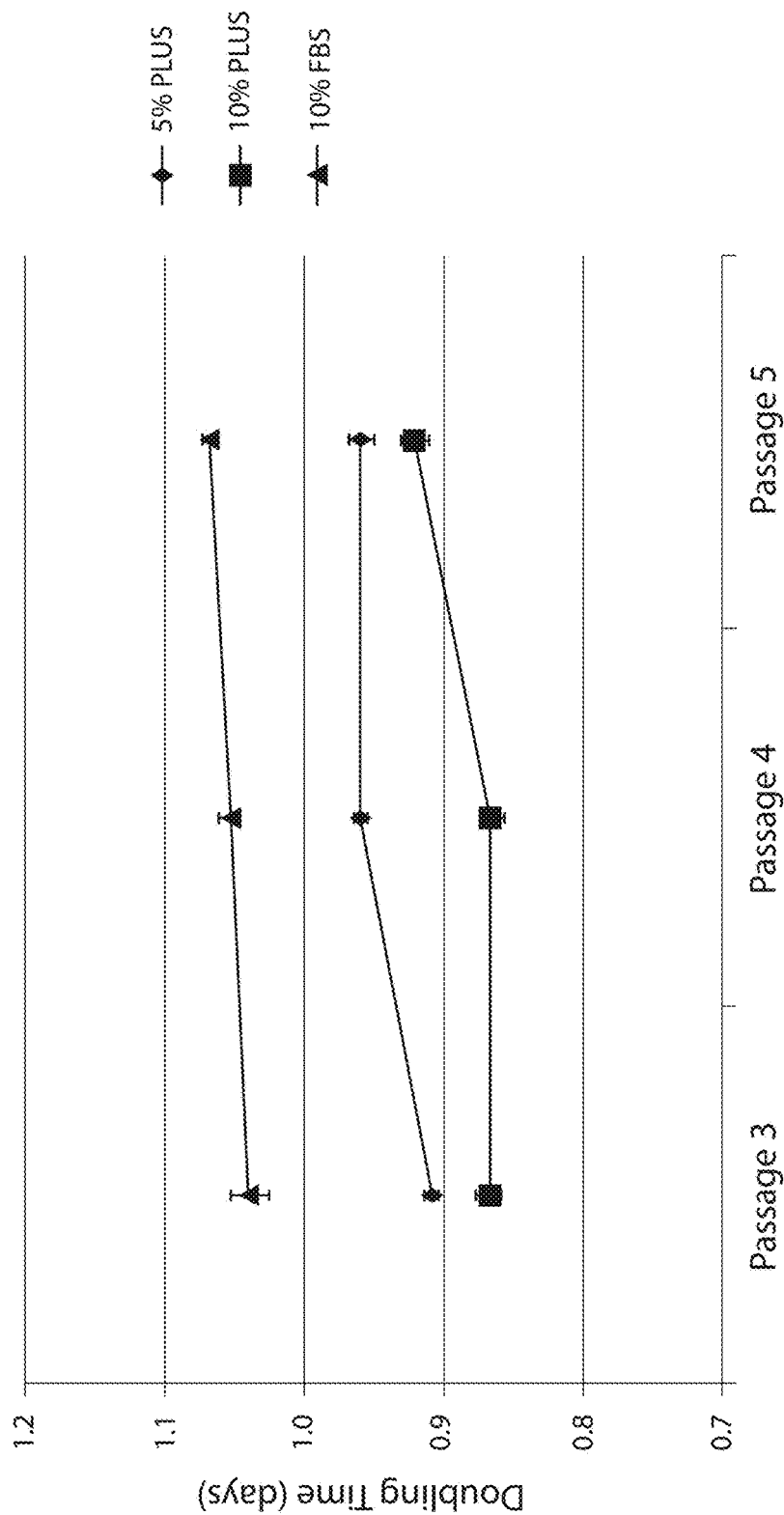

FIG. 5 shows the proliferation of fibroblasts in different concentrations of PLUS™ through 5 passages of the cells. As shown is the growth of cells in 10% FBS, 5% PLUS™, and 10% PLUS™.

Figure 6:
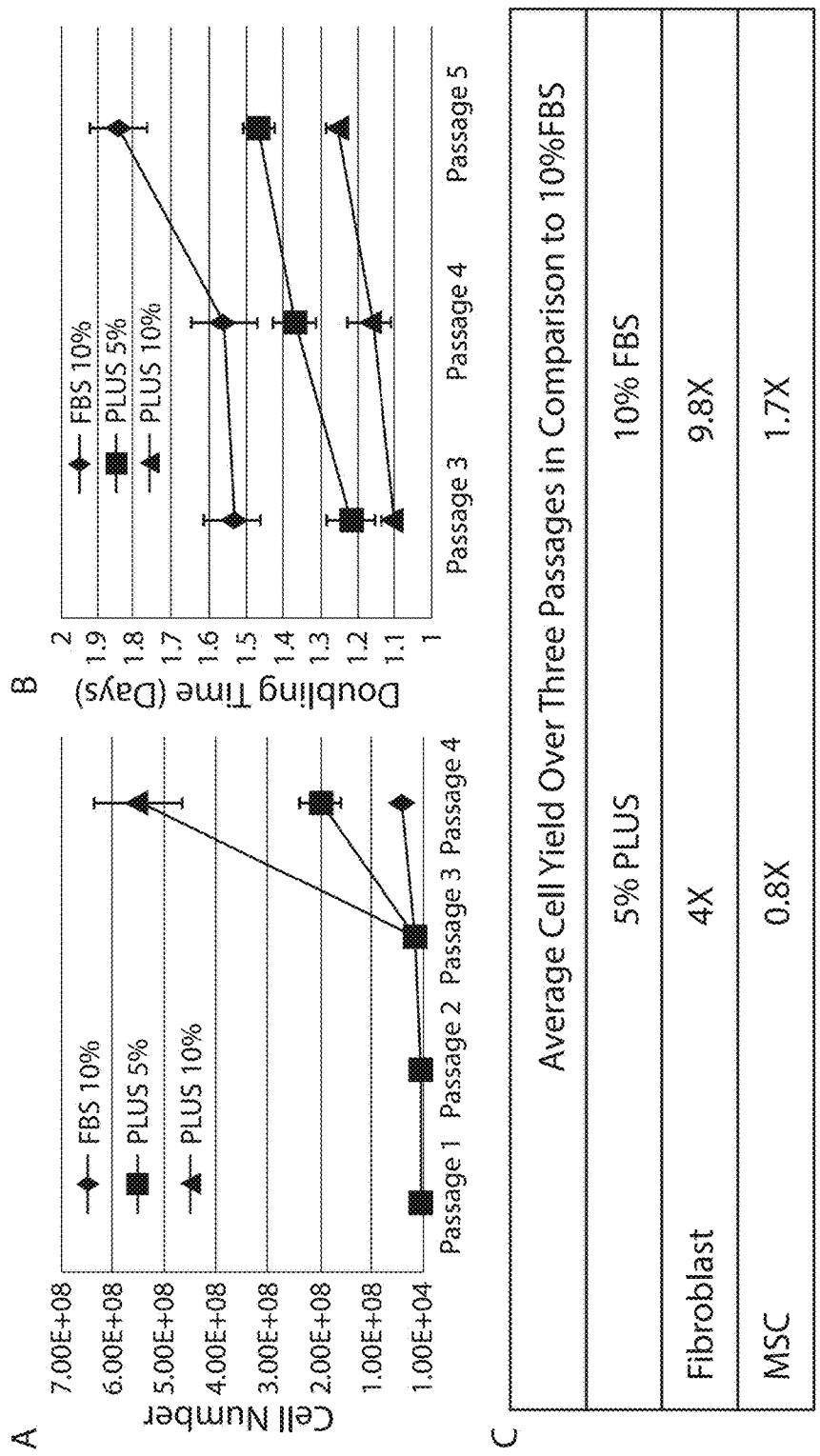

FIG. 6 (Panels A-C) shows the impact of PLUS™ in cell proliferation and time.

Figure 7:
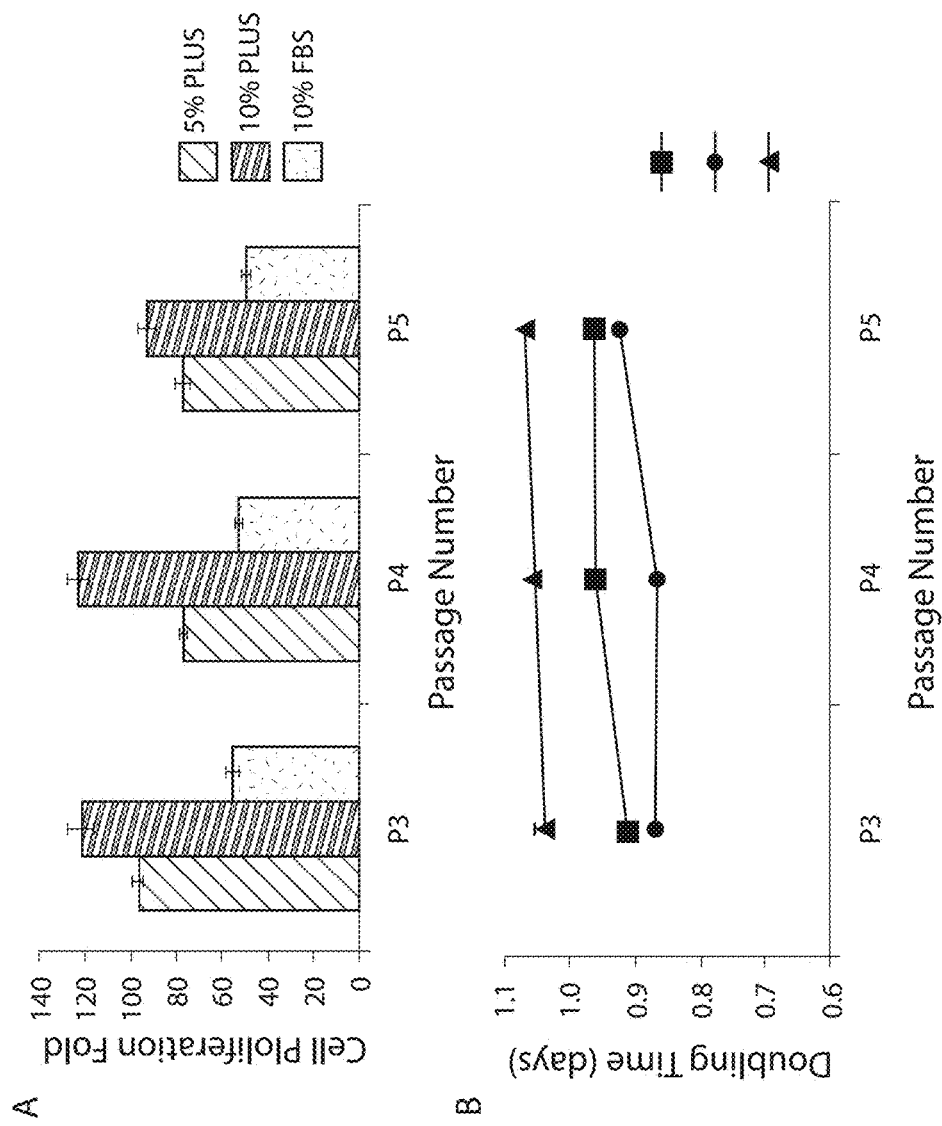

FIG. 7 (Panels A and B) shows the proliferation of fibroblasts in human platelet lysate (PLUS™) in comparison to growth in fetal bovine serum (FBS).

Figure 8:
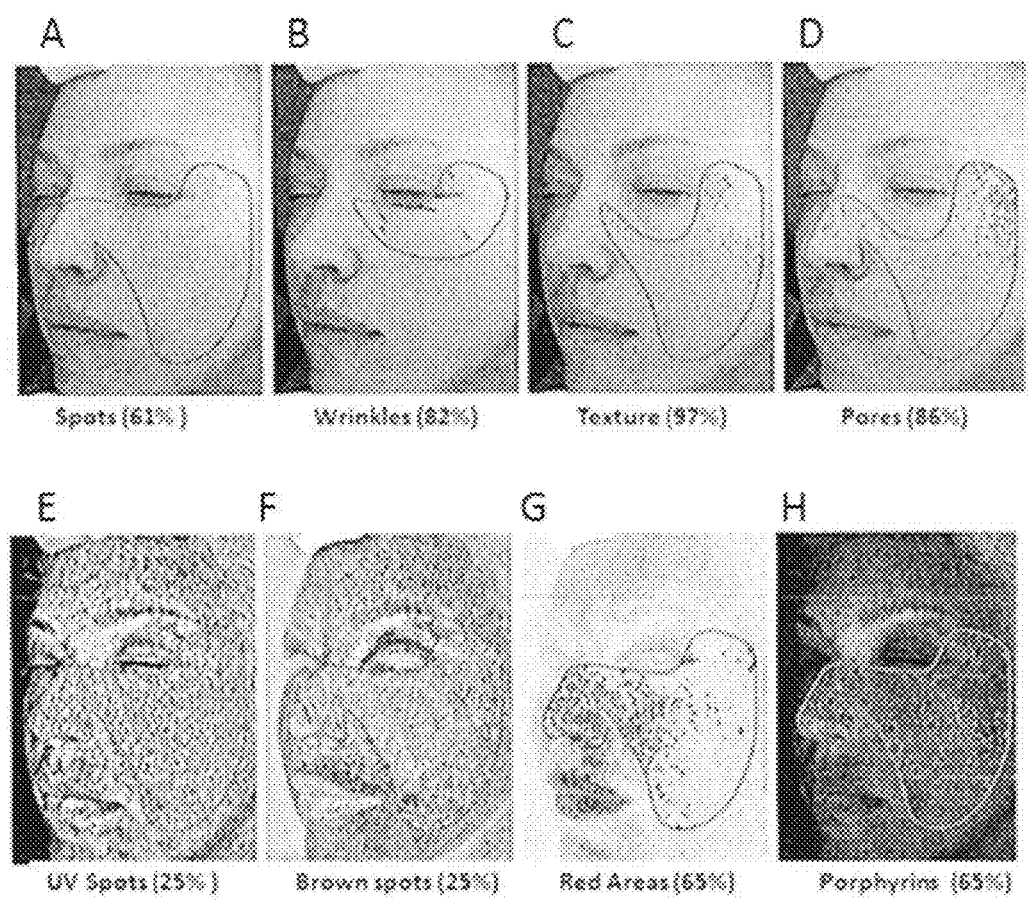

FIG. 8 shows a facial assessment report for a female patient before being treated with a topical formulation containing the patient's skin cells. Panels A-H show the assessment of spots, wrinkles, texture, pores, UV spots, brown spots, red areas and porphyrins, respectively.

Figure 9:
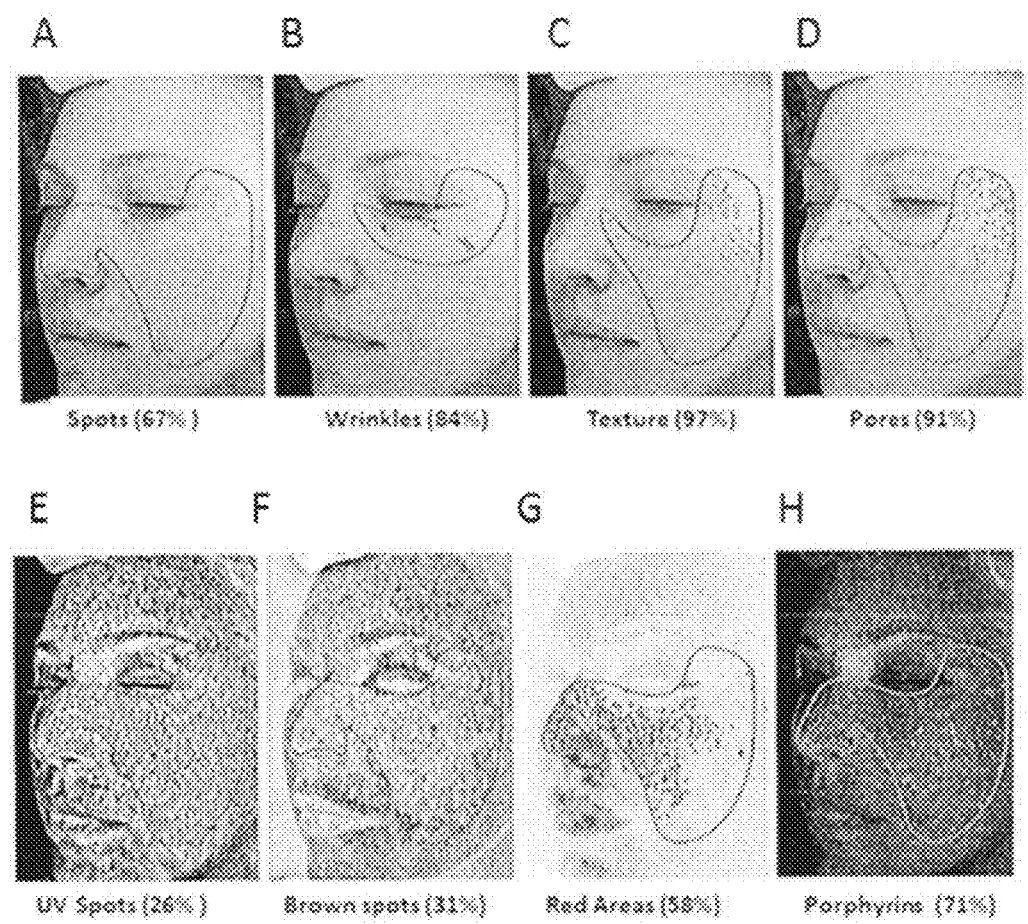

FIG. 9 shows a facial assessment report for the female patient in FIG. 8 after being treated with a topical formulation containing the patient's skin cells for 20 days (three weeks). Panels A-H show the assessment of spots, wrinkles, texture, pores, UV spots, brown spots, red areas and porphyrins, respectively.

Figure 10:
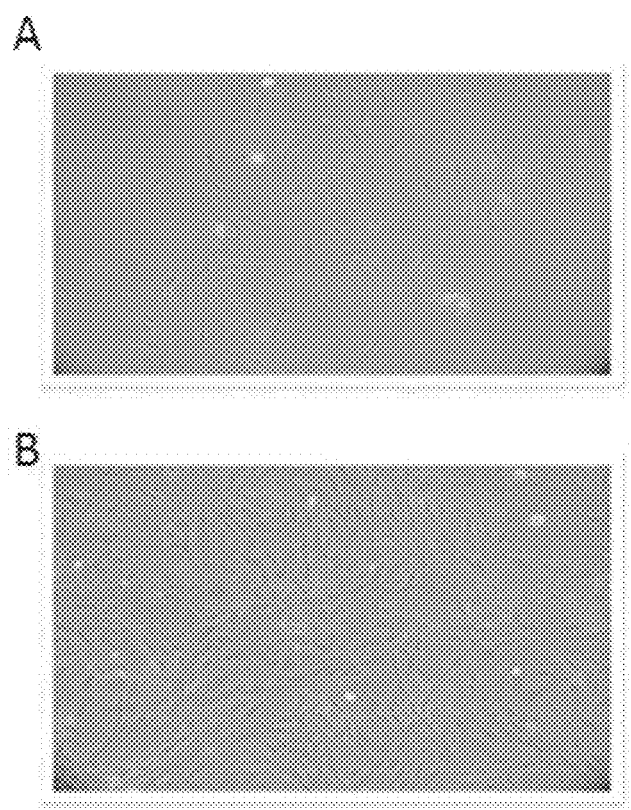

FIG. 10 shows the PTAC (Personal treatment and care) of Donor 1 at day 9 after initial seeding (Panel A) and day 12 after initial seeding (Panel B).

Figure 11:
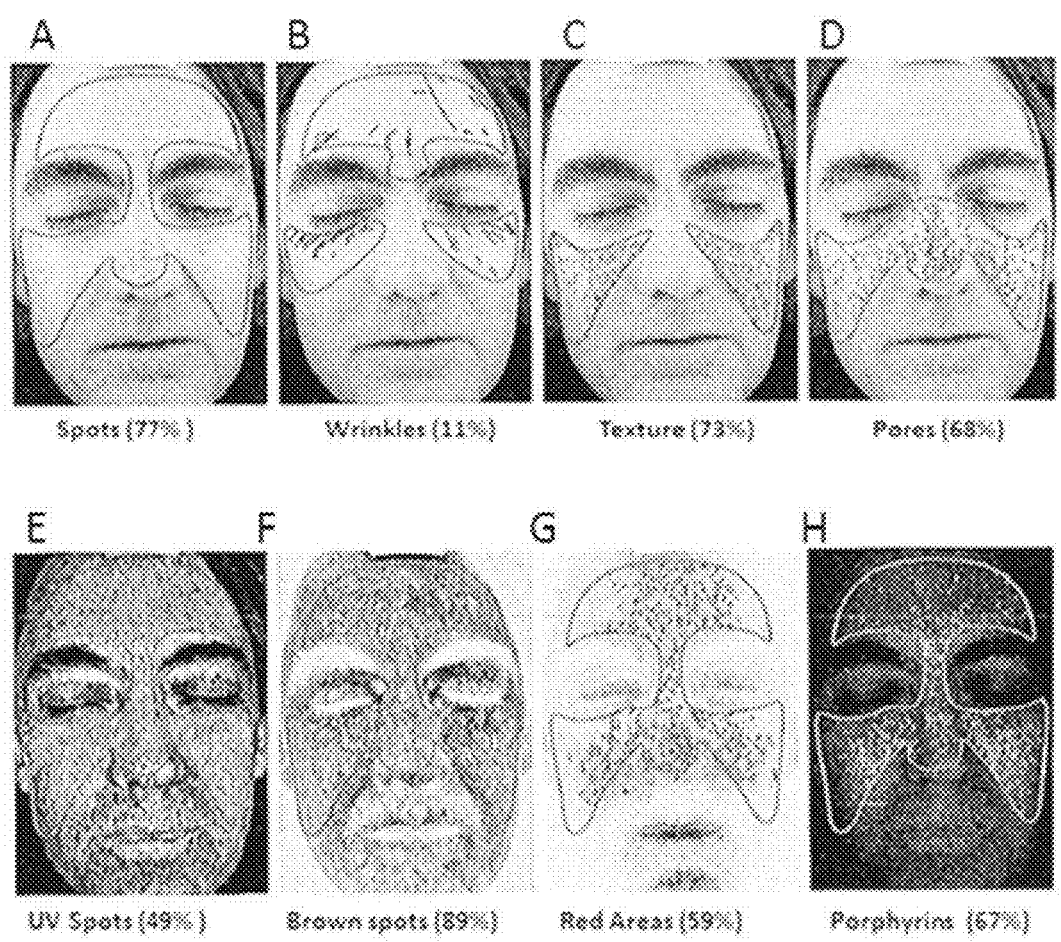

FIG. 11 shows a facial assessment report for a male patient before being treated with a topical formulation containing the patient's skin cells. Panels A-H show the assessment of spots, wrinkles, texture, pores, UV spots, brown spots, red areas and porphyrins, respectively.

Figure 12:
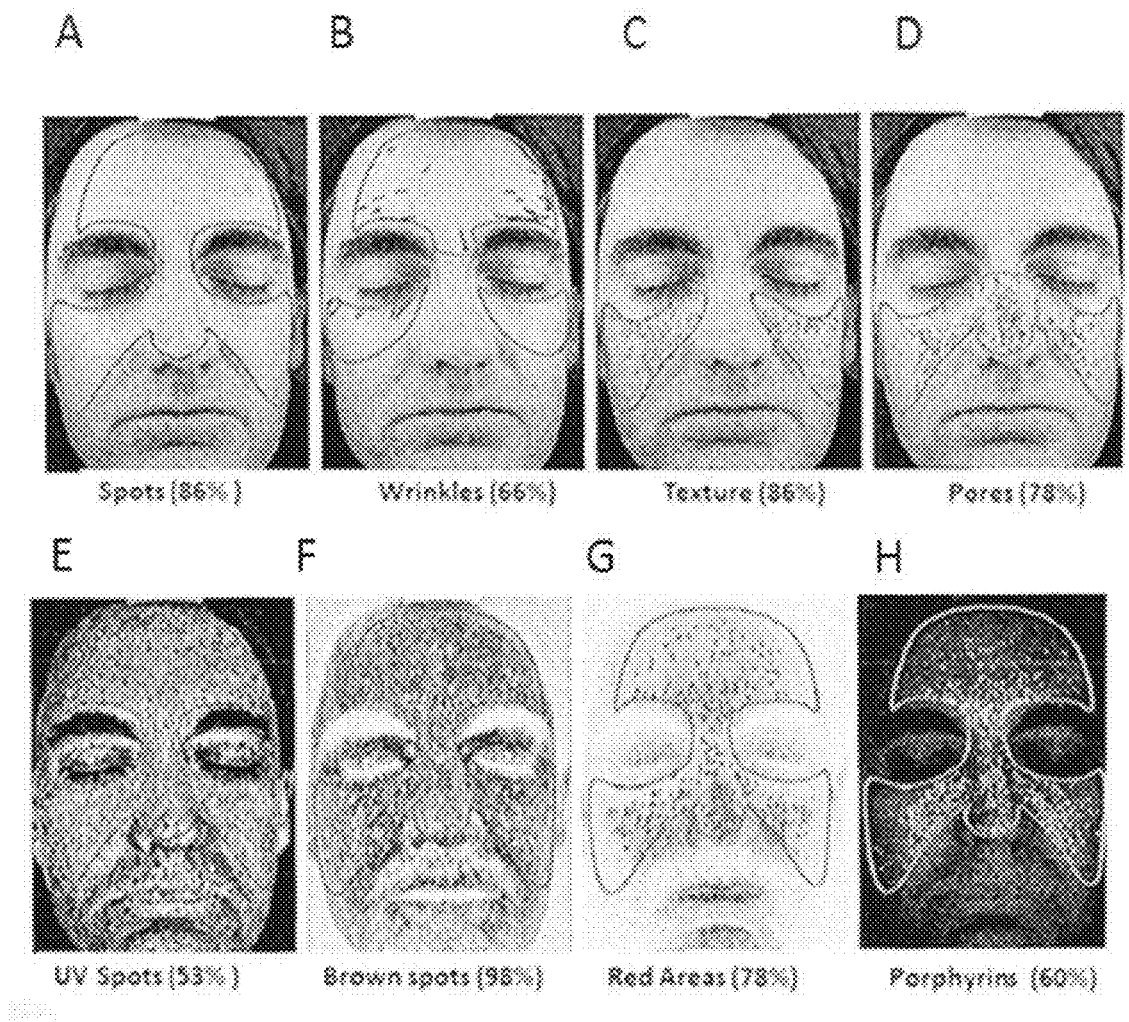

FIG. 12 shows a facial assessment report for the male patient in FIG. 11 after being treated with a topical formulation containing the patient's skin cells for 20 days (three weeks). Panels A-H show the assessment of spots, wrinkles, texture, pores, UV spots, brown spots, red areas and porphyrins, respectively.

Figure 13:
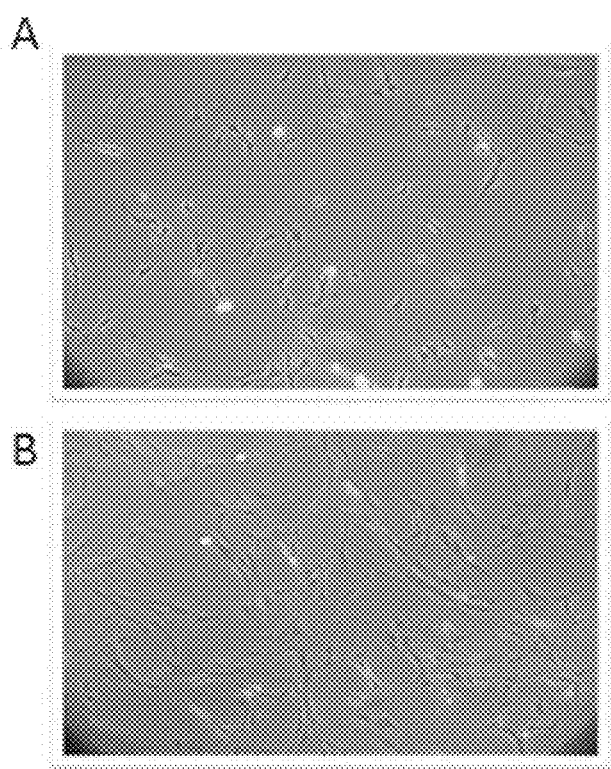

FIG. 13 shows the PTAC (Personal treatment and care) of Donor 2 at day 9 after initial seeding (Panel A) and day 12 after initial seeding (Panel B).

Figure 14:
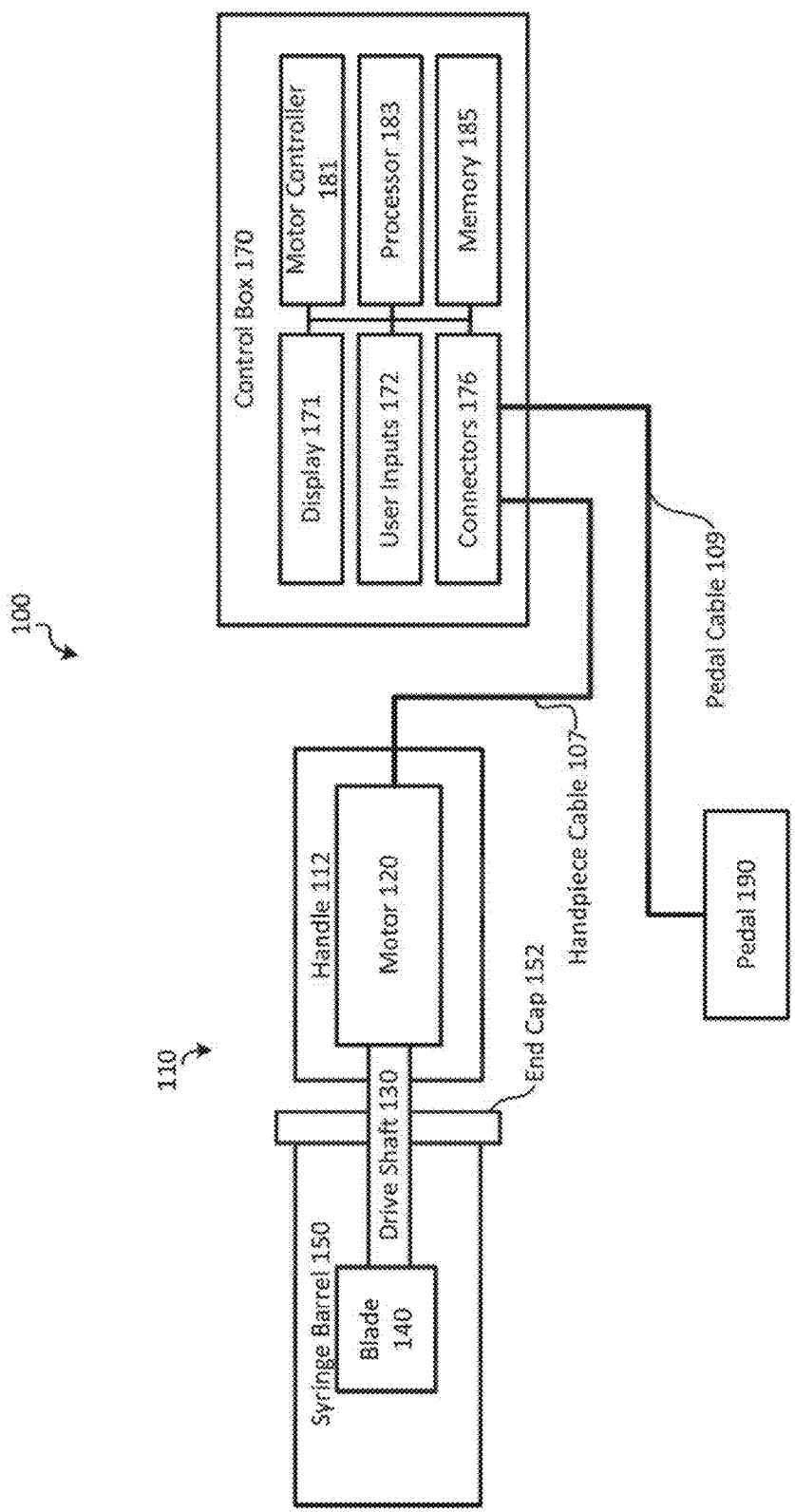

FIG. 14 is a block diagram illustrating one embodiment of a system for micronizing an aspirate.

Figure 15:
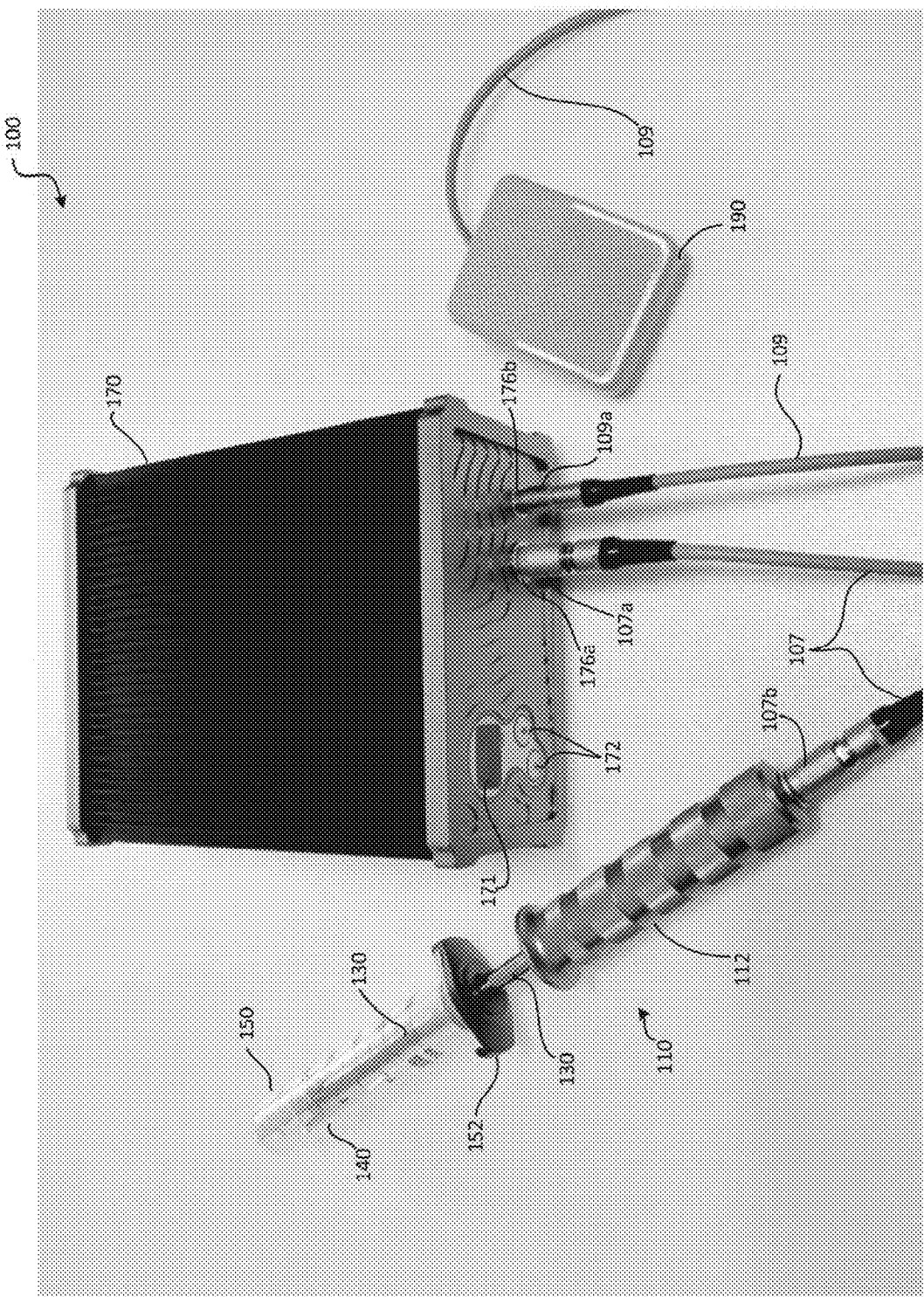

FIG. 15 shows a perspective view of one embodiment of the system of FIG. 14.

Figure 16:
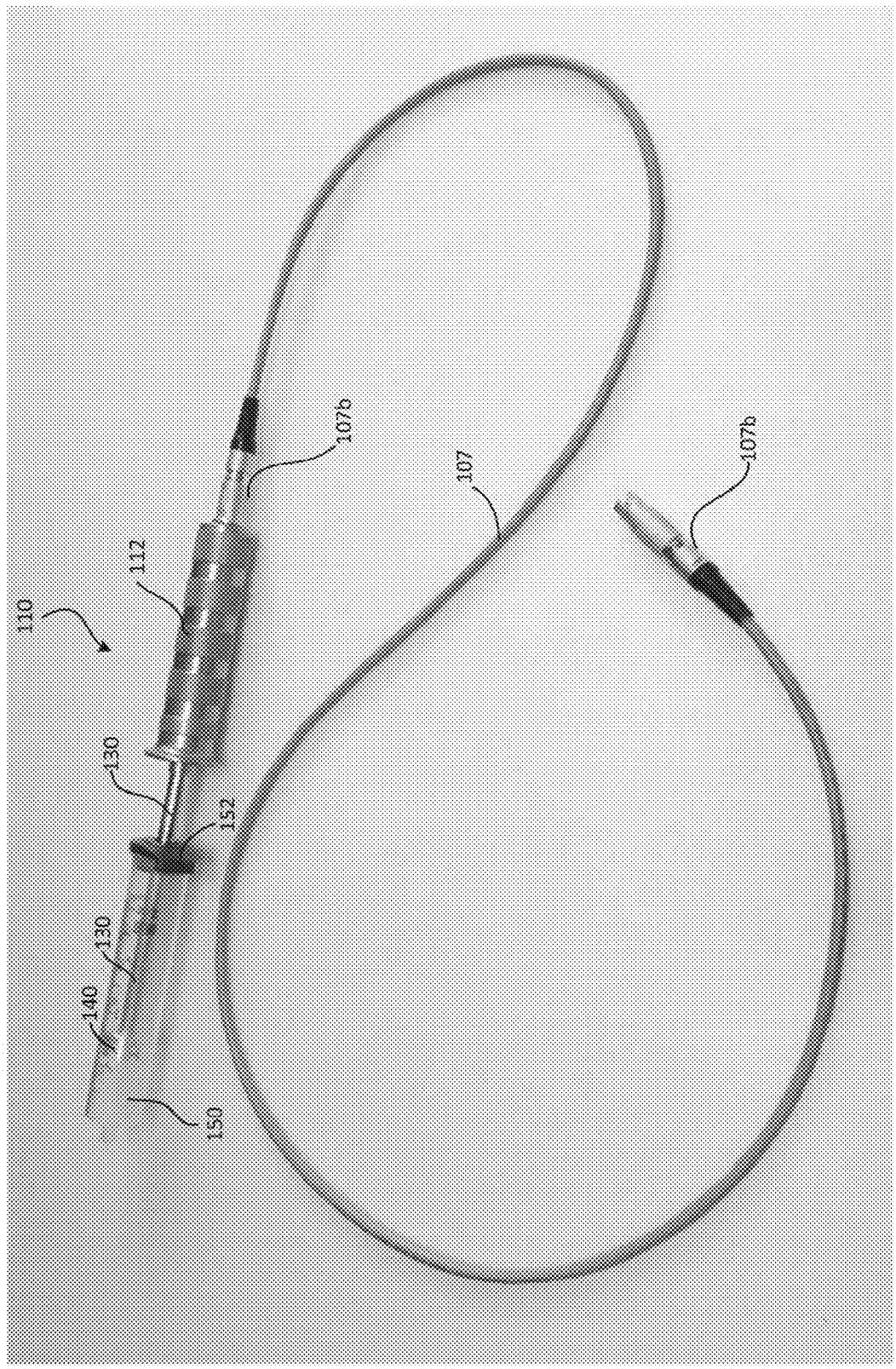

FIG. 16 shows an embodiment of a handpiece of the system of FIG. 15.

FIG. 17 shows embodiments of several of the components of the handpiece of FIG. 16.

Figure 18A:
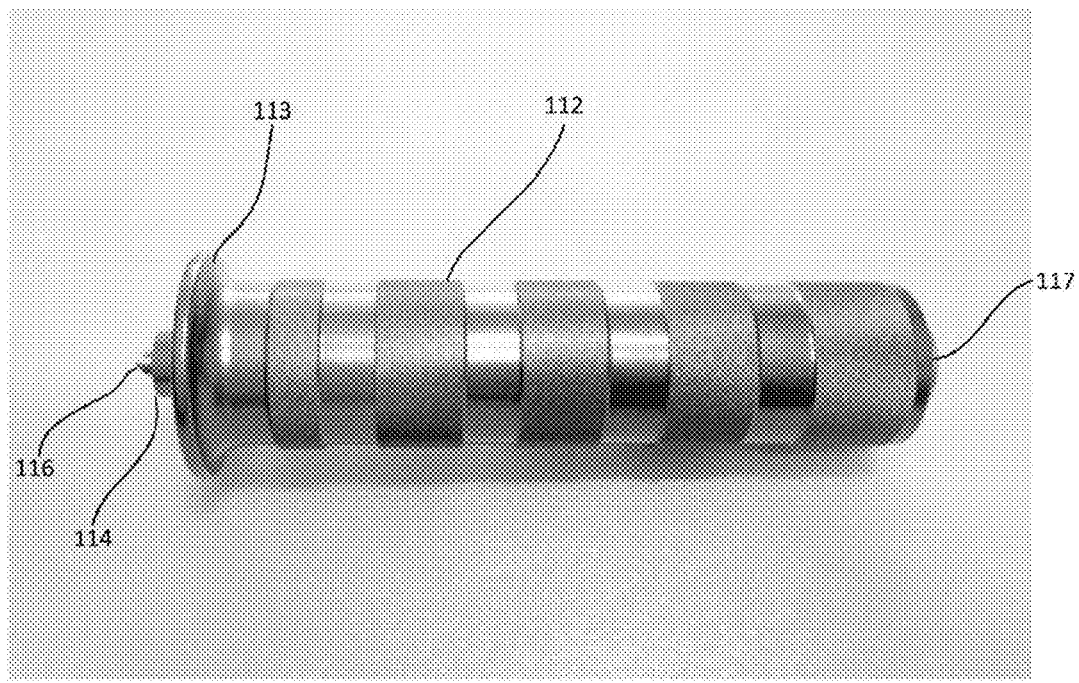
Figure 18B:
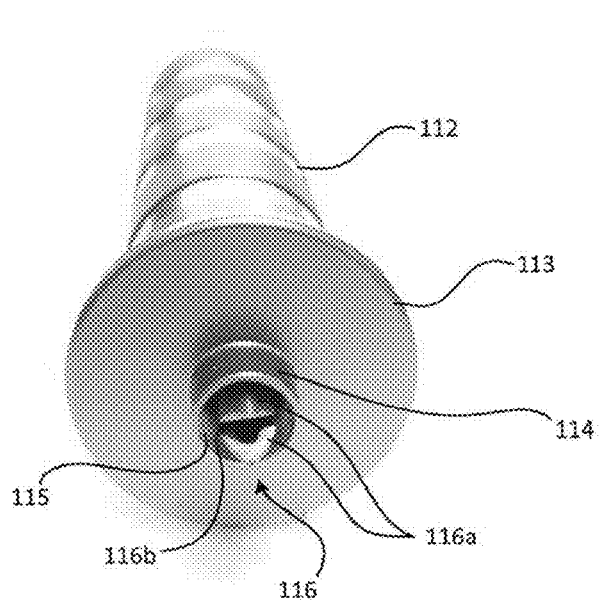

FIGS. 18A and 18B show side perspective and end perspective views, respectively, of an embodiment of the handle of the handpiece of FIG. 16.

Figure 19:
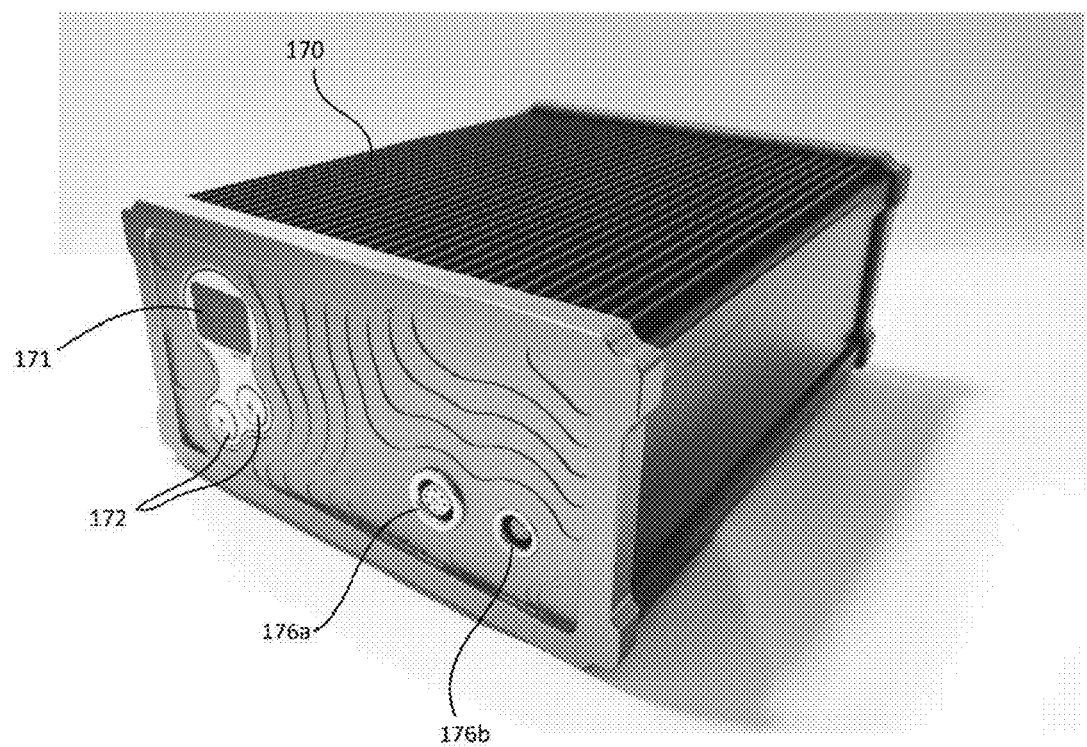

FIG. 19 shows a perspective view of an embodiment of a control box of the system of FIG. 15

Figure 20:
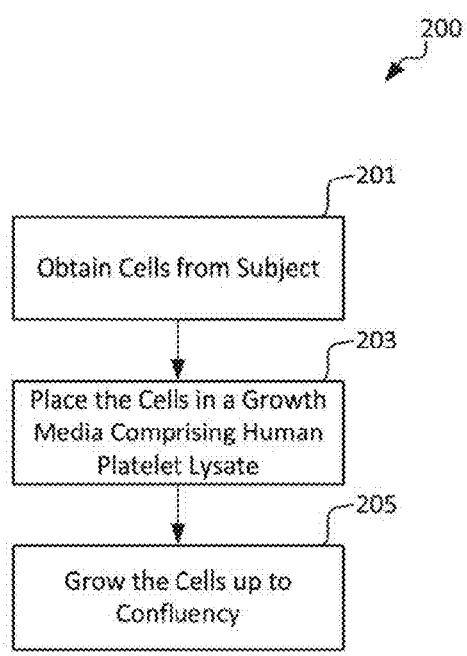

FIG. 20 shows a flow diagram of an embodiment described herein, of the method of making a cell for treatment of a subject.

Figure 21:
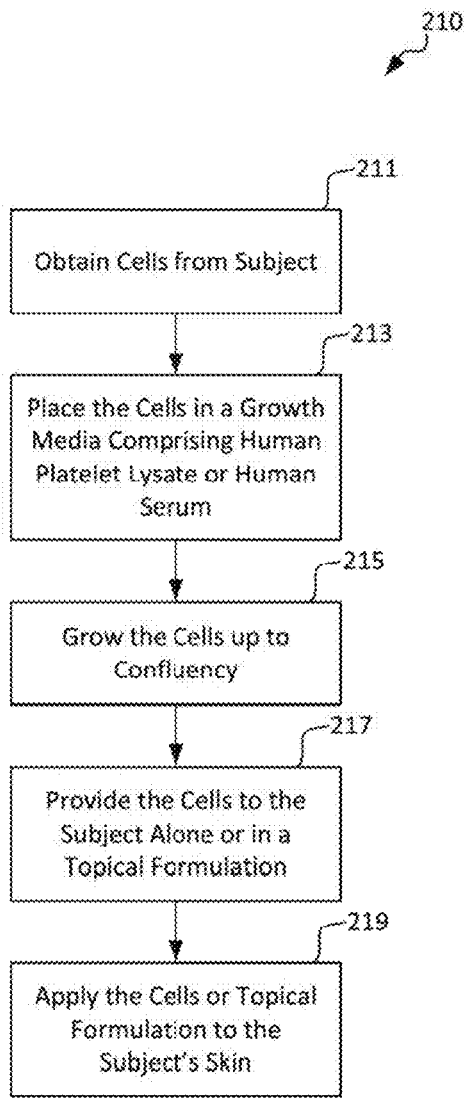

FIG. 21 shows a flow diagram of an embodiment described herein, of a method of treating a subject suffering of a skin disorder or a subject suffering from pain.

Figure 22:
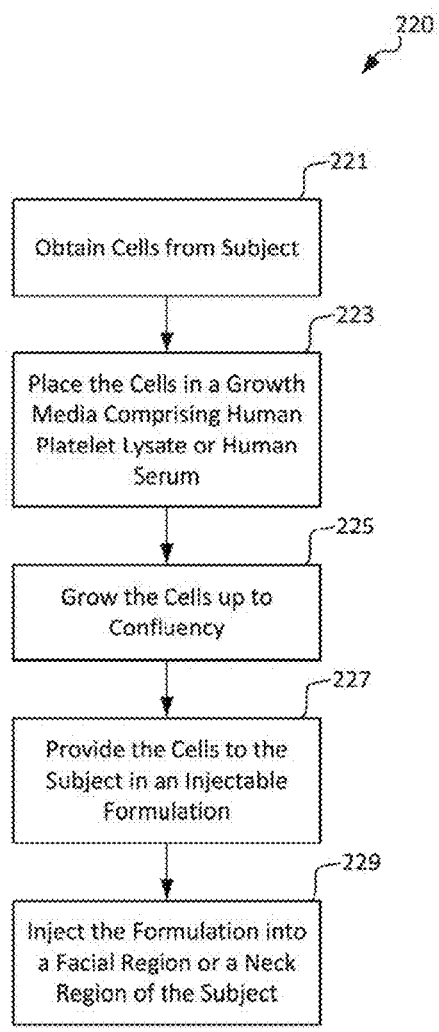

FIG. 22 shows a flow diagram of an embodiment described herein, of a method of treating skin of a subject.

Figure 23:
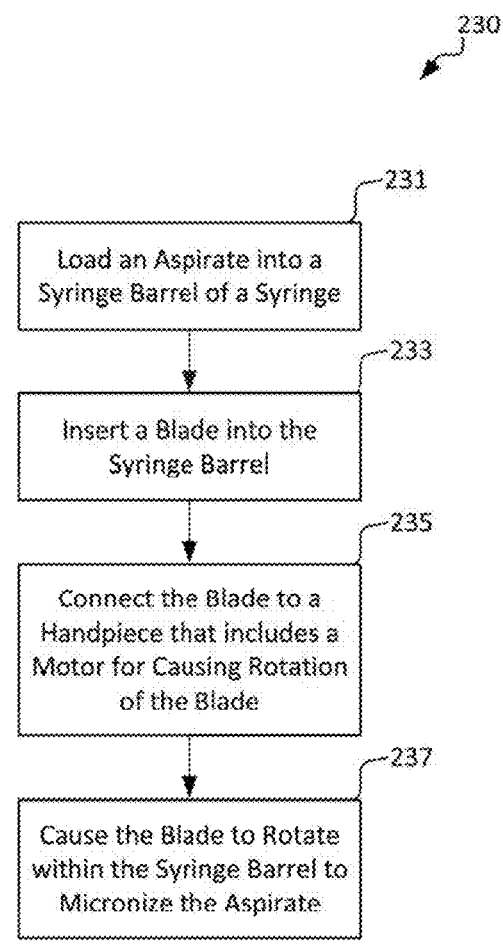

FIG. 23 shows a flow diagram of an embodiment described herein, of a method for micronizing an aspirate.

FIG. 24 shows a flow diagram of an embodiment described herein, of a method for micronizing an aspirate without the use of an enzyme.

DEFINITIONS

Unless defined otherwise, all technical and scientific terms used herein have the same meaning as commonly understood by one of ordinary skill in the art to which the disclosure pertains.

"About" as used herein when referring to a measurable value is meant to encompass variations of ±20% or ±10%, more preferably ±5%, even more preferably ±1%, and still more preferably ±0.1% from the specified value.

"Human platelet lysate" (HPL) as described herein, is a substitute supplement for fetal bovine serum in a cell culture. In some embodiments described herein, cells used for treatment are grown in culture that is supplemented with HPL.

HPL can be manufactured by a variety of means that are known to those skilled in the art. HPL can be created from single or pooled donor-donated platelets isolated from whole blood or by apheresis, distributed in a standard platelet collection bag. There are some differences between HPL manufacturing protocols, but all can share the same step of being frozen at very low temperatures and thawed. This process can be repeated two or three times to cause complete platelet lysis. The resultant HPL can then undergo different manufacturing steps to achieve multiple grades of HPL.

The most common form of HPL undergoes few processing steps, producing a product made of the supernatant following the freeze/thaw process. The included clotting factors required to add heparin to the cell culture media to prevent coagulation during incubation.

Another form of HPL is one that can be used in cell culture without the need of heparin, or any anticoagulant, addition. This grade of HPL goes through further manufacturing steps to inhibit the effect the clotting factors have.

Many labs around the world are creating small amounts of HPL to suit their laboratory needs. Large-scale manufacturing by pooling many platelet donors can be used to mitigate the donor-to-donor variability. Consistency is a top priority for experimental designs to provide reproducible results.

Human platelet lysate is commonly used for supplementation of basal media in mesenchymal stem cells culture. Prior the use, the pathogen inactivation process is recommended to prevent pathogen transmission.

Furthermore, commercially available human platelet lysate can be used, for example, such as HPL prepared commercially by Mill Creek Life Sciences, Compass Biomedical, Inc., Cook Regentec, Macopharama SA, iBiologics, PL bioscience GmbH and Trinova Biochem GmbH. Product lines can include but are not limited to PLTMax, PLUS™, Stemulate, Human Platelet Lysate, XcytePlus, $PL_{SOLUTION}$, $PL_{MATRIX}$ and CRUX RUFA Media supplements.

PLUS™ human platelet lysate which is commercially available has been used in some embodiments described herein. The PLUS™ human platelet lysate is a growth factor rich product manufactured by lysing human platelets. The serum product can be used as cell culture supplement and the lyophilized product has applications in wound healing.

The product, PLUS™ human platelet lysate, is started from raw material which is expired transfusion platelets sourced from FDA-registered and ISO-registered blood banks. The raw material inventories, which are the platelets from the blood banks, are then selected for the production initiation, in which the units are identified for thawing. The thawed pool of platelets are then pooled and transferred into a large transfer bag for serum conversion. The material is then further centrifuged and pooled in a large container for distribution into bottles or cry bags. The raw material is then tested for Human Immunodeficiency Virus I/II, Human T-Lymphotropic Virus, Hepatitis B Virus, Hepatitis C Virus, Syphilis, West Nile Virus and Trypanosoma cruzi. Testing is carried out in a CLIA certified test laboratory. After testing, the raw material is then manufactured through a GMP closed-loop production system for making of the final product, which is a liquid supplement for cell culture, lyophilized product for wound healing applications. The final product is then tested for bacterial & fungal contamination, endotoxin, mycoplasma, MSC expansion, pH, osmolality, hemoglobin, total protein and blood chemistry. The material is filter sterilized. If the material is to be made into a lyophilized powder, the serum is then sterile lyophilized. The full GMP manufacturing system is in place with incoming product inspection, employee training, SOPs, record keeping and quality control.

The final product as a serum is available as a research product for cell culture supplementation, in which it is provided in cryo-bags and bottles. A certificate of Analysis is always included with all products.

The final product as a lyophilized powder has minimal change in activity upon lyophilization/reconstitution and is stable at room temperature. The powder can be reconstituted in various solutions and gels (water, PPP, alginate). Currently, the powder is being testing for advanced wound healing applications.

The final product of PLUS™ human platelet lysate has several features and benefits for its use. For example, the human derived, growth factor rich, serum or powder supplement can support in vitro propagation of MSCs, keratinocytes, fibroblasts and other cell types. As such, the PLUS™ human platelet lysate has all the benefits of PRP without the inconvenience of needles and blood draws. Furthermore, the platelets have been sourced from FDA-registered blood banks, so that rigorous serology testing and infectious disease screenings have already been performed. Additionally the large-scale GMP manufacturing has already been established. There are over 100 donor platelet units pooled for each lot, there is consistent product with minimal lot-to-lot variation, and each lot has been tested for MSC expansion, total protein content, pH and several other parameters.

The PLUS™ human platelet lysate is considered very safe to use. The material sourced for the product has come from donors who have been stringently screened and tested for infectious diseases. The platelets are then collected and frozen immediately after a five day expiration. Other safety features include manufacturing the product within a fully closed loop system to prevent exposure to sources of potential contamination and then there is an additional rigorous testing of the final product to ensure that there are no bacterial and fungal contaminations, endotoxins and mycoplasma.

PLUS™ human platelet lysate has several deliverable options. It can be delivered as a cell culture supplement (GMP Plus™), as Plus™ lyophilized in individual packages for reconstitution with platelet poor plasma (PPP), as Plus™ lyophilized and shipped in bulk volumes of 500 mL to 1L, or as a kit with lyophilized GMP Plus™ in 10 ml sterile glass vial with a crimp seal, vial adapter and a syringe. The prices for the supplements depending on volume and product can range from $275 to $845 (for example, 250 mls of GMP Plus™ Cell Culture Supplement). For the lyophilized packages, the kits can come with the instructions for the reconstitution into a liquid formula. The typical lot sizes for GMP Plus™ are 20 liters although custom lots can be made for up to 50 liters. For consistency in lab tests, lot reservations can be made and delivery for orders for up to 10 liters are immediate.

The human platelet lysate can be formed from but not limited to platelet rich plasma (PRP), pooled platelets from humans and cultured megakaryocytes from stem cell expansion technology. In some embodiments described herein, HPL is from a commercial source. In some embodiments described herein, the human platelet lysate is prepared in the laboratory from platelet rich plasma (PRP), pooled platelets from humans or cultured megakaryocytes from stem cell expansion technology.

"Platelet rich plasma" (PRP) as described herein is a blood plasma that has been enriched with platelets. As a concentrated source of autologous platelets, PRP contains and releases through several different growth factors and other cytokines that stimulate healing of bone and soft tissue. The components of PRP can include but is not limited to platelet-derived growth factor, transforming growth factor beta, fibroblast growth factor, insulin-like growth factor 1, insulin-like growth factor 2, vascular endothelial growth factor, epidermal growth factor, Interleukin 8, keratinocyte growth factor, and connective tissue growth factor.

PRP can be prepared by collection of the patient's whole blood (that is anticoagulated with citrate dextrose) before undergoing two stages of centrifugation designed to separate the PRP aliquot from platelet-poor plasma and red blood cells. In humans, the typical baseline blood platelet count is approximately 200,000 per µL; therapeutic PRP concentrates the platelets by roughly five-fold. The PRP can then be used to prepare human platelet lysate. Differences between the use of PRP and platelet lysate can be shown in Table 1.

TABLE 1

| Human Platelet Lysate Comparison to PRP | | |
|---|---|---|
| | PRP | Platelet Lysate |
| Source | Autologous | Allogeneic |
| Availability | From patient, blood draw required | Off-the shelf |
| Composition | 6x PLT<br>3X WBC<br>Low RBC | Cell-free<br>Similar growth factor composition to PRP |
| Safety | High autologous product | High<br>Platelets from FDA-registered banks<br>Closed-loop manufacturing |
| Activity | Dependent on patient | Consistent<br>Platelet donors tend to be young and healthy |
| Performance testing | None | All lots tested with MSCs |
| Delivery to wounds | Gelation via thrombin/$CaCl_2$ | Flexible, multiple routes under investigation |

"Mesenchymal stem cells" (MSC) are fibroblast shaped cells that are capable of multigenic differentiation into the bone, fat, cartilage, hepatic and pancreatic tissue. The growth rate of MSCs have been studied when grown in media containing platelet lysate in comparison to media containing fetal calf serum (FCS) (Riordan et al. "Scalable efficient expansion of mesenchymal stem cells in xeno free media using commercially available reagents" J. Transl. Med 13:232 (2015); incorporated by reference in its entirety herein).

"Skin damage" as described herein, can refer to damage to the skin that can be caused by aging, sun damage, cancer, skin disorder or skin diseases that can cause irritation of the skin. "Without being limiting, the "skin diseases" and/or "skin disorders" can include acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriee des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and tropical acne. In some embodiments described herein, a method of treating a subject in need is provided. The subject can have acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriee des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and/or tropical acne.

"Hair and scalp disorders" are diseases that affect the hair and scalp and are also described herein. Diseases that affect hair and scalp can include but are not limited to alopecia, androgenic alopecia, hirsutism, hair shaft disorders, inflammation, acromegaly, eczema, psoriasis, impetigo, atopic dermatitis, darier disease, and folliculitis. Top causes for scalp disorders can include but is not limited to acromegaly, atopic dermatitis, darier disease, eczema, fragile X syndrome, impetigo, pachydermoperiostosis, psoriasis and Rosenthal-Kloepfer syndrome. In some embodiments described herein, a method of treating a subject in need is provided. The subject can have a disease affecting the skin and scalp. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from acromegaly, atopic dermatitis, darier disease, eczema, fragile X syndrome, impetigo, pachydermoperiostosis, psoriasis and/or Rosenthal-Kloepfer syndrome. In some embodiments, the treating includes administering a formulation to the subject in need. In some embodiments, the formulation is within a hair cream, a hair gel, a scalp lotion, a shampoo, conditioner, hair spray or a hair mousse.

"Nail diseases" are disorders or diseases that affect the nail, nail bed or cuticle region and are also described herein. Diseases that affect the nail and surrounding skin area such as the cuticle can lead to infection or inflammation that could require medical assistance. Diseases that infect the nail, nail bed and/or cuticle can include but is not limited to onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and melanonychia. In some embodiments described herein, a method of treating a subject in need is provided. The subject can have a disease affecting the nails, nail bed and/or cuticles. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and/or melanonychia. In some embodiments, the treating includes administering a formulation to the subject in need. In some embodiments, the formulation is within a skin cream, a lotion, a cuticle cream or a nail polish.

"Oral health" as described herein, refers to the health of the teeth and the surrounding tissues such as the gums. Poor oral health can arise from poor oral hygiene, tooth decay, gum disease, diabetes, pregnancy, cancer, HPV, oral cancer (squamous cell carcinoma, verrucous carcinoma, minor salivary gland carcinomas, lymphomas), benign oral cavity and oropharyngeal tumors (eosinophilic granuloma, fibroma, granular cell tumor, karatoacanthoma, leiomyoma, osteochondroma, lipoma, schwannoma, neurofibroma, papilloma, condyloma acuminatum, verruciform xanthoma, pyogenic granuloma, rhabdomyoma, odontogenic tumors), leukoplakia and erythroplakia, and tongue cancer. Cancer in the mouth can occur on and around the tongue, the gums, the roof of the mouth and in the insides of the cheeks and lips. In some embodiments, a treatment is provided for maintenance of oral health for a subject in need. In some embodiments, the subject has poor oral hygiene, tooth decay, gum disease, diabetes, cancer, HPV, oral cancer (squamous cell carcinoma, verrucous carcinoma, minor salivary gland carcinomas, lymphomas), benign oral cavity and oropharyngeal tumors (eosinophilic granuloma, fibroma, granular cell tumor, karatoacanthoma, leiomyoma, osteochondroma, lipoma, schwannoma, neurofibroma, papilloma, condyloma acuminatum, verruciform xanthoma, pyogenic granuloma, rhabdomyoma, odontogenic tumors), leukoplakia and erythroplakia or tongue cancer. In some embodiments, the subject is pregnant. In some embodiments, the treatment includes administering to the subject in need a formulation, wherein the formulation includes cells manufactured by any one of the methods described herein. In some embodiments, the formulation is in the form of a gargle or a rinse. In some embodiments, the formulation is in a gel, wherein the gel is administered in a teeth tray.

"Inflammation" as described herein, refers to a biological response of a body tissue to harmful stimuli. The harmful stimuli can include but is not limited to pathogens, bacteria, viruses, fungi, damaged cells and other irritants that are known to those skilled in the art. Inflammation can be a protective immune response that can involve, for example, immune cells, white blood cells, blood vessels, molecular mediators, and other small molecules. Signs of inflammation can include but is not limited to pain, heat, swelling, and/or loss of function. Inflammation can be acute or chronic. In some embodiments described herein, a formation is provided for the treatment of inflammation. The formulation can include cells manufactured by the methods described herein. In some embodiments, the subject suffers from inflammation. In some embodiments, the inflammation is on the skin, scalp, nasal passages, mouth, nail area such as the cuticles, eyes, vaginal area or the perineal area.

"Auditory health" can refer to the health of the ear, inner ear, outer ear and surrounding areas.

"Tear troughs" are the hollow indentations that are beneath the eye. Tear troughs can also appear due to saggy skin. Saggy skin can be caused by aging, loss of collagen and elastin underneath the skin tissues and sudden weight loss. For cosmetic purposes saggy skin is usually treated around the neck region and facial regions such as the laugh lines, tear troughs and the jaw jowls.

"Micronize" as described herein, refers to breaking of a substance into very fine particles, for example, into particles that are only a few microns in diameter. Micronizing can be performed by a micronizer (for example, as shown in FIGS. 14-19). Examples of several other types of commercial type micronizers for aspirate and organ tissue are known to those skilled in the art.

"Pharmaceutical vehicle" as described herein, refers to an inert substance with which a medication is mixed to facilitate measurement and administration of the pharmaceutical formulation. In some embodiments, a formulation for injection is provided, wherein the formulation comprises cells and a pharmaceutical vehicle.

"Dental tissue" as described herein, refers to tissue that is in the oral cavity. Without being limiting, this can include tissue from the gums, inside of the cheeks and gingivae. In some embodiments, the cell is provided, wherein the cell is selected from an aspirate, a marrow aspirate, fat aspirate, bone marrow aspirate, dental tissue and/or amnio/placental tissue. Cells from the dental tissue can thus be used for dental applications such as for use in a topical formulation for the gums, for example.

"Bone marrow aspirate," as described herein, refers to a sample containing bone marrow cells that can be obtained through a needle, for example. The technique of obtaining bone marrow is known to those of skill in the art. Bone marrow is the soft, sponge like tissue in the center of most bones. In some embodiments, the cell is selected from an aspirate, a marrow aspirate, fat aspirate, bone marrow aspirate, dental tissue and/or amnio/placental tissue.

"Growth media" or "media," as described herein, refers to a solid or liquid designed to support the growth of microorganisms or cells. Common growth media for cells, for example, are nutrient broths and agar plates; specialized media are sometimes required for cell culture growth. In the embodiments herein, the media is needed for cell culture growth and expansion. Without being limiting the growth media can be a commercially obtainable growth media that is specialized for eukaryotic cells or mammalian cells. There are several types of media. Without being limiting, this can include, nutrient media, minimal media, selective media, differential media, transport media, and enriched media. The media can be obtained commercially or can easily be manufactured by one with skill in the art. Without being limiting, the cell culture media comprises a carbon source, amino acids, vitamins, a balanced salt solution and a buffer to maintain a balanced pH in the media during cell growth. Without being limiting, commercially available nutrient media specifically for mammalian cells can be made by ThermoFisher Scientific (DMEM, IMDM, RPMI 1640, MEM, OPti-MEM medium, DMEM/F-12, GluaMax, Advanced media, Recovery freezing medium, F10 Nutrient mixture, Ham's F12 Nutrient mixture, Media 199, Opti-MEM, SensiCell Media for Sensitive cells, BME, Stem cell media (Essential 8™, StemPro™, MSC SFM media)), EMD-Millipore (Cellvento ™, Cellvento ™ BHK cell culture medium, Cellvento ™ CHO cell culture media platform, Customized Cell Culture Media, Classical Cell Culture Media), Fisher Scientific (Corning ™ cellgro ™ Minimimal Essential Medium Eagle without Glutamine, Corning ™ cellgro ™ DMEM with L-glucose and sodium pyruvate), Stemcell ™ Technologies (mTESR™ 1, Metho-Cult™ H4034 Optimim, BrainPhys™), Life Technologies, Invitrogen™ (RPMI 1640 medium) and GE Healthcare (AciCHO P). Cell media for mammalian cells can also be made by those skilled in the art. Without being limiting this can include using recipes for Ham's Medium, which contains all the amino acids, purines and pyrimidines for the synthesis of nucleotides, precursors for synthesizing phospholipids, vitamins, coenzyme lipoic acid, glucose and inorganic ions (sodium, potassium, calcium, copper, zinc and cobalt). The cell media can further be modified with growth factors and proteins. Media can also be optimized for improving cell recovery and viability of cells during a freeze-thaw step for the cells.

"Media Supplements" as described herein, are used to help mammalian cells produce proteins, and can be used to customize the growth conditions of the cells as provided herein, by improving cell viability and maintaining the growth of the cells. Without being limiting, the supplements can include amino acids, 2-mercaptoethanol, lipids, MEM vitamin solutions (commercially made or produced in a laboratory), BSA, human keratinocyte growth supplements, human melanocyte growth supplements, microvascular growth supplements, cholesterol supplements, transferrin, sodium pyruvate and/or vitamins. In some embodiments herein, a method of making a cell for treatment of a subject is provided, the method comprising obtaining cells from the subject, placing cells in growth media, wherein the growth media comprises human platelet lysate and growing the cells up to confluency. In some embodiments, the growth media comprises media supplements.

DETAILED DESCRIPTION

This disclosure provides for a method of making a cell, a cell and a topical formulation comprising a cell that is useful to provide a subject a treatment for a skin disorder or a treatment for pain. This disclosure also describes devices and systems that, in some embodiments, are used in the preparation of such a formulation.

Methods of Making a Cell for Treatment

In some embodiments, a method of preparing a cell for treatment is provided. A method of making a topical formulation for treatment for a subject is also provided. Previous methods of preparing mammalian cells involve the use of media, wherein the media contains fetal bovine serum. As shown in exemplary embodiments herein, the cells can be prepared in human platelet lysate, which led to a surprising increase in the proliferation of cells with a shorter doubling time of cells, which is more cost effective. The cells also had an increase in the expression of the protein collagen, which is known to improve the appearance of the skin. Additionally, the increase of cells can lead to a larger amount of cells to be used for treatment and to treat a larger surface area of skin on a subject in need. Human platelet lysate can be prepared for use, which is known to those skilled in the art. Furthermore, commercially available human platelet lysate can be used, for example, such as HPL prepared commercially by Mill Creek Life Sciences, Compass Biomedical, Inc., Cook Regentec, Macopharama SA, iBiologics, PL bioscience GmbH and Trinova Biochem GmbH. Product lines can include but are not limited to PLTMax, PLUS™, Stemulate, Human Platelet Lysate, XcytePlus, $PL_{SOLUTION}$, $PL_{MATRIX}$ and CRUX RUFA Media supplements.

Human platelet lysate can also be prepared for use in the embodiments described herein, and their preparation is known to those skilled in the art. The preparation of human platelet lysate is described in Schallmoser et al. (J Vis Exp. 2009 Oct 30 ;(32), Fekete et al. (Cytotherapy. 2012 May; 14 (5): 540-554) and Shih et al. (New Biotechnology Volume 32, Issue 1, 25 Jan. 2015, Pages 199-211) (each of these references, and all references cited herein, are hereby expressly included by reference in their entireties). Human platelet lysate can also be produced by use of a commercially available platelet lysate preparation kit, such as ones by Macopharma. The human platelet lysate can be comprised from but not limited to platelet rich plasma (PRP), pooled platelets from humans and cultured megakaryocytes from stem cell expansion technology.

As used herein, human platelet lysate can be a substitute supplement for fetal bovine serum in experimental as well as in clinical cell cultures. The human platelet lysate is obtained from human blood platelets after several freeze/thaw cycles, which case the platelets to lyse and release a large quantity of growth factors for cell expansion. In some embodiments, the media in which the cells are growing comprise 1%, 2%, 3%, 4%, 5%, 6%, 7%, 8%, 9%, 10%, 11%, 12%, 13%, 14% or 15% volume/volume human platelet lysate in the medium, or any amount in between any two aforementioned values.

Human platelet lysate can be manufactured from a single or a pooled donor donated platelets. In some embodiments, the human platelet lysate is manufactured from a single or a pooled donor donated platelets. In some embodiments, the human platelet lysate is manufactured from PRP or cultured megakaryocytes from stem cell expansion technology.

The method of making the cells for treatment or of making a topical formulation for treatment for a subject can include obtaining the cells from the subject in need, placing the cells in a growth media and growing the cells up to confluency. The cells can be grown in a shaker at an agitation speed comprising at least, greater than, equal to, or any number in between 100, 120, 130, 140, 150, 160, 170, 180, 190 or 200 rpm or any other speed in between any two aforementioned values. The cells can also be grown in spinner flasks or baffled flasks in order to increase oxygenation. In some embodiments, the cells can also be grown in cell culture treated flasks, dishes, multidishes and multiwall plates, and other culturing devices known to those skilled in the art. The cells can be allowed to grow at a temperature comprising at least, greater than, equal to, or any number in between 22° C., 24° C., 26° C., 28° C., 30° C., 32° C., 34° C., 36° C., 38° C. or 40° C., or any other temperature in between any two aforementioned values. In some embodiments, the cells are grown for a time comprises at least, greater than, equal to, or any number in between 1, 2, 3, 4, 5, 6, 7, 8, 9, 10, 11 or 12 hours or any amount of time defined between any two aforementioned values. In some embodiments, the cells are grown to a confluency comprising at least, greater than, equal to, or any number in between 40%, 50%, 60%, 70%, 80% or 90% confluency. In some embodiments, the media comprises human platelet lysate, platelet rich plasma (PRP) or human serum. The cells can be grown and then cryopreserved for later use, such as incorporation into a topical formulation for later treatment for the subject in need.

The cells in the described embodiments can be extracted from the patient in need of a treatment. In some embodiments, the cells are fibroblasts, and other cell sources. Without being limiting, the cell sources can comprise marrow aspirate, fat aspirate, amnio/placental tissue, and any other main source of MSCs from the patient in need. In some embodiments, the cell is selected from an aspirate, a marrow aspirate, fat aspirate, bone marrow aspirate, dental tissue and/or amnio/placental tissue In some embodiments, the cells can be extracted from an organ, such as a liver or kidney. Another source of cells can come from the oral cavity, such as the insides of the cheek.

Cells for use can include but are not limited to mesenchymal stem cells.

Cells that have been obtained in aspirate such as fat aspirate, or organ tissue such as liver or kidney can be micronized in a micronizer. In some embodiments, the micronizer includes the systems and devices shown and described with reference to FIGS. 14-19.

The culture can typically be incubated under conditions of temperature and the like that are suitable for the growth of fibroblasts, mesenchymal stem cells or skin cells. For the growth of fibroblasts, for example, the temperature will generally be at least 25 degrees Celsius, preferably at least 30° C. and less than 45° C., more preferably about 37° C. In some embodiments, the temperature for the growth of the fibroblasts is 22, 24, 26, 28, 30, 32, 34, 36, 37, 38, 39, 40, 41, 42, 43, 44, 45° C. or any other temperature between any two endpoints of any of the listed values. During the growth of the cells, the cells in the culture can go through passaging one, two, three, four or five times.

In some embodiments, the culture can further comprise antibiotics and/or antimycotics to prevent growth of bacteria and/or fungal cells in the culture. The antibiotic can be penicillin, ampicillin, chloramphenicol, actinomycin D, kanamycin, neomycin, carbenicillin, cefotaxime, polymyxin B, fosmidomycin, streptomycin, gentinomycin or other antibiotics known to those skilled in the art.

Depending on the cell type, the growth media can vary in pH, glucose concentration, growth factors, nutrients and vitamins. The growth media can vary from a pH of 5.0, 6.0, 7.0 or 8.0 or any other pH in between any two aforementioned values. Those skilled in the art will know how to adjust the pH of the media if necessary.

In some embodiments, the cell is selected from a group consisting of skin cells, fibroblasts, mesenchymal stem cells, stem cells and primary human cells. The cells can be obtained from a biopsy, for example to culture and grow fibroblast cells. In some embodiments, skin cells are obtained from the subject or patient from the skin on the neck, arms, legs, buttocks, behind the ear, stomach or back. In some embodiments, the cells can be extracted from marrow aspirate, fat aspirate, amnio/placental tissue, and any other main source of MSCs from the patient in need. In some embodiments, the cell is selected from an aspirate, a marrow aspirate, fat aspirate, bone marrow aspirate, dental tissue and/or amnio/placental tissue. In some embodiments, the cells can be extracted from an organ, such as a liver or kidney. Another source of cells can come from the oral cavity, such as the insides of the cheek.

In some embodiments, the subject suffers from a skin disorder. In some embodiments, the subject suffers from pain. The pain can come from joint pain, skin irritation, headaches, stomachaches, cancer, autoimmune disease or a genetic disorder.

In some embodiments, the pain can be derived from skin irritation, skin inflammation, systemic issues such as pain arising from joints, muscles, organs and other sites of inflammation.

In some embodiments, the subject suffers from inflammation. In some embodiments, the subject suffers from inflammation. In some embodiments, the inflammation is on the skin, scalp, nasal passages, mouth, nail area such as the cuticles, eyes, vaginal area or the perineal area.

In some embodiments, wherein the subject has a skin disorder, the skin disorder is acne, alopecia, alopecia areata, alopecia totalis, angioma, athletes foot, Bowen's disease, carbuncles, candidiasis, cellulitis, dermatitis, eczema, atopic dermatitis, contact dermatitis, seborrheoeic dermatitis, stasis dermatitis, dermatofibroma, echtima, epidermolysis bullosa, erythrasma, folliculitis, Hidradentitis suppurativa, hives, hyperhidrosis, ichthyosis, impetigo, Kaposi's sarcoma, keloid, keratoacanthoma, keratosis, keratosis pilaris, keratosis follicularis, lichen planus, melanoma, melisma, miliaria, pedifulosis, pemphigus, pityriasis rosea, pityriasis rubra pilaris, psoriasis, Raynaud's disease, ringworm, rosacea, scabies, scleroderma, sebaceous cyst, skin cancer, skin tags or shingles. In some embodiments, the subject is suffering effects of skin aging, wherein the effects of skin aging comprises wrinkling of skin, sun spots, sagging and loss of skin collagen. In some embodiments, the subject suffers from a skin disease or disorder such as acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriee des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and tropical acne.

In some embodiments, the subject in need suffers from a skin disorder or a subject having a skin disorder is selected to receive a therapeutic. In some embodiments, the therapeutic is Retin-A, hydroquinone, retinol, or an antifungal. In some embodiments, the subject in need suffers from cancer or a subject having cancer is selected to receive an anti-cancer therapy. In some embodiments, the subject is selected to receive an analgesic.

In some embodiments, the cell is transfected with a nucleic acid to express a protein for therapy prior to culturing and growing the cell to confluency.

Cells for Treatment

In some aspects, a cell is provided for treatment, wherein the cell is manufactured by any of the embodiments described herein. In some embodiments, the method for manufacturing the cell comprises obtaining cells from the subject, placing cells in growth media, the growth media comprising human platelet lysate or human serum and growing the cells up to confluency. In some embodiments, the cell is selected from a group including or consisting of skin cells, fibroblasts, mesenchymal stem cells, stem cells and primary human cells. In some embodiments, the cells are from marrow aspirate, fat aspirate, amnio/placental tissue, and any other main source of MSCs from the patient in need. In some embodiments, the cells can be extracted from an organ, such as a liver or kidney. In some embodiments, the cell is selected from an aspirate, a marrow aspirate, fat aspirate, bone marrow aspirate, dental tissue and/or amnio/placental tissue. Another source of cells can come from the oral cavity, such as the insides of the cheek. In some embodiments, the growth media comprises human platelet lysate. In some embodiments, the growth media comprises human serum. In some embodiments, the growth media comprises fibroblast differentiation media. In some embodiments, the cells are grown for a time comprising at least, greater than, equal to, or any number in between 2, 3, 4, 5, 6, 7, 8, 9 or 10 hours, or any time between any two aforementioned values. In some embodiments, the cells are grown to a confluency comprising at least, greater than, equal to, or any number in between 40%, 50%, 60%, 70%, 80% or 90%, confluency.

In some embodiments, the cells are skin cells, fibroblasts, mesenchymal stem cells, stem cells or primary human cells. In some embodiments, the cells are from marrow aspirate, fat aspirate, amnio/placental tissue, and any other main source of MSCs from the patient in need. In some embodiments, the cell is selected from an aspirate, a marrow aspirate, fat aspirate, bone marrow aspirate, dental tissue and/or amnio/placental tissue. In some embodiments, the cells can be extracted from an organ, such as a liver or kidney. Another source of cells can come from the oral cavity, such as the insides of the cheek. In some embodiments, the cells are stored as concentrates from centrifuged passages of cells. The cells can be passaged one, two, three, four or five times before being concentrated. The cells can be preserved in a variety of preservatives and then brought back for later re-culture. In some alternatives, the cells can also be stored at −85C. In some embodiments, vitrification and slow programmed freezing protocols for the cells are also contemplated. The cells stored can be re-constituted in media and can go through one, two, three, four or five passages during the culture growth.

In some embodiments, the cells are extracted from the patient in need of a treatment. In some embodiments, the cells are fibroblasts, and other cell sources. Without being limiting, the cell sources can comprise marrow aspirate, fat aspirate, amnio/placenta, and any other main source of MSCs from the patient in need. In some embodiments, the cells can be extracted from an organ, such as a liver or kidney. Another source of cells can come from the oral cavity, such as the insides of the cheek.

In some embodiments, wherein the cells are from fat aspirate, the cells are micronized prior to enrichment in the culture comprising platelet rich plasma and human platelet lysate. In some embodiments, the fat micronizer can be used with platelet rich plasma to break up the platelets into very fine particles for injection. Furthermore, the cells can also be grown up in platelet rich plasma. In some exemplary embodiments described herein, the cells from the patient used for growth in platelet rich plasma and micronized by a fat micronizer for injection into the patient. In some embodiments, the micronizer includes the systems and devices shown and described with reference to FIGS. 14-19.

Cells and Topical Formulations: Populations of Host Cells Cultured

The topical formulations described herein can comprise cells manufactured by methods provided herein. In some embodiments, the cells derived from the subject in need are fibroblasts, skin cells and/or mesenchymal stem cells. In some embodiments, the cells are from marrow aspirate, fat aspirate, amnio/placental tissue, and any other main source of MSCs from the patient in need. In some embodiments, the cell is selected from an aspirate, a marrow aspirate, fat aspirate, bone marrow aspirate, dental tissue and/or amnio/placental tissue. In some embodiments, the cells can be extracted from an organ, such as a liver or kidney. Another source of cells can come from the oral cavity, such as the insides of the cheek. The cells are then prepared in a growth media comprising human lysate serum. In some embodiments, the human platelet lysate serum is a commercially available human platelet lysate. In some alternatives, the human platelet lysate is manufactured from PRP or from expanded megakaryocytes.

In some embodiments, the fat aspirate is micronized so that it can be used in an injectable formulation. In some embodiments, the micronizer includes the systems and devices shown and described with reference to FIGS. 14-19.

The cells can be collected in accordance with well-known techniques, such as, a biopsy, for example. The cells can be taken anywhere on the subjects body. Without being limiting, the cells can be taken from the skin on the neck, arms, legs, buttocks, behind the ear, stomach, inside of their cheek or on their back. In some embodiments, the cells are extracted from marrow aspirate, fat aspirate, amnio/placental tissue, and any other main source of MSCs from the patient in need. In some embodiments, the cell is selected from an aspirate, a marrow aspirate, fat aspirate, bone marrow aspirate, dental tissue and/or amnio/placental tissue. In some embodiments, the cells are extracted from an organ, such as a liver or kidney. Another source of cells can come from the oral cavity, such as the insides of the cheek. After obtaining the cells, in vitro expansion of the desired cells can be carried out in accordance with the embodiments described herein for making the cell, known techniques or variations thereof that will be apparent to those skilled in the art.

The cell can then be used for a topical formulation for therapeutic treatments. In some embodiments a topical formulation is provided. In some embodiments, the topical formulation includes a cell made by one or more of the embodiments provided herein. In some embodiments, the topical formulation further comprises growth media. In some alternatives, the cells are washed out prior to preservation, but in general it is never fully washed out, therefore a small fraction of the media may be in the topical formulation. The cells are usually concentrated as cells only and then brought out of culture into human platelet lysate for the next run. In some embodiments, the growth media comprises human platelet lysate. In some embodiments, the growth media comprises human serum. In some embodiments, the growth media comprises fibroblast differentiation media. When the cells are stored in liquid nitrogen, they can be stored indefinitely. Cryopreserved cells can be thawed and grown in media comprising human platelet lysate.

In some embodiments, wherein the cells are extracted from marrow aspirate or fat aspirate, the cells can be micronized for injection into a specific site for a patient in need as a personalized medicine or personalized treatment. In some embodiments, the micronizer includes the systems and devices shown and described with reference to FIGS. 14-19.

The topical formulation can further comprise a pharmaceutical vehicle, wherein the pharmaceutical vehicle does not interfere with the cell function and viability. The "pharmaceutical vehicle" as described herein refers to an inert substance with which a medication is mixed to facilitate measurement and administration of the topical formulation.

In some embodiments, the active ingredients and mixtures of active ingredients can be used, for example, in topical formulations comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives and stabilizers can be provided in the topical formulation. Preservatives can be used to keep the nutrients for the skin cells from breaking down.

Topical formulations comprising the cells can be formulated and used as a liquid, lotion or a cream for topical application. Suitable ingredients in the topical formulation can include a for example, water, saline, dextrose, mannitol, lactose, lecithin, albumin, or sodium glutamate, and the like. As the cells are live, and likely secrete biological molecules that can regulate the pH, pH buffering agents can be added, for example. If desired, absorption enhancing preparations (for example, liposomes), can be utilized.

In some embodiments, the pharmaceutical vehicle is soybean, grapefruit or almond oils, or synthetic fatty acid esters, such as ethyl oleate or triglycerides, or liposomes.

Coconut oil, olive oil, sesame oil, peanut oil, and soya can be used as suspension agents or lubricants in the topical formulation.

The topical formulation including the cells can further comprise one or more solvents, at least one botanical and/or at least one emollient.

In some embodiments, the topical formulation comprises a growth factor. Growth factors can be a naturally occurring substance which can provide the ability to stimulate cell growth, proliferation, healing and cellular differentiation. Without being limiting, growth factors can include, but are not limited to EGF, PDGF, FGF, TGF-α, TGF-β, NGF, Epo, IGF-I, IGF-II, IL1 IL-1, IL-2, IL-3, IL-4, IL-5, IL-6, IL-7, IL-8, IL-9, IL-10, IL-11, IL-12, IL-13, INF, INF-3, INF-γ, TNF α, TNF-β, GM-CSF, and M-CSF. In some embodiments, the topical formulation further comprises at least one growth factor. In some embodiments, the at least one growth factor is EGF, PDGF, FGF, TGF-α, TGF-β, NGF, Epo, IGF-I, IGF-II, IL1, IL-1, IL-2, IL-3, IL-4, IL-5, IL-6, IL-7, IL-8, IL-9, IL-10, IL-11, IL-12, IL-13, INF, INF-3, INF-γ, TNF α, TNF-β, GM-CSF, and/or M-CSF. Examples of growth factors (GFs) are described in U.S. Pat. No. 8,518,879 issued Aug. 27, 2013 and U.S. Pat. No. 9,119,974 issued Sep. 1, 2015, both incorporated by reference in their entireties herein.

In some embodiments, the topical formulation can comprise at least one thickener, at least one humectant, and/or at least one preservative. Humectants can be used for their moisturizing capabilities. Without being limiting, humectants can include but are not limited to sodium PCA, nanolipid gels, glycerin, alpha-hydroxy acid, butylene glycol, propylene glycol, hexylene glycol, sorbitol, hyaluronic acid, urea, glyceryl triacetate, neoagarobiose, glycerol, xylitol, maltitol, polymeric polyols, polydextrose, quillaia, MP diol, seaweed and algae extracts and lactic acid.

In some embodiments, the topical formulation further comprises a thickener.

In some embodiments, the topical formulation further comprises at least one preservative. Without being limiting, preservatives can include benzoin resin, jojoba, vitamin E, alcohol, pnenoxytthanol, methylparaben, propylparaben, diazolidinyl urea, sorbic acid and triclosan. In some embodiments, the at least one preservative is benzoin resin, jojoba, vitamin E, alcohol, pnenoxytthanol, methylparaben, propylparaben, diazolidinyl urea, sorbic acid and/or triclosan.

Without being limiting, the formulation as described herein, can be within a lotion, a cream, a gel, a cosmetic (make-up), sunscreen or a sunblock. Make-up which can contain the formulation can include but is not limited to foundation, blush, BB cream, CC cream, foundation primer, primer, lipstick, lip gloss, eyelash primer, eyeshadow, cream eyeshadow, cream foundation, skin serum and concealer.

When methods of treating a subject is required, wherein the subject has inflammation on the scalp, the formulation can be provided in a shampoo, a conditioner, a hairspray, a mousse, a gel or a hair rinse.

When methods of treating a subject is required, wherein the subject has inflammation on the nails or surrounding cuticle region, the formulation can be provided in a gel, a lotion, a cream or a cuticle oil.

When methods of treating a subject is required, wherein the subject has inflammation nasal passages or surrounding area, the formulation can be provided as a nasal spray or nasal drops.

When methods of treating a subject is required, wherein the subject has inflammation in the mouth or oral area such the gums lip, inner cheeks or roof of the mouth, the formulation can be provided as a mouth wash, toothpaste, mouth rinse or gel/cream within a teeth tray.

When methods of treating a subject are required, wherein the subject has inflammation in the perineal area, the formulation can be provided as a suppository, cream, gel or a lotion.

When methods of treating a subject is required, wherein the subject has inflammation in the ear or surrounding areas of the ear, the formulation can be provided as medication formulated for the ears such as ear drops.

When methods of treating a subject is required, wherein the subject has inflammation in the eye or surrounding areas of the ear, the formulation can be provided as medication formulated for the ears such as eye drops, eye ointments or eye cream. In some embodiments, wherein the roots of the eyelashes are affected by inflammation, the formulation can be used in an eyelash primer, wherein the eyelash primer is administered with a mascara brush or a small brush against the lashline.

When methods of treating a subject are required, wherein the subject has inflammation of the perineal area, the formulation can be provided as a cream, gel, ointment or suppository.

When methods of treating a subject are required, wherein the subject has inflammation of the vaginal area, the formulation can be provided as a cream, gel, ointment or vaginal suppository.

Methods of Administration

Some embodiments also encompass methods for making and for administering the disclosed topical formulations. Such disclosed methods include, among others, administration through topical administration, in which the administration includes administration as an aqueous suspension, an oily preparation or the like or as a salve, ointment or the like, as deemed appropriate by those of skill in the art for bringing the compound of the disclosure into optimal contact with living tissue; and administration via controlled released formulations.

As will be readily apparent to one skilled in the art, the useful dosage to be administered will vary depending upon the age, weight size of the area to be treated, the particular ingredients employed, and the specific use for which these ingredients are employed.

Methods of Treatment

Skin, Hair and Nail Care

The embodiments provided herein can be used in the treatment of subjects in need. In an exemplary embodiment, the topical formulation and cells are used to treat spots, wrinkles, texture, pores, UV spots, brown spots, red areas of the skin as well as porphyrins. As described herein, the porphyrins are the result of dead bacteria in the skin. The measurement of porphyrins is a measure of skin improvement as it relates to the propensity for breakouts or acne in the skin.

Additionally, the embodiments described herein can be used for treatment of the nails and diseases that can affect hair health. Nail diseases can include but are not limited to paronchia, fungal infection, onychatrophia and nail psoriasis. Diseases can also be treated that affect hair health. Diseases that affect hair health can include but are not limited to alopecia, male pattern baldness (androgenic alopecia), hirsutism, hair shaft disorders, and ringworm.

In some embodiments, a method for treating a subject suffering from a skin disorder is provided. The method can comprise providing the cell of any of the embodiments described herein or the topical formulation of any of the embodiments described herein and applying the cell or topical formulation to the subject, wherein the cell or topical formulation is applied onto skin. In some embodiments, the skin disorder is selected from a group consisting of psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, and impetigo. In embodiments, the skin disorder arises from an autoimmune disorder. In some embodiments, the autoimmune disorder is Alopecia areata, autoimmune angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma or Vitiligo. In some embodiments, skin diseases and skin disorders can include acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriee des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and tropical acne.

The cells or topical formulations as described in the embodiments herein can be applied to the afflicted site 1, 2, 3 or 4 times a day. In some embodiments, the cells or topical formulation is within a serum for the skin, hair product, scalp or nail product. The cells or topical formulations in the embodiments herein can be used in a variety of personal care items such as, for example, soap, lotion, shampoo, conditioner, toner or skin cream. As needed, the product can be made into serums for skin, hair products, nail products and a variety of personal care items from soaps to shampoos. As described herein, the topical formulation can be used in perpetuity.

In treatment of the nails and cuticle region, the formulation can be a cream, gel, ointment, cuticle cream or a lotion. In a treatment for improving the health of the scalp or hair, the formulation can be within a shampoo, scalp cream or lotion, gel, spray formulation, mousse, or hair rinse.

In some aspects a method of treating a subject suffering from pain is provided. The method can include providing the cell of any of the embodiments provided herein or the topical formulation of any of the embodiments provided herein and applying the cell or topical formulation to the subject, wherein the cell or topical formulation is applied onto skin. In some embodiments, the pain is from arthritis. In some embodiments, the pain is from a disease. In some embodiments, the pain is from inflammation.

Oral Health

In some aspects a method of improving oral health is provided. Declining oral health can occur due to advancement of specific diseases or mechanical reasons as well, such as rough brushing of the teeth near the gumline, or lack in proper maintenance of the teeth and gum regions. Gum diseases can also occur as a result of improper care of diabetes, genetics, heart disease, pregnancy, Sjögren's syndrome, HIV/AIDS, dry mouth (xerostomia), oral cancer, saliva and salivary gland disorders in which the dry mouth can lead to problems with the gums and tissues, drug use, methamphetamine use, cocaine use, heroin use, smoking and chewing tobacco. Aside from rough brushing near the gumline, diseases can also cause thinning and receding of the gumline.

In some embodiments described herein, formulations described herein can be used in the treatment of the gumline or tissues within the oral cavity. The formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesenchymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media.

The formulation can be provided within toothpaste, tooth gel, a mouth rinse or a mouth wash. The administering can be performed two or three times a day. In some embodiments, the treatment is done for 1, 2, 3, 4, 5, 6, 7, 15, 21 or 28 days any number of days in between any two aforementioned values.

In some embodiments described herein, formulations described herein can be used in the treatment of the gumline or tissues within the oral cavity. In some embodiments, a method of treating a subject suffering bad oral health is provided. The method can comprise administering the formulation to the subject need, wherein the administering is performed by placing the formulation in a dental tray and applying the tray to the upper and lower set of teeth such that the gums are saturated in the formulation. In some embodiments, the trays are worn for 5, 10, 15, 20, 30, 35, 40, 56, 50, 55 or 60 minutes or any other amount of time in between two aforementioned values. In some embodiments, the administering is performed two or three times a day. In some embodiments, the treatment is done for 1, 2, 3, 4, 5, 6, 7, 15, 21 or 28 days any number of days in between any two aforementioned values. In some embodiments, the subject in need has diabetes, a genetic disease, heart disease, Sjögren's syndrome, HIV/AIDS, dry mouth (xerostomia), oral cancer, or saliva and salivary gland disorders. In some embodiments, the subject is pregnant. In some embodiments, the subject has gum disease (periodontitis).

In some embodiments, the formulation is a toothpaste, tooth gel, mouth rinse/wash or a gargle formulation. In some embodiments, the administration is performed by using a toothbrush with the toothpaste or by rinsing the mouth with the formulation.

Nasal Care

Nasal health is important as the nasal passages are used to filter air for breathing and remove dust, germs and irritants. The nasal passages also warm and moisten the air to keep the lungs and passages from drying out. The nasal passages also contain nerve cells that can help with the sense of smell as well as taste. Common problems that can affect the nose can include but are not limited to nasal polyps, nosebleeds, dry nose, dry nose and irritation caused by rhinitis, allergies, runny nose, bacterial infections and illnesses.

In some embodiments described herein, formulations described herein can be used in the treatment of the nasal passages, in which the formulation is administered to the subject in need, wherein the administering is performed by administering the formulation into the nasal pathway. The formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time in between a range between any two aforementioned values. In some embodiments, the cells are grown to 40%, 50%, 60%, 70%, 80% or 90% confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesencolhymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. In some embodiments, the administering is performed two or three times a day. In some embodiments, the treatment is done for 1, 2, 3, 4, 5, 6, 7, 15, 21 or 28 days any number of days in between a range defined by any two aforementioned values. In some embodiments, the formulation is administered as a nasal drop, a nasal spray or as a nasal rinse/wash. In some embodiments, the subject in need has to nasal polyps, nosebleeds, dry nose, dry nose and irritation caused by rhinitis, allergies, runny nose, bacterial nasal infections or illnesses that can cause dry nasal passages.

Auditory Care

Auditory care can be required when a subject has inflammation in the ear, the ear canal and the surrounding tissues. Common irritants such as bacteria, viruses, mucus and other skin conditions can lead to the inflammation of the ear. External irritations can also occur that can cause inflammation of the ear. For example, when water gets trapped in the ear canal, bacteria can spread which can then cause inflammation and pain. Inner ear inflammation can also occur following a viral infection such as flu or upper respiratory infection. The virus can then cause swelling of the balance organs leading to dizziness with or without pain during inner ear inflammation.

In some embodiments, a method of treating a subject suffering from an auditory inflammation or ear infection is provided, wherein the method comprises providing the cell of any of the embodiments described herein or the topical formulation of any of the embodiments described herein and applying the cell or topical formulation to the subject, wherein the cell or topical formulation is applied into the ear. The topical formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesenchymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. In some embodiments, the formulation is in the form of ear drops, ear wash, or ear ointment.

Vaginal Inflammation

In some embodiments, a treatment is provided to a subject wherein the subject has inflammation or discomfort in the vaginal or vulvovaginal area. Symptoms can include but are not limited to irritation and/or itching of the genital area, inflammation of the vaginal or perineal area or pain. Causes can include but are not limited to disruption of the healthy microbiota, infections, yeast, bacteria or viruses. Pathogens that can cause irritation can include but are not limited to *Gardnerella*, gonorrhea, chlamydia, *Mycoplasma*, herpes, *Campylobacter*, or *Trichomonas vaginalis*. Irritation can also occur due to effects of diabetes, birth control, bad diet, tight clothing, use of antibiotics, hormonal vaginitis due to post-menopause or postpartum, or loss of estrogen. Irritants can also from condoms, spermicides, soaps, perfumes and lubricants. Loss of estrogen or hormonal vaginitis can also lead to dryness of tissues.

In some embodiments, a topical formulation is provided, wherein the topical formulation comprises the cells made by any of the methods described by the embodiments herein or the cell of any of the embodiments described herein. The topical formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time defined by a range between any two aforementioned values. In some embodiments, the cells are grown to 40%, 50%, 60%, 70%, 80% or 90% confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesenchymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. In some embodiments, the topical formulation is in the form of a gel, cream, foam or vaginal suppository.

In some embodiments, a method of treating a subject suffering from irritation or inflammation of the vaginal area is provided, wherein the method comprises providing the cell described in any of the embodiments herein or the topical formulation of any of the embodiments described herein and applying the cell or topical formulation to the subject. In some embodiments, the formulation is in a gel, cream, lotion, foam or vaginal suppository. In some embodiments, the formulation is applied onto the vaginal and perineal area. In some embodiments, the formulation is administered as a vaginal suppository. In some embodiments, the subject is suffering from vaginal dryness. In some embodiments, the subject is suffering from a bacterial, fungal, or viral infection. In some embodiments, the subject has diabetes.

Perineal Care

In some embodiments described herein, a subject is treated for irritation of the perineal area. Irritation of the perineal area can include but is not limited to hemorrhoids, anal fissures, rectal fissures, fistulas and other types of rectal infections. Without being limiting, the causes of irritation can come from proctitis, inflammatory bowel disease, Crohn's disease, ulcerative colitis, solitary rectal ulcer, rectal carcinoma, childbirth and episiotomy.

In some embodiments, a formulation is provided for use in perineal care. The formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesenchymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. The formulation can be provided as a cream, ointment, gel or a suppository.

In some embodiments, a method of treating a subject suffering from irritation of the perineal area is provided. In some embodiments, the irritation is caused by hemorrhoids, anal fissures, rectal fissures, fistulas and other types of rectal infections, proctitis, inflammatory bowel disease, Crohn's disease, ulcerative colitis, solitary rectal ulcer, rectal carcinoma, childbirth and/or an episiotomy. The method can comprise providing the cell of any of the embodiments described herein or the topical formulation of any one of the embodiments described herein and applying the cell or topical formulation to the subject, wherein the cell or topical formulation is applied onto skin or the perineal area. In some embodiments, the formulation is provided as a suppository, wherein the administration is performed by insertion of the suppository. In some embodiments, the subject suffers from diabetes.

Ocular Care

Ocular care is necessary for those who are immunocompromised or for subjects who are exposed to bacteria and irritants on a regular basis. For example, contact users or those who suffer from allergies are known to be exposed to irritants on a regular basis. Top irritants of the eye can include but are not limited to bacteria or viruses which can lead to conjunctivitis, allergic triggers such as dust or pollen and dry eye syndrome.

In some embodiments described herein, a subject is treated for irritation of the eye and the surrounding region. Irritation of the eye area can include but is not limited to conjunctivitis, bacterial or viral infection, allergens or dry eye syndrome.

In some embodiments, a formulation is provided for use in eye care. The formulation can comprise the cells made by the methods of any of the embodiments described herein or the cell of any of the embodiments described herein. The cell can be manufactured by a method of any of the described embodiments herein. The method can comprise obtaining cells from the subject, placing cells in growth media, wherein the growth media comprises human platelet lysate or human serum and growing the cells up to confluency. In some embodiments, the cell is selected from a group consisting of skin cells, fibroblasts, mesenchymal stem cells, stem cells and primary human cells. In some embodiments, the growth media comprises human platelet lysate. In some embodiments, the growth media comprises human serum. In some embodiments, the growth media comprises fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further comprises passaging the cells 1, 2, 3, 4 or 5 times. In some embodiments, the method further comprises concentrating the cells. In some embodiments, the method further comprises cryo-freezing the cells for storage. In some embodiments, the cell is a skin cell, fibroblast, mesenchymal stem cell, stem cell or primary human cell. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. The formulation can be provided as an eye wash, an eye cream or eye drops. In some embodiments, wherein the roots of the eyelashes are affected by inflammation, the formulation can be used in an eyelash primer, wherein the eyelash primer is administered with a mascara brush or a small brush against the lashline.

In some embodiments, a method of treating a subject suffering from irritation of the eye. In some embodiments, the irritation is caused by an eye infection by bacteria or virus, allergens or from dry eye syndrome. The method can comprise providing the cell of any of the embodiments described herein or the topical formulation of any one of the embodiments described herein and applying the cell or formulation to the subject. In some embodiments, the formulation is administered as eye drops into the eye. In some embodiments, wherein the roots of the eyelashes are affected by inflammation, the formulation can be used in an eyelash primer, wherein the eyelash primer is administered with a mascara brush or a small brush against the lashline.

Human Platelet Lysate for Growth of Cells.

As described herein, the cells can be grown in PLUS™ Human Platelet Lysate. The cells can be fibroblasts, MSCs or keratinocytes. PLUS™ Human Platelet Lysate is a growth factor rich product that is manufactured from lysing human platelets and the serum product can be used as a cell culture supplement. The raw material for making the PLUS™ Human Platelet Lysate can come from expired transfusion platelets that are sourced from FDA registered blood banks. These platelets are tested from HIV-I, HIV-2, human T-lymphotropic virus, hepatitis B virus, hepatitis C virus, syphilis, West Nile Virus and Trypanosoma cruzi.

The PLUS™ Human Platelet Lysate are first received and stored from the blood banks. For initiating production, units of platelets are identified for thawing. The thawed cells are then pooled in a large transfer bag for serum conversion. The platelets are then centrifuged and the supernatant is collected and pooled in a large biocontainer. The serum is then filter sterilized and distributed within bottles and cryobags. The product is then lyophilized within sterile conditions.

There are different formulations of PLUS™ Human Platelet Lysate, a serum and a lyophilized power. The serum is available as a research product for cell culture supplementation and is provided in cryo-bags and bottles. For the lyophilized power, there is minimal change in activity upon lyophilization or reconstitutes and it is stable at room temperature. The powder can be reconstituted in various solutions and gels.

The PLUS™ Human Platelet Lysate can have many features and benefits. The serum or the lyophilized power can support in vitro propagation of MSCs, keratinocytes, fibroblasts and other cell types. The PLUS™ Human Platelet Lysate also has all the benefits of PRP without the inconvenience of needles, and as such, no blood draws are required. The platelets are also sourced from FDA registered blood banks in which there is rigorous serology testing and infectious disease screening. Furthermore, large scale GMP manufacturing is already established.

Figure 1:
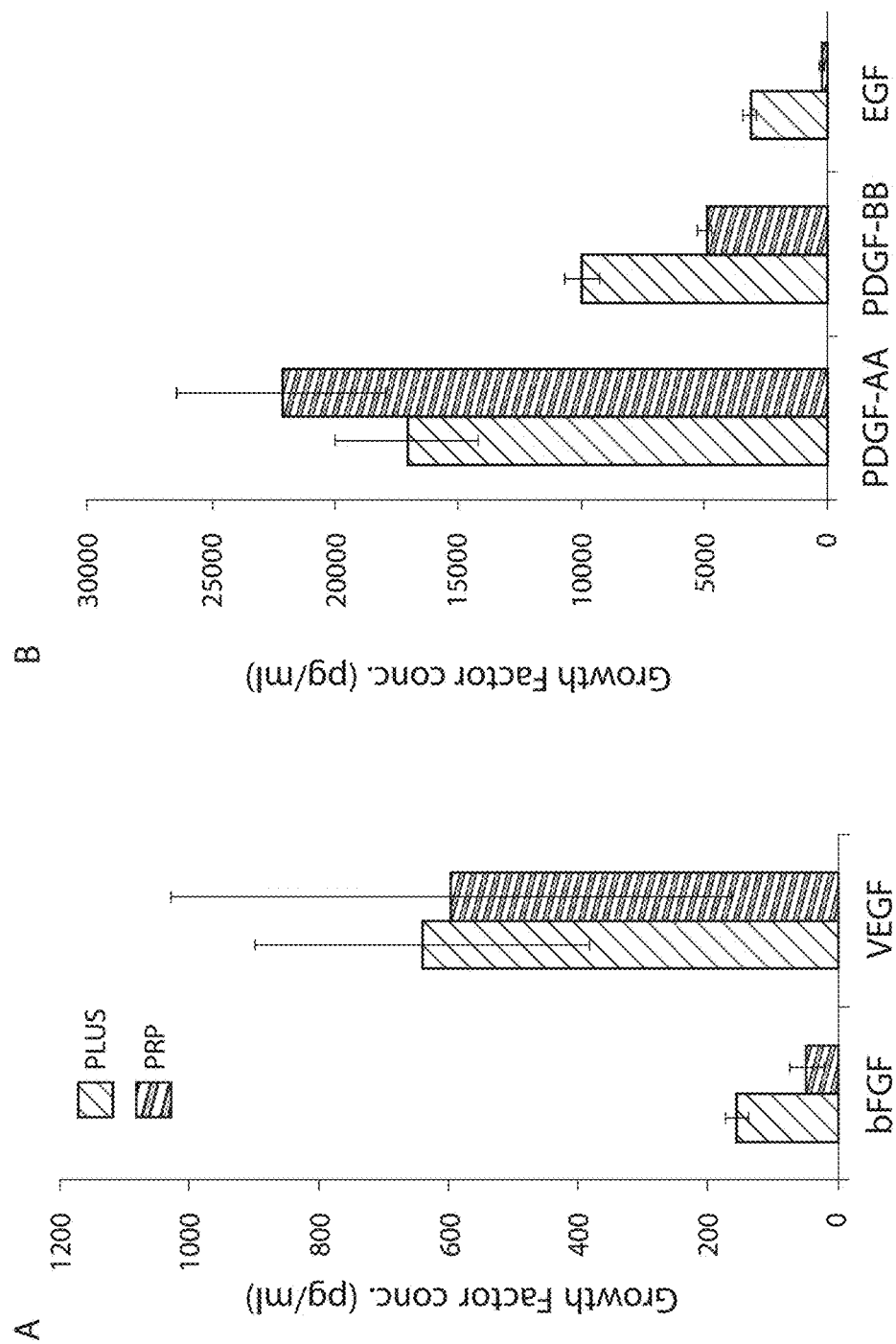
FIG. 1 (Panels A and B) shows charts demonstrating the growth factor profile of PLUS™ Human Platelet Lysate in comparison to another growth media (PRP).

In FIG. 1, it is demonstrated that PLUS™ Human Platelet Lysate has a higher concentration of growth factor such as bFGF, BEGF, PDGF-AA, PDGF-BB and EGF compared to PRP (Panels A and B).

PLUS™ Human Platelet Lysate has been shown to be safe and of high quality raw material. The platelet units are sourced from FDA registered blood banks. The platelets were taken from donors who had undergone stringent donor screening and testing for infectious diseases. The platelets were collected for transfusion and frozen immediately by 5 day expiration. The platelets for serum were then manufactured within a fully closed loop system. As such all components were sterile through the production loop to prevent exposure to sources of potential contamination. Finally, the final product had undergone rigorous testing. The final product was tested for bacterial and fungal contamination, endotoxins and mycoplasma.

PLUS™ Human Platelet Lysate is manufactured within a fully closed loop system and distributed within cryo-bags. The plasma is first taken from a pooling bag and passed through at least two filters to first remove as much precipitate. Following the first filter system the lysate is then passed through at least two sterilizing grade filters before being placed within a cryo-bag. The facility for performing the filtering is FDA and ISO registered. The testing of the serum is carried out in a CLIA certified test lab and full GMP manufacturing system is in place with incoming product inspection, employee trainings, SOPs, record keeping and quality control measures.

Figure 2:
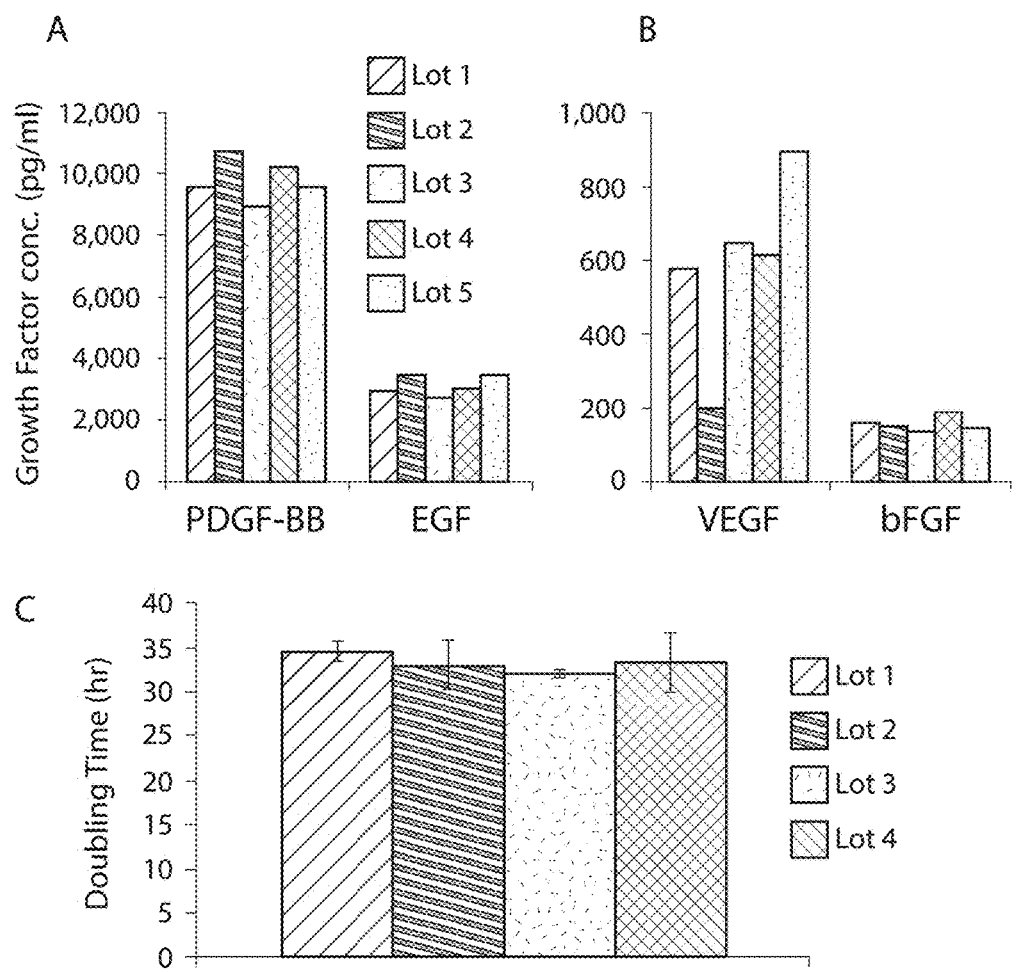
FIG. 2 (Panels A-C) shows the consistency of growth factor concentration and cell doubling times between four different lots of PLUS™ Human Platelet Lysate.

Furthermore, different lots of PLUS™ Human Platelet Lysate have been tested and have been shown to be consistent in the levels of growth factors and their doubling time of cells during growth. As shown in FIG. 2, five different lots of PLUS™ Human Platelet Lysate were shown to have similar levels of PDGF-BB, EGF, VEGF, and bFGF (FIG. 2, Panels A and B). Furthermore, MSC doubling time was similar for four lots of PLUS™ Human Platelet Lysate (FIG. 2, Panel C).

Figure 3:
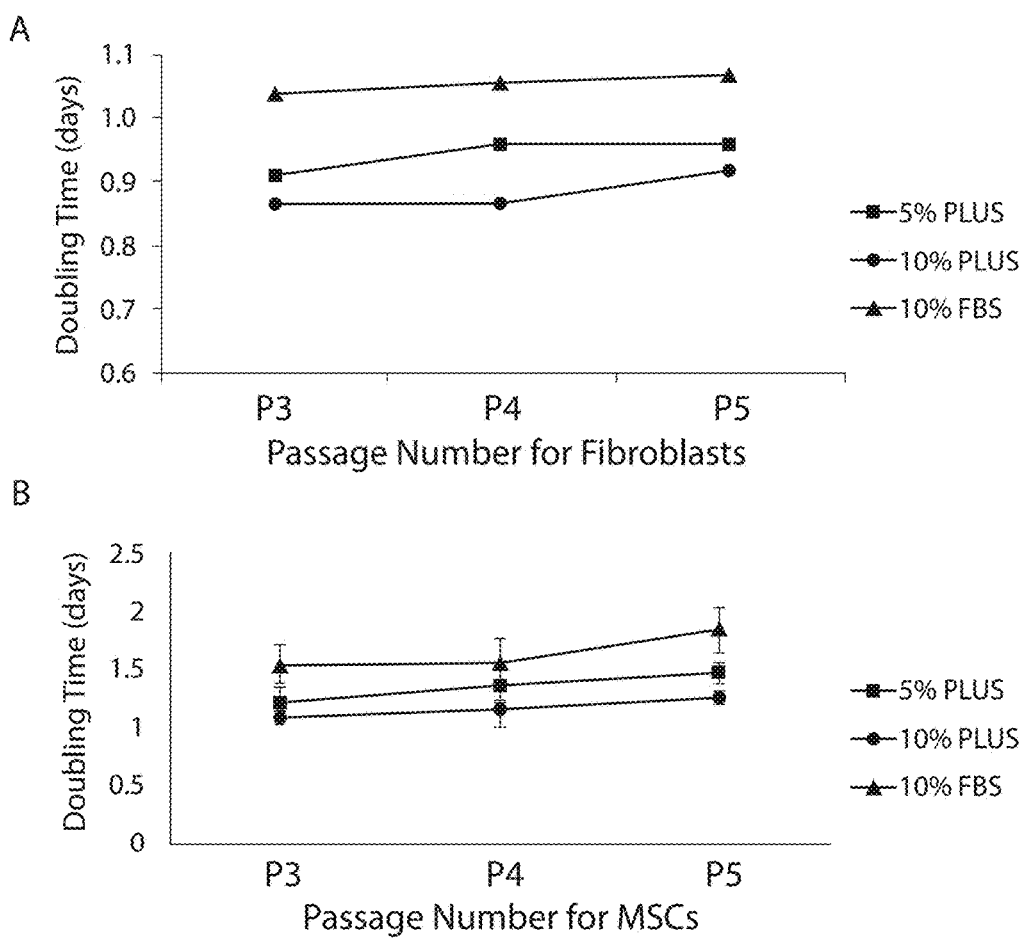
FIG. 3 shows that PLUS™ Human Platelet Lysate promotes high cell growth rates. As shown, fibroblasts (Panel A) and MSCs (Panel B) were passaged five times in which they were grown in 5% PLUS™ Human Platelet Lysate, 10% PLUS™ Human Platelet Lysate and 10% FBS.
Figure 4:
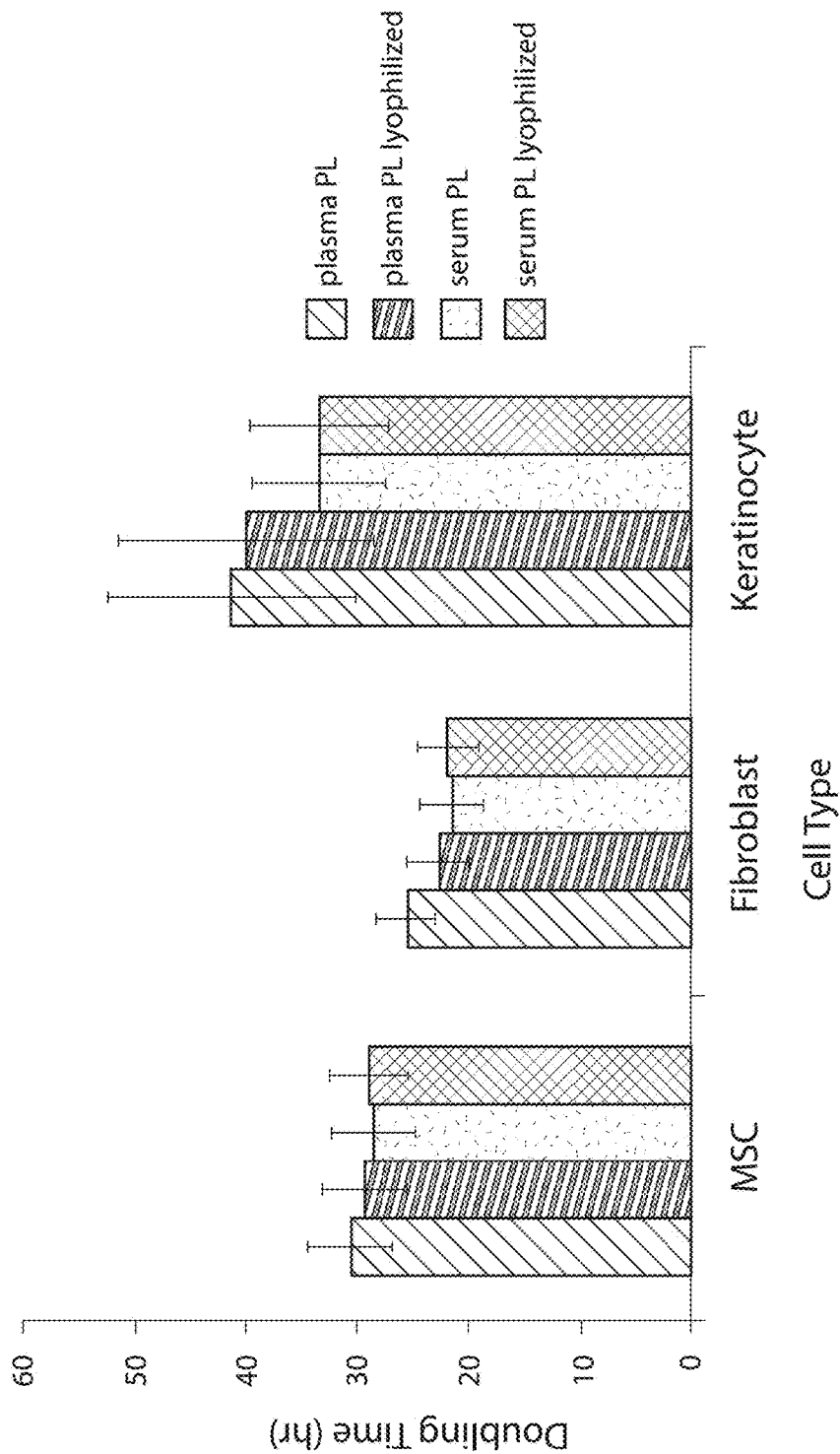
FIG. 4 shows that PLUS™ Human Platelet Lysate has no activity loss with lyophilizing. As shown MSCs, fibroblasts and keratinocytes were grown in plasma PLUS™ Human Platelet Lysate, lyophilized and reconstituted PLUS™

As shown FIG. 3, PLUS™ Human Platelet Lysate promotes high cell growth rate in fibroblasts (Panel A) and MSCs (Panel B) as compared to growth in 10% FBS. Furthermore MSCs, fibroblasts and keratinocytes were shown to equally double in reconstituted lyophilized PLUS™ Human Platelet Lysate when compared to the PLUS™ Human Platelet Lysate serum (FIG. 4). The comparison between PRP and PLUS™ Human Platelet Lysate is shown in Table 1.

Additional Embodiments
Growth of Sample Cells

Fibroblasts and mesenchymal stem cells (MSCs) for the studies were grown in 3 selected types of media. The media used were GMP PLUS™ Cell Culture Supplement, PLUS™ Lyophilized in Individual Packages for Reconstitution with Platelet Poor Plasma (PPP) and PLUS™ Lyophilized which was shipped in Bulk Volumes of 500 ml to 1 L. The prices for the media for PLUS™ cell culture supplement and GMP-PLUS™ cell culture supplement range in price depending on the type of cell culture supplement and the volume ordered. For example, the two types sold can be PLUS™ or GMP PLUS™, which can range from a 100 ml bottle to a 250 ml bottle. The prices range from $275 to $845. The GMP-PLUS™ can be supplied quickly and the media can be customized to have a specific pH, nutrient concentration and glucose concentration, which can be available within 4 weeks. The GMP-PLUS™ can then be prepared lyophilized in individual packages for use.

The lyophilized GMP-PLUS™ can then be reconstituted into a solution for growing the cells The growth and doubling time of the fibroblast cells after 5 passages of the cells is shown in FIG. 6. As shown there is an increase in cell growth when the cells were grown in 10% PLUS™ over the standard media supplemented with 10% FBS (6, top Panel A). The doubling time for the cells grown in standard media supplemented with 10% FBS was longer than the doubling time of the cells grown in 10% PLUS™, which was 1.85 days and 1.25 days, respectively. As shown in FIG. 6, Panel C, the use of 5% PLUS™ is more economical as it provides a higher density of cells in a shorter amount of time, which can easily provide more cells at a faster rate for making the topical formulations of treatment.

Growth of Fibroblasts

Neonatal human dermal fibroblasts were obtained from a human subject for growth in three different culture media of alpha-MEM medium supplemented with: 5 GMP-PLUS™, 10% GMP-PLUS™ and 10% FBS. The cells were grown in standard culture flasks. There were a total of five passages of the cells. As seen in FIG. 5, the fibroblasts grown in 10% FBS at passage 3, had a doubling time of 1.05 days and at passage 5 had a doubling time of 1.08 days. For fibroblasts grown in 10% GMP-PLUS™, the fibroblasts had a doubling time of 0.88 days at passage 3 and at passage 5 had a doubling time of 0.91 days. For cells grown in 5% GMP-PLUS™, the fibroblasts had a doubling time of 0.905 days at passage 3 and at passage 5 had a doubling time of 0.95 days. As shown, the fibroblasts proliferate faster with GMP-PLUS™. The cell proliferation fold was shown to be much larger when cultured in GMP-PLUS™ when compared to FBS (FIG. 7, Panel A). Furthermore, the cell doubling time was much shorter when cultured in alpha-MEM medium supplemented with GMP-PLUS™ instead of the FBS supplement (FIG. 7, Panel B).

Collagen Production in the Fibroblasts

Neonatal human dermal fibroblasts were obtained from a human subject for growth in three different culture media of alpha-MEM medium supplemented with: 5% GMP-PLUS™, 10% GMP-PLUS™ and 10% FBS. After 5 passages, the cells were harvested.

The fibroblasts were then washed in ice cold 0.075 M sodium citrate buffer at pH 7.0 and lysed using sonication. The collagen was then purified from the lysate. It was determined that from 10 mgs of the fibroblasts grown in media supplemented with the 10% GMP-PLUS™, the cells had 2500 picograms of collagen. Fibroblasts grown in media supplemented with 10% FBS only expressed 400 picograms of collagen. Therefore cells grown in GMP-PLUS™ had an increase in collagen production.

The fibroblast cells in general were able to produce 100 to 100 picograms of collagen per ml of growth media.

Treatment of Skin

A male and a female subject were treated with a topical formulation comprising skin cells grown in alpha-MEM medium supplemented with 10% GMP-PLUS™. The female subject was concerned about the appearance of her skin, and also had several ailments such as hip joint pain, as well as occasional headaches and migraines.

Skin cells were obtained from the female subject, and grown in the 10% GMP-PLUS™ supplemented media. After 5 passages of the cells, the cells were collected and prepared for use in a topical formulation. The topical formulation was stored for 10 days for use at a temperature of 25° C. to 30° C. The female subject used the treatment for 20 days on her face. The topical formulation was measured at 5 mls, as a liquid, and spread on her forehead, undereye area, cheeks, nose and chin at least twice a day, every day for 20 days. For the first day before application of the treatment, a VISTA facial assessment was performed. The assessment was performed on Sep. 11, 2015.

The VISIA Complexion Analysis System scanned the skin of the female subject and captured key visual information, using multi-spectral imaging and analysis, of eight areas that affect the skin's health and appearance. The assessment measured skin pigmentation, pore size, porphyrins (evidence of bacteria), UV spots, photo damage (typically from sun damage), texture and wrinkles. With this quantitative assessment of skin, the skin's features can be compared to an assessment of the skin after the treatment or even during the treatment.

As shown in FIG. 8, is the facial assessment report for the female subject before application of the topical formulation comprising the subjects skin cells. The analysis measured the subject's spots, wrinkles, texture score, pore size, UV spots, brown spots, red areas and porphyrins. The percentile scores shown in FIG. 8 for the spots (61%), wrinkles (82%), texture (97%), pores (86%), UV spots (25%), brown spots (25%), red areas (65%) and porphyrins (65%) depict the ranking to others of the same age, gender and skin types. A higher score indicates a good analysis of these eight areas.

After 20 days, on Oct., 1, 2015, a second facial assessment report on the female subject was taken. As shown in FIG. 9, several of the areas had improved following the treatment with the topical formulation. For example, the spots had diminished and the score for spots had increased from 61% to 67%. The appearance of wrinkles diminished slightly from a score of 82% to 84%. The texture of the skin did not change at all. Pore size had diminished and the score improved slightly from 86% to 91%. There was little to no improvement in the areas of UV damage as the score changed slightly from 25% to 26%. Brown spots had diminished, as the score changed from 25% to 31%. There was no improvement in the red areas of the skin. However, bacteria damage on the skin had been slightly reversed and the subject's score changed from 65% to 71% (porphyrins).

As shown in FIG. 10, is a micrograph of the cells 9 days after initial seeding (10 days after the biopsy of the female patient) (Panel A) and a micrograph of the cells at 12 days after initial seeding (13 days after the biopsy) (Panel B).

The female subject also suffered from migraines as well as hip joint pain. During the treatment of her skin, the subject also topically applied the topical formulation twice daily on the skin surrounding her hip area for twenty days. The subject noted that during the time of her treatment, the pain of her hip joint and hip flexor diminished. The subject also noted that during this time she had no occurrence of a headache or a migraine to which she is usually susceptible to. The subject also noted an improved memory and concentration as well as an overall improvement in well-being.

A male subject was also tested for use of the skin topical formulation for treatment of his skin. Skin cells were taken from the male subject and grown in alpha-MEM medium supplemented with 10% GMP-PLUS™. The male subject was concerned about the appearance of his skin.

After growth of his cells, the cells were prepared for incorporation into a topical formulation.

The male subject used the treatment for 20 days on her face, specifically the topical formulation was measured at 5 mls, as a liquid, and spread on his forehead, undereye area, cheeks, nose and chin at least twice a day, every day for 20 days. For the first day before application of the treatment, a VISIA facial assessment was performed. The assessment was performed on Sep. 11, 2015.

As done previously for the female subject, a VISIA Complexion Analysis System scanned the skin of the male subject and captured key visual information, using multispectral imaging and analysis, of eight areas that affected his skin's health and appearance. The assessment measured skin pigmentation, pore size, porphyrins (evidence of bacteria), UV spots, photo damage (typically from sun damage), texture and wrinkles. The male subject's skin's features were then documented before and after treatment with his specialized topical formulation of his own cells.

As shown in FIG. 11, is the facial assessment report for the male subject before application of the topical formulation comprising the subject's skin cells. The analysis measured the subject's spots, wrinkles, texture score, pore size, UV spots, brown spots, red areas and porphyrins. The percentile scores shown in FIG. 11 for the spots (77%), wrinkles (11%), texture (73%), pores (68%), UV spots (49%), brown spots (89%), red areas (59%) and porphyrins (67%) depict the ranking to others of the same age, gender and skin types. A higher score indicates a good analysis of these eight areas.

After 20 days, on Oct., 1, 2015, a second facial assessment report on the male subject was taken. As shown in FIG. 12, several of the areas had improved following the treatment with the topical formulation. For example, the spots had diminished and the score for spots had increased from 77% to 86%. The appearance of wrinkles improved greatly from a score of 11% to 66%. In comparison to the previous female subject whose texture of the skin did not change at all, the male subject's skin texture improved from a score of 73% to 86%. Pore size had diminished and the score improved slightly from 68% to 78%. There was slight improvement in the areas of UV damage as the score changed from 49% to 53%. Brown spots had diminished, as the score changed from 89% to 98%. There was also improvement in the red areas of the skin as the surface areas containing the red areas diminished and the subject had a score change from 59% to 78%. However, the bacteria damage on the skin increased and the subject's score changed from 67% to 60% (porphyrins).

As shown in FIG. 13, is a micrograph of the cells 9 days after initial seeding (10 days after the biopsy of the male patient) (Panel A) and a micrograph of the cells at 12 days after initial seeding (13 days after the biopsy (Panel B).

Overall, for the female and male subject, there was improvement in most areas of the study that was seen after 20 days of the treatment.

Cells Customized for Treatment of the Skin

Cells and topical formulations can also be customized for treatment of the skin. Furthermore the treatments can also be customized. In some embodiments, the cells can be at a higher concentration in order to increase the number of cells on the skin to treat areas of damage.

The cell can be manufactured by a method of any one of the described embodiments herein. The method can include, for example, obtaining cells from the subject, placing cells in growth media, wherein the growth media includes human platelet lysate or human serum and growing the cells up to confluency. In some embodiments, the cell is selected from skin cells, fibroblasts, mesenchymal stem cells, stem cells and primary human cells. In some embodiments, the cell is from an aspirate, a marrow aspirate, fat aspirate and/or amnio/placenta. In some embodiments, the cell is selected from an organ extract, such as a liver or a kidney. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the cell is from an aspirate, a marrow aspirate, fat aspirate and/or amnio/placenta. In some embodiments, the cell is selected from an organ extract, such as a liver or a kidney.

Prior to growth of the cell in media supplemented with human platelet lysate or human serum, the cells can also be transfected with a nucleic acid comprising a gene encoding a protein of interest. The gene can be under control of a regulatory element or under the control of a prodrug, in order to express a protein of interest when necessary.

In some methods of treatment, wherein a subject is selected to be treated with a topical formulation comprising cells from the subject, the subject can also be selected to be treated with an additional drug or topical formulation. In some embodiments, the subject is already receiving a prescription drug for treatment of their skin. In some embodiments, the drug is tretinoin. In some embodiments, the drug is hydroquinone. In some embodiments, the subject suffers from sun damage. In some embodiments, the subject suffers from a first degree burn. In some embodiments, the subject suffers from a second degree burn.

Topical Formulation

In some embodiments, a topical formulation is provided wherein the topical formulation comprises the cell of any one of the embodiments described herein or the cell manufactured by any one or more of the embodiments described herein. In some embodiments, the topical formulation further comprises a nutrient for the cell. In some embodiments, the topical formulation further comprises growth media. In some embodiments, the growth media comprises human platelet lysate. In some embodiments, the growth media comprises human serum. In some embodiments, the growth media comprises fibroblast differentiation media. In some embodiments, the topical formulation is partially prepared using the systems and devices described below with reference to FIGS. 14-19.

Specialized Cells for Injection, Formulations for Injection

In some embodiments, the cells are extracted from the patient in need of a treatment. In some embodiments, the cells are fibroblasts, and other cell sources. Without being limiting, the cell sources can comprise marrow aspirate, fat aspirate, amnio/placenta, and any other main source of MSCs from the patient in need. In some embodiments, the cells can be extracted from an organ, such as a liver or kidney. Another source of cells can come from the oral cavity, such as the insides of the cheek.

In some embodiments, wherein the cells are from fat aspirate, the cells are micronized prior to enrichment in the culture comprising platelet rich plasma and human platelet lysate. In some embodiments, the fat micronizer (for example, the devices and systems described with reference to FIGS. 14-19. can be used with platelet rich plasma to break up the platelets into very fine particles for injection. Furthermore, the cells can also be grown up in platelet rich plasma. In some exemplary embodiments described herein, the cells from the patient used for growth in platelet rich plasma and micronized by a fat micronizer for injection into the patient. In some embodiments, the micronizer includes the systems and devices shown and described with reference to FIGS. 14-19.

Pharmaceutical formulations of the cells can be formulated and used as suspensions for injectable administration. Injectables can be prepared in conventional forms, either as liquid solutions or suspensions, solid forms suitable for solution or suspension in liquid prior to injection, or as emulsions. Pharmaceutical formulations for injection may also include suitable excipients. Suitable excipients are, for example, water, saline, dextrose, mannitol, lactose, lecithin, albumin, sodium glutamate, cysteine hydrochloride, and the like. In addition, if desired, the injectable pharmaceutical formulations can contain minor amounts of nontoxic auxiliary substances, such as wetting agents, pH buffering agents, and the like. If desired, absorption enhancing preparations (for example, liposomes), can be utilized.

For injection, the agents of the disclosure can be formulated in aqueous solutions, preferably in physiologically compatible buffers such as Hanks' solution, Ringer's solution, or physiological saline buffer. Additionally, suspensions of the active ingredients can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents that increase the solubility of the ingredients to allow for the preparation of highly concentrated solutions. In some embodiments, of the pharmaceutical formulations, the vehicle is a lipophilic solvent, fatty oil, organic oil, or liposome. In some embodiments, the vehicle is sesame oil, soybean, grapefruit or almond oils, or synthetic fatty acid esters, such as ethyl oleate or triglycerides, or liposomes.

The fat aspirate containing the cells for injection can be micronized for injection so that the fat can be emulsified in order to help inject it into small areas such as the face and neck. Without being limiting, this can be used, for example with fat from a liposuction technique from a patient and then used again on the same patient for a live personalized cosmeceutical. Micronizing can also be performed with platelet rich plasma. In some embodiments, the micronizing is performed at least partially with the systems and devices shown and described with reference to FIGS. 14-19.

Method of Treating a Region of Skin with the Injectable Formulation

A method of treating a patient with their own cells is provided. The method can comprise using the patient's own fat from their own liposuction and harvesting the cells from the liposuction in order to make an injectable formulation. The fat from the liposuction can come from any portion of the patient's body such as the thighs, buttocks, back and abdomen, for example. This can then be used to make a live personalized cosmeceutical. The cells can be grown up in a media containing platelet rich plasma and then placed in a formulation for injection. The fat can be micronized before or after it is placed in the media containing platelet rich plasma to help emulsify the fat for injection. In some embodiments, the fat is micronized with the systems and devices shown and described with reference to FIGS. 14-19. The formulation can then be used to inject into areas on the face that have lost volume such as the tear troughs or the laugh lines of the patient. The fat can be injected into the skin with a microneedling device. Those skilled in the art appreciate that there are many techniques for injection into the skin for cosmeceutical purposes.

Use of a Fat Micronizing Machine

Fat micronizing machines can be used to break up fat into very fine particles. The fat micronizer can be used to emulsify fat to help inject it into small areas on the face. However the micronization technology uses fat (fat cells) from a patient's liposuction procedure and making a live personalized cosmeceutical for the patient. In some embodiments, the fat micronizer can be used with platelet rich plasma to break up the platelets into very fine particles for injection. Furthermore, the cells can also be grown up in platelet rich plasma. In some exemplary embodiments described herein, the cells from the patient used for growth in platelet rich plasma and micronized by a fat micronizer for injection into the patient. Embodiments of fat micronizing machines are described below with reference to FIGS. 14-19.

Skin Biopsy for Cells

A skin biopsy can be performed to examine cells for use in a formulation. Skin cells can then be collected from the biopsy and grown in media with human platelet lysate and then harvested. The cells can then be banked for product development. Additionally, fibroblasts can be examined from a biopsy, then collected from the biopsy, grown in media with human platelet lysate and then harvested. The fibroblasts can then be banked for future product development. Collecting the cells, and storing by cryo technology is well known to those skilled in the art.

Liposuction Aspirate and Cell Aspirates to Live Cosmetic at the Point of Care.

In some embodiments, cells are sent to culture in HPL and expansion products made. The cells can be banked for future product development. The cells can come from liposuction aspirate to be used on the same subject from where the cells originated. In some embodiments, the cells can be used as a live cosmetic care for the subject. The sourcing can be performed from skin biopsies, for example, for amnion cells, there are 6 million children who have cord blood banked, and for marrow the TRUPRP system can be used to harvest cells. In some embodiments, for live cosmeceuticals, the source can be obtained from fat. As such, fat from liposuction that is otherwise thrown away can be used to make a product.

Embodiments of Devices and Systems for Micronizing an Aspirate

Embodiments of devices and systems for micronizing an aspirate, such as, for example, fat from liposuction, are shown FIGS. 14-19 and described below. In some embodiments, the systems and devices allow for liquefying fat in a liposuction syringe. In some embodiments, the systems and devices allow for further SVF expansion with the incubator and the use of some collagenases/lecithins. As such, the fat can be sent to the tissue bank and using HPL, the fat cells can be expanded for future products (refills) from the same liposuction isolate that is used for live products.

Devices and systems for micronizing an aspirate are described herein. The devices and systems can be used to micronize an aspirate in order to prepare a live cell formulation for the treatment of skin. In some embodiments, the aspirate may comprise a fat aspirate, such as removed from a patient during liposuction, a marrow aspirate, amnio/placental tissue, organ tissue, such as liver or kidney tissue, or platelet rich plasma, for example. In some embodiments, the cell is selected from an aspirate, a marrow aspirate, fat aspirate, bone marrow aspirate, dental tissue and/or amnio/placental tissue. The devices and systems can micronize the aspirate such that it can be used in an injectable or topical formulation (for example, a cosmeceutical) for treatment of a patient. As used herein, the term "micronize" refers to breaking, blending, or otherwise dividing a substance (for example, an aspirate) into very fine particles. In some embodiments, micronizing breaks a substance into particles that are only a few microns in diameter, although this need not be the case in all embodiments. Further, in some embodiments, the term micronize can signify emulsify or liquefy. Thus, reference in this disclosure to devices and systems for micronizing an aspirate are intended to refer to devices and systems that micronize, emulsify, and/or liquefy the aspirate into very fine particles. The particles may be a few microns in diameter or, in some embodiments, larger.

In some embodiments, the formulation prepared from the micronized aspirate can be used for treatment of the same patient from whom the aspirate was obtained. As described throughout this application, treatment of a patient with a formulation comprising live cells obtained from the patient has been shown to be beneficial for treatment of skin diseases, pain, inflammation, and other purposes. Thus, the devices and systems described herein can be useful in preparing a live personalized cosmeceutical for a patient. The cosmeceutical is referred to as personalized because it is prepared from the patient's own cells.

As mentioned above, in some embodiments, the aspirate to be micronized by the systems and devices described herein is a fat aspirate obtained from a patient during liposuction. The fat aspirate can come from any portion of the patient's body, such as the thighs, buttocks, back, or abdomen, for example. Historically, fat aspirate obtained during liposuction is discarded. However, rather than discarding the fat aspirate, the systems and devices described herein, micronize the fat aspirate in preparation of a live cell formulation.

The fat aspirate can be obtained using any type of liposuction. In some embodiments, the fat aspirate can be obtained with a liposuction syringe. In some embodiments, the systems and devices described herein can be connected to the syringe barrel of a liposuction syringe containing the fat aspirate such that the fat aspirate can be micronized while within the syringe barrel. In some embodiments, fat aspirate obtained through other methods can be loaded into a syringe, and the systems and devices described herein can then be connected to the syringe barrel such that the fat aspirate can be micronized while within the syringe barrel.

In some embodiments, the devices and systems for micronizing an aspirate can be used at the time and location of a liposuction procedure. Thus, in some embodiments, fat aspirate can be micronized shortly after it is removed from a patient. For example, in some embodiments, a patient undergoing a liposuction procedure can be provided with a live personalized cosmeceutical prepared from his or her own fat aspirate shortly after the liposuction procedure. Liposuction may be performed, for example, at localized fat deposits of the thighs, hips, buttocks, abdomen, waist, upper arms, back, inner knee, chest area, cheeks, chin, neck, calves and ankles.

A method for micronizing an aspirate is provided herein, the method can comprise the steps of loading an aspirate into a syringe barrel of a syringe, inserting a blade into the syringe barrel, connecting the blade to a handpiece, the handpiece including a motor for causing rotation of the blade, causing the blade to rotate within the syringe barrel to micronize the aspirate. In some embodiments, loading an aspirate comprises withdrawing a plunger of the syringe. In some embodiments, the method further comprises the plunger from the syringe barrel after loading the aspirate into the syringe barrel. In some embodiments, the method further comprises sealing an open end of the syringe barrel with an end cap. In some embodiments, a drive shaft extends through the end cap between the blade and the handpiece.

In some embodiments, causing the blade to rotate comprises pressing a pedal. In some embodiments, the method further comprises moving the handpiece relative to the syringe barrel to move the blade through the aspirate. A diagram of the method is shown in FIG. 23.

In some embodiments, the micronized aspirate is used to prepare a topical formulation. In some embodiments, the micronized aspirate is used to prepare an injectable formulation. In some embodiments, the injectable formulation can be injected into the skin of the patient with a micro-needling device. Those skilled in the art will appreciate that there are many techniques for injecting a cosmeceutical into the skin for treatment purposes.

The use of the device as described herein, allows the preparation of fat aspirate for use without the addition of enzymes, for example, collagenase or elastase. In order to obtain the pure fats from the aspirate, previously enzymes to break down the bonds of proteins in the aspirate have been added. However, the addition of enzymes may lead to the breakdown of the product for use in a skin cosmeceutical. As such, the use of the said device can lead to ready to use fat aspirate for formulating into a pharmaceutical.

Preparation without the use of enzymes to break down the collagen and connective tissue has the advantage of eliminating a purification step which can lead to loss of product and the cells. Furthermore, when the purified product is not 100% pure or free from any enzyme, this can lead to the breakdown of the product or cosmeceutical. Additionally, the residual enzyme in a product used for treatment may cause harm to a subject, as the enzymes are known to break down protein bonds such as the bonds within collagen, for example. As such the micronizing can be performed with the device described herein, without the use of enzymes. Enzymes for breaking the collagen and fibrous connective tissue are known to those skilled in the art. Without being limiting, these enzymes can include collagenase and elastase, for example. Thus, in some embodiments, the method of micronizing an aspirate is performed without the use of an enzyme.

A method for micronizing an aspirate is provided herein. The method comprises loading an aspirate into a container, inserting a blade into the container, connecting the blade to a motor for causing rotation of the blade, causing the blade to rotate within the syringe barrel to micronize the aspirate, wherein the aspirate is micronized without use of an enzyme. In some embodiments, the container is a syringe barrel of a syringe. In some embodiments, loading an aspirate comprises withdrawing a plunger of the syringe. In some embodiments, the method further comprises the plunger from the syringe barrel after loading the aspirate into the syringe barrel. In some embodiments, the method further comprises sealing an open end of the syringe barrel with an end cap. In some embodiments, a drive shaft extends through the end cap between the blade and the handpiece. In some embodiments, causing the blade to rotate comprises pressing a pedal. In some embodiments, the method further comprises moving a handpiece relative to the syringe barrel to move the blade through the aspirate. In some embodiments, the enzyme is collagenase. In some embodiments, the enzyme is elastase. In some embodiments, the enzyme is for breaking up connective tissue. Enzymes that are known to break up collagen and connective tissue are known to those skilled in the art. The container micronizing the fat can also be a re-usable, sterilizable fat transfer bottle or any container that is sterile. Those skilled in the art would appreciate the need to use a sterilizable container for the storage and micronization for the aspirate. A diagram of the method is shown in FIG. 24.

FIG. 14 is a block diagram illustrating one embodiment of a system 100 for micronizing an aspirate. The system 100 includes a handpiece 110, a control box 170, and a pedal 190. The handpiece 110 is connected to the control box 170 by a handpiece cable 107. The pedal 190 is connected to the control box 170 by a pedal cable 109.

The handpiece 110 includes a handle 112. In the illustrated embodiment, a motor 120 is disposed within the handle 112. In some embodiments, the motor 120 is a DC motor. In some embodiments, the motor 120 is an AC motor. In some embodiments, the motor 120 is a micro-motor. In some embodiments, the motor 120 is configured to rotate at least about 1,500 RPM, at least about 5,000 RPM, at least about 10,000 RPM, at least about 25,000 RPM, at least about 40,000 RPM or at least about 50,000 RPM. In some embodiments, the motor 120 is configured to rotate at between about 1,500 and 50,000 RPM, between about 5,000 RPM and 40,000 RPM, between about 10,000 and 25,000 RPM, or at about 20,000 RPM, although other speeds (faster and slower) are possible. In some embodiments, the speed of the motor 120 can be varied over a range. For example, in some embodiments, a user can control and/or select the speed of the motor 120. As will be described below, the rotational speed of the motor 120 can be configured to be adjustable or variable and can be adjusted by an operator. A drive shaft 130 extends from the motor 120 and out through the handle 112. The motor 120 is configured to cause rotation of the drive shaft 130. The drive shaft 130 is also connected to a blade 140. Rotational motion of the drive shaft 130, caused by the motor 120, is thus imparted to the blade 140.

In some embodiments, the motor 120 is configured to rotate at 1,500 RPM, at least about 5,000 RPM, at 10,000 RPM, at 25,000 RPM, at 40,000 RPM or at 50,000 RPM or any other speed in between a range defined by any two aforementioned values. As shown in the illustrated embodiment, the blade 140 can be positioned within a syringe barrel 150 of a syringe. In some embodiments, the syringe is a liposuction syringe. In some embodiments, the syringe is a 60 cc syringe. In some embodiments, other types of syringes can be used. The syringe barrel 150 also contains the aspirate to be micronized. Thus, rotation of the blade 140 within the syringe barrel 150 is configured to micronize the aspirate.

To contain the aspirate within the syringe barrel 150, an end cap 152 is provided to seal an open end of the syringe barrel 150. The drive shaft 130 extends through the end cap 152, such that a first portion of the drive shaft 130 is internal to the syringe barrel 150 and a second portion of the drive shaft 130 is external to the syringe barrel 150. The internal portion of the drive shaft 130 is connected to the blade 140, and the external portion of the drive shaft 130 is connected to the motor 120. In some embodiments, the drive shaft 130 extends through an opening in the end cap 152. In some embodiments, the opening in the end cap 152 and the drive shaft 130 can be configured to provide a seal at the location where the drive shaft 130 extends through the opening in the end cap 152. The seal can be configured to substantially retain the aspirate within the syringe barrel 150.

In some embodiments, the drive shaft 130 comprises a length that is approximately equal to a length of the syringe barrel 150. In some embodiments, the length of the drive shaft 130 is longer than the length of the syringe barrel 150. For example, the length of the drive shaft 130 may be approximately 105%, 110%, 115%, 120%, or 120% the length of the syringe barrel 150, or longer. In some embodiments, the length of the drive shaft 130 is shorter than the length of the syringe barrel 150. For example, in some embodiments, the length of the drive shaft 130 is approximately 95%, 90%, 85%, 80%, 75%, 50%, or 25%, the length of the syringe barrel 150, or shorter.

In some embodiments, the drive shaft 130 is configured to slidingly engage with the end cap 152, such that drive shaft 130 can slide back and forth through the opening in the end cap 152. This can allow the position of the blade 140 within the syringe barrel 150 to be adjusted and varied. For example, an operator can adjust the position of the blade 140 within the syringe barrel 150 by adjusting the position of the handle 112 relative to the syringe barrel 150. In this way, the blade 140 can be moved through the interior of the syringe barrel 150 along its length. In some embodiments, however, the position of the endcap 152 on the drive shaft 130 can be substantially fixed, and thus, the position of the blade 140 within the syringe barrel 150 can also be substantially fixed.

In the illustrated embodiment, a control box 170 is provided that is configured to control operation of the handpiece 110. The control box 170 includes a motor controller 181. The motor controller 181 is configured to control the performance of the motor 120 of the handpiece 110. For example, the motor controller can be configured to control the starting and or stopping of the motor 120, the direction of rotation of the motor 120 (for example, either forward rotation or reverse rotation), the speed of rotation of the motor 120, and/or the torque of the motor 120.

In some embodiments, the motor controller 181 controls performance of the motor 120 based on operating parameters received from an operator. Operating parameters can include, motor speed, variable speed profiles (e.g., varying speeds, speeds that ramp up, speeds that ramp down, etc.), motor direction, and time, among others. In some embodiments, the parameters of the system 100 are user dependent (e.g., selectable by the user). In some embodiments, the aspirate is spun or micronized for any length of time. In some embodiments, the aspirate is spun or micronized for at least about 15 seconds, at least about 30 seconds, at least bout 45 seconds, at least about a 1 minute, at least about 1 minute and 15 seconds, at least about 1 minutes and 30 seconds, at least about 1 minutes and 45 seconds, at least about 2 minutes, at least about 3 minutes, at least about 4 minutes, at least about 5 minutes, or longer. In some embodiments, it may take at least a minute to get the liquefaction or micronization of the aspirate. The motor 120 can spin forwards or backwards. The operating parameters can include motor speed and duration, among others. To this end, the control box 170 may include one or more inputs 172 for receiving operating parameters from the operator. The inputs 172 may include, for example, buttons, switches, dials, or other types of inputs. In some embodiments, the inputs 172 include an on/off input, speed adjustment inputs, torque adjustment inputs, or inputs providing and controlling other functions of the system 100. As will be described below, the system 100 can also include a pedal 190 that is connected to the control box 170. The pedal 190 can be used to provide additional operator input to the motor controller 181. In some embodiments, the inputs 172 allow for selection of motor speed based on a scale. For example, the scale may be a numerical scale between 1 and 5. Level 1 may represent the slowest motor speed and each subsequent level may represent a higher speed until level 5, which represents the highest speed. Other scales are possible. In some embodiments, the input 172 allows the user to select a desired speed level. In some embodiments, each press of the pedal 190 (discussed below) advances the motor speed to the next level (either to a higher or lower level).

"Emulsification," as described herein can refer to a mixture of two or more liquids that are normally immiscible. In some embodiments, emulsifying of the fats is performed. In some embodiments, emulsifying comprises centrifuging the fat, straining the fat and placing the fat in a product base, such as, for example, a cream or a media. Emulsifying a fat can also be performed by applying heat in order to place the fat in a liquid state, in which the fat can easily be placed into a cosmetic base, such as a cream or a lotion. Emulsifying is complete once the product looks homogeneous and without visible clumps or strands.

The control box 170 can also include a display 171. The display 171 can be configured to display information (such as the settings for the motor (e.g., direction, speed, etc.) or duration of operation, etc.) regarding the system 100 to the operator. For example, in some embodiments, the display 171 is configured to display the current rotational speed and/or torque of the motor 120. In another embodiment, the display 171 is configured to display an operating rotational speed and/or torque of the motor 120 as selected by the operator. In some embodiments, the display 171 is configured to display an operating time. For example, in some embodiments, the operating time can include the total time that the system 100 has been used to micronize an aspirate, including for example. In some embodiments, the operating time can be a countdown indicating for how long an aspirate should be processed to sufficiently micronize the aspirate. In some embodiments, the display 171 shows the settings for the motor 120 (e.g., spend and/or duration, or others). In some embodiments, a user can preset the motor 120 to the speed on a scale. For example, in some embodiments, the system 100 can be configured so that a motor speed of 20,000 RPM corresponds to a speed setting 5, the remaining speed settings can be 5,000 RPM increments, for example, speed setting 4 can be 15,000 RPM, speed setting 3 can be 10,000 RPM, etc. In some embodiments, the motor 120 can be turned on to the maximum RPM, or the speed can be adjusted by, for example, using the foot pedal 190 (described below). In some embodiments, a user can use the pedal to increase or decrease the motor speed between the maximum and minimum speed settings (or to stop the motor from spinning entirely). As one example, if you system 100 is set at speed level 2, and level 2 is 10,000 RPM, the pedal 190 can be configured for an incremental increase to that RPM with each press (for example, from 10,000 RPM (level 2) to 15,000 RPM (level 3). In some embodiments, the display 171 may display the motor speed as a number on the display 171 that corresponds to the speed level (e.g., 1, 2, 3, 4, 5, etc.). In some embodiments, the display 171 may show an "RPM Meter" like in a car to see show spin rate (motor speed).

The control box 170 can also include one or more processors 183 and on or more memories 185. The processors 183 and memory 185 may be configured to operate together to control operation of the system 100. For example, in one embodiment, the memory 185 may store an operating system for the control box 170 and the operating system may be executed by the processor 183. In some embodiments, the memory 185 can store one or more micronization programs. A micronization program can include a protocol for operating the motor controller 181. A protocol can specify operational parameters for operating the motor 120. For example, a protocol can specify that the motor should be operated a first speed for a first length of time and then operated at a second speed for a second length of time. The protocols can be configured to correspond to the type of aspirate to be micronized. In some embodiments, the user inputs 172 are configured to allow an operator to select a desired protocol.

The control box 170 also includes various connectors 176. For example, the control box 170 can include connectors 176 configured to connect to the handpiece cable 107 and the pedal cable 109. In some embodiments, the control box can also include a power connector, allowing the control box 170 to be connected to a power source. In some embodiments, the power source can be an electrical outlet. In some embodiments, the control box 170 can include a battery. Thus, in some embodiments, the system 100 does not require connection to an external power source for operation. In some embodiments, the battery can be rechargeable, and the connectors 176 can include a charging port for charging the battery. Other connectors 176 can also be included on the control box 170. For example, the control box can include connectors 176 for interfacing with a computer, network, external display, or external input device (for example, a keyboard).

In some embodiments, the control box 170 is configured as a tabletop housing. In these embodiments, the control box 170 can be configured to connect to the handpiece 110 through the handpiece cable 107. In some embodiments, the control box 170 can be integrated into the handpiece 110. For example, in some embodiments, one or more of the components described above with regard to the control box 170, such as the motor controller 181, can be included within the handle 112.

As noted previously, the system 100 can include a pedal 190. The pedal 190 is connected to the control box 170 by a pedal cable 109. In some embodiments, the pedal 190 is a foot-operated pedal. In some embodiments, the pedal cable 109 is sufficiently long that the pedal 190 can be placed on the floor when the control box 170 is placed on a table top or lab bench. The pedal 190 can allow an operator to provide operational inputs to the control box 170 with his or her feet. In some embodiments, the pedal 190 can be used to control rotation of the blade 140. For example, in some embodiments, the pedal 190 can be pressed to start rotation of the blade 140 and pressed again to stop rotation of the blade. In some embodiments, the blade 140 rotates only when the pedal 190 is depressed. In some embodiments, the pedal 190 can also be configured to control the operating speed of the blade 140. For example, the degree to which the pedal 190 is depressed can correspond to the operating speed of the blade 140. In some embodiments, the blade 140 operates at a faster speed when the pedal 190 is depressed to a greater degree and operates at a slower speed when the pedal 190 is depressed to a lesser degree. In some embodiments of the system 100, the pedal 100 can be omitted. In some embodiments, each time the pedal 190 is depressed the blade 140 operates at a faster or slower speed. That is, each press of the pedal 190 can speed up the blade 140 (until an upper limit is reached) or slow down the blade 140 (until the blade 140 is stopped). In some embodiments, if the system 100 is set on a continuous mode, the pedal 190 just turns the machine on and off In some embodiments, if the system 100 is set to incremental mode, the pedal 190 can be pressed partially to mitigate a fractional pace to the maximum.

The system 100 is useful for micronizing an aspirate, for example, for use in the preparation of a cosmeceutical. For example, in some embodiments, an aspirate may be drawn into the syringe barrel 150 of the syringe by withdrawing a plunger of the syringe. The plunger may then be removed from the syringe barrel 150, leaving the aspirate within the syringe barrel 150. The blade 140 of the handpiece 110 can be then inserted into the syringe barrel 150 through the open end of the syringe. The end cap 152, through which the drive shaft 130 extends, can then be used to seal the open end of the syringe. In some embodiments, an additional cap can be used to close the opposite end of the syringe barrel 150. The operator can then select desired operating parameters using the user inputs 172 of the control box 170. Holding the handle 112 of the handpiece, the operator can then use then begin micronization of the aspirate by depressing the pedal 190, causing the motor 120 to rotate the blade 140. In some embodiments, the operator holds the handle 112 in a first hand and the syringe barrel 150 in a second hand. In some embodiments, the operator can work the blade 140 back and forth through the syringe barrel 150 by adjusting the position of the position of the handle 112 relative to the syringe barrel 150. In other words, in some embodiments, the operator pushes the handle 112 toward the end cap 152 until the handle 112 is proximal to the end cap 152 and then pulls the handle 112 away from the end cap 152 until the blade 150 is proximal to the end cap 152. The operator can repeat this process until the aspirate is micronized. In some embodiments, the micronization is visualized to a level that allows the fat to enter a gel-like phase, where the collagen strands are dissolved and the fat can be added to the base as described elsewhere in the application. Generally, in some embodiments, there is no defined endpoint other than the aspirate is micronized until it has a smoother constituency and thus allowing it to be added to a base. In some embodiments, cell counters may be used to take a sample and do a cell count and then add the aspirate to the base for making the product. In some embodiments, once the aspirate is micronized, it is added to the base in a set aliquot, which can be done from the syringe barrel 150. The amount can vary depending on the product one wishes to make. For example, an eye product may be less than a face product, etc. In some embodiments, an operator (such as a physician) may elect to incubate the micronized aspirate to get some SVF expansion before they add the fat to the base for the products. In some embodiment, the aspirate is added to the base at a ratio of approximately 1 to 3. In some embodiments, the ratio is approximately 1 to 2. Other ratios are also possible. As one example, for a 30 ml product, it may be 20 cc base and 10 cc SVF micronized aspirate In some embodiments, a small amount of collagenase is added to the to the aspirate to further break the strands either before or after micronization.

Alternatively, micronizing can be performed with the device described herein, without the use of enzymes. Enzymes for breaking the collagen and fibrous connective tissue are known to those skilled in the art. Without being limiting, these enzymes can include collagenase and elastase, for example.

In some embodiments, the operator can adjust the speed of the blade 140 during the micronization process. In some embodiments, the operator adjusts the speed of the blade 140 by varying the level of depression of the pedal 190. In some embodiments, the operator adjusts the speed of the blade 140 using the user inputs 172. In some embodiments, the speed of the blade 140 can be adjusted while the blade 140 rotates. In some embodiments, the rotation of the blade 140 must be stopped before the speed of rotation can be adjusted. For example, the operator can depress the pedal 190 to cause the rotation of the blade 140 at a first speed. If a second speed is desired, the operator can depress the pedal 190 again (or stop depressing the pedal 190) to stop rotation of the blade 140. The operator can then specify a second rotational speed using the user inputs 172, and then depress the pedal 190 again, to cause rotation of the blade 140 at the second speed. In some embodiments, the operator varies the speed if the aspirate comprises visible strands or lack of homogeneity or some other condition that would necessitate further morselization or micronization of the aspirate.

In some embodiments, the system 100 takes between 15 seconds to 10 minutes to micronize the aspirate, although other durations (higher and lower) are possible. In some embodiments, the system 100 takes between 1 and 4 minutes, between 1 and 3 minutes, and in some embodiments, the system takes between 1 and 2 minutes. In some embodiments, the system 100 takes no longer than 10 minutes, no longer than 8 minutes, no longer than 6 minutes, no longer than 5 minutes, no longer than 4 minutes, no longer than 3 minutes, no longer than 2 minutes, or no longer than 1 minute to micronize the aspirate. In a preferred embodiment, the system 100 takes no longer than 4 minutes. Once micronization is complete, the blade 140 can be withdrawn from the syringe barrel 150 by uncoupling the end cap 152 from the syringe barrel 150. The aspirate can then be removed from the syringe barrel 150 and used in the preparation of a cosmeceutical as described in throughout this application. In some embodiments, the preparation of the cosmeceutical can include incubation of the SVF (or aspirate), which in some embodiments can take several hours.

FIG. 15 shows a perspective view of one embodiment of the system 100 of FIG. 14. As shown, the system 100 includes a handpiece 110, a control box 170, and a pedal 190.

As shown in FIGS. 2 and 3, the handpiece 110 includes a handle 112. In the illustrated embodiment, the handle 112 comprises a cylindrical barrel. A motor 120 (not visible) is disposed within the cylindrical barrel of the handle 112. In the illustrated embodiment, the outer surface of the handle 112 is textured. The texture may be configured to improve the grip of the handle 112. One end of the handle 112 is connected to a handpiece cable 107 by a connector 107*b*. The opposite end of the handpiece cable 107 is connected by a connector 107*a* to the control box 170. A drive shaft 130 extends from an opposite end of the handle 112. The drive shaft 130 extends through an end cap 152 and into a syringe barrel 150. A blade 140 is disposed within the syringe barrel 150. The drive shaft 130, end cap 152, and handle 112, are shown and described in greater detail below, with reference to FIGS. 4-5B.

As shown in FIG. 15, the system 100 includes the control box 170. The control box 170 is shown alone in FIG. 19. In the embodiment depicted in is FIGS. 2 and 6, the control box 170 includes a housing. In the illustrated embodiment, the housing of the control box 170 is shaped as a rectangular prism, although other shapes for the housing are possible. In the illustrated embodiment, the control box 170 is configured for tabletop use. The control box 170 includes a display 171. The control box 170 also includes user inputs 172. In the illustrated embodiment, the user inputs 172 include a level up button and a level down button. The control box 170 also includes a first connector 176*a*, configured to connect to a connector 107*a* of the handpiece cable 107, and a second connector 176*b* configured to connect to a connector 109*a* of pedal cable 109. In some embodiments, the control box 170 is made by BSL of Korea (an SVF systems manufacturer). As performed in some embodiments herein, the device allows morselization and the process of micronizing the fat which can be used for adding to a base in a cosmeceutical, in order to manufacture the live cosmeceutical.

Micronizing can be performed with the device described herein, without the use of enzymes. Enzymes for breaking the collagen and fibrous connective tissue are known to those skilled in the art. Without being limiting, these enzymes can include collagenase and elastase, for example. Micronizing without the enzyme eliminates a purification step from the product which can lead to loss of product. Furthermore, micronizing without the use of an enzyme can lead to a pure product for treatment without the disadvantage of introducing an enzyme to a subject in need.

As shown in FIG. 15, the system 100 includes a pedal 190. The pedal 190 is connected to the control box 170 by the pedal cable 109.

FIG. 17 shows embodiments of several of the components of the handpiece 110 in a disassembled state. As illustrated in FIG. 17, the handle 112 can be formed as a cylindrical barrel. Although not visible in FIG. 17, the motor 120 can be disposed within the cylindrical barrel of the handle 112. An output shaft 116 of the motor 120 extends through one end of the handle 112. The exposed end of the output shaft 116 can be configured to connect to the drive shaft 130. For example, in the illustrated embodiment, the exposed end of the output shaft 116 includes first and second prongs 116*a* separated by a gap 116*b*. The first and second prongs 116*a* and the gap 116*b* are configured to interface with the drive shaft as will be described below. The exposed end of the output shaft 116 is protected by a cylindrical flange 114 extending from the end of the handle 112. An internal surface 115 of the flange 114 is threaded. The handle 112 can also include a guard 113, as shown. The features of the handle 112 are also shown in FIGS. 18A and 18B. As shown in FIG. 18B, the opposite end of the handle 112 (opposite the output shaft 116), includes a connector 117 for connecting the handle 112 to the handpiece cable 107 is provided.

In the embodiment of FIG. 17, the drive shaft 130 comprises a two-piece construction. The drive shaft 130 includes an outer sheath 131 and an inner shaft 135. The outer sheath 131 is configured as a hollow cylindrical barrel. The outer diameter of the outer sheath 131 is configured to correspond to the diameter of an opening 154 in the end cap 152. As will be described below, the outer sheath 131 of the drive shaft 130 interfaces with the opening 154 of the end cap 152 and provides a seal. As shown in FIG. 17, one end 132 of the outer sheath 131 is externally threaded. The externally threaded end 132 of the outer sheath 131 is configured to engage with the threaded internal surface 115 of the flange 114 of the handle 112. The inner diameter of the hollow cylindrical barrel of the outer sheath 131 is sufficiently large such that the inner shaft 135 of the drive shaft 130 can be received therein. In some embodiments, the inner diameter of the hollow cylindrical barrel of the outer sheath 131 is sufficiently large such that the inner shaft 135 of the drive shaft 130 can be received therein without contacting the inner surface of the outer sheath 131. The outer sheath 131 can be manufactured from stainless steel, although other materials are possible.

In some embodiments, the components that contact the aspirate are sterile. For example, in some embodiments, these components are sterilized by heat and/or chemicals. In some embodiments, the components that contact the aspirate are consumables that can be disposed of after use. For example, the blade 140 and out sheath 131 can be consumables to be discarded after use. In some embodiments, the sterilization is complex. In some embodiments, the blade 140 (and/or other components) needs to be replaced after micronizing an aspirate. In some embodiments, the blade 140 and/or other components) is hard to clean and must be cleaned carefully. As noted above, in some embodiments, the blade 140 (and/or other components) can be made disposable with different variants of plastics or metals. The rod (e.g., the drive shaft 130) that connects to the motor 120 and the blade 140 itself is sheathed (e.g., by outer sheath 131). In some embodiments, it can be difficult to make the motor be heat sterilized, although it is possible. However the cables (e.g., handpiece cable 107) from the motor 120 to the control box 170 may not tolerate heat sterilization. In some embodiments, the whole system 100 can be chemically sterilized; however, in some preferred embodiments, the motor rod is sheathed and the blade is replaced as a consumable item.

In the embodiment of FIG. 17, the inner shaft 135 of the drive shaft 130 comprises a cylindrical rod extending between a first end 136 and a second end 137. The first end 136 of the drive shaft 130 is configured with features for engaging the external portion of the output shaft 116 of the motor 120. For example, as illustrated, the first end includes protrusions 136a. The protrusions 136a are configured to be received within the slot 116b between the prongs 116a of the output shaft 116. The prongs 116a engage the protrusions 136a to secure the inner shaft 135 to the output shaft 116 and to transfer rotational motion from the motor 120 to the inner shaft 135. The second end 137 of the inner shaft 135 is connected to the blade 140.

In the illustrated embodiment, the blade 140 comprises two prongs, although other configurations for the blade, including a single prong, three prongs, or other configurations are possible. In some embodiments, the prongs of the blade 140 are sharpened. In some embodiments, the prongs of the blade 140 are dull or blunt. In some embodiments, a leading edge of the prongs of the blade 140 is sharpened and a trailing edge of the prongs of the blade 140 is dull or blunt. The blade 140 is rigidly attached to the second end 137 of the input shaft 135 such that the blade 140 rotates with rotation of the inner shaft 135.

In the illustrated embodiment, a blade guard 141 is also attached to the second end 137 of the inner shaft 135. In some embodiments, the blade guard 141 can be rigidly attached to the inner shaft 135 so that the two rotate together, or, in some embodiments, the blade guard 141 fits loosely over the inner shaft 135 such that rotation of the inner shaft 135 does not cause rotation of the blade guard 141. The blade guard 141 can be configured to prevent the blade 140 from contacting the walls of the syringe barrel 150. The blade guard 141 can be configured to substantially center the blade guard within the syringe barrel 150. In some embodiments, the blade guard 141 comprises a cylindrical shape with a diameter that is slightly less than (for example, between 85% and 99% of) the inner diameter of the syringe barrel 150. In the illustrated embodiment, the blade guard 141 includes an alternating pattern of projections 143 separated by cutouts 144. In the illustrated embodiment, the blade guard 141 includes six projections 143 separated by six cutouts 144, although other numbers are possible. The blade 140 is configured to rotate within a hollow space formed in the interior of the blade guard 141. The blade 140 is surrounded by the projections 143 and cutouts 144. The inner shaft 135 blade 140, and blade guard 141 can each be manufactured from stainless steel, although other materials are possible.

FIG. 17 also illustrates an embodiment of the end cap 152. As shown, the end cap 152 includes the opening 154 described above. The opening 154 is configured to interface with the outer surface of the outer sheath 131 in a manner that provides a seal. In some embodiments, the opening 154 provides a seal, while still allowing the outer sheath 131 to slide forward and backward through the opening 154. In some embodiments, one or more O-rings are provided within the opening 154 to provide the seal between the opening 154 and the outer sheath 131. The end cap 152 also includes a lower flange 153 that interfaces and seals against an opening of the syringe barrel 150. The lower flange 153 may be configured in size and shape to correspond to the shape of the syringe barrel 150. In some embodiments, the lower flange 153 includes one or more O-rings for providing a seal between the end cap 152 and the syringe barrel 150. In the illustrated embodiment, the end cap 152 also includes two wings 155 configured with lips that secure the end cap 152 to the syringe barrel. In some embodiments, the end cap 152 is manufactured from rubber, plastic, or other suitable materials.

In some embodiments, the handpiece 110 is assembled for use from the components illustrated in FIG. 17. For example, the threaded end 132 of the outer sheath 131 can be threaded into the flange 114 of the handle 112. The end cap 152 can then be inserted onto the outer sheath 131, such that the outer sheath 131 is disposed within the opening 154. The lower flange 153 faces away from the handle 112. The first end 136 of the inner shaft 135 can then be inserted through the open end of the outer sheath 135 until it engages with the output shaft 116. A syringe barrel 150 containing the aspirate to be micronized can then be connected to the end cap 152, such that the blade 140 is positioned within the syringe barrel 150. The order of these steps is provided by way of example and may be varied.

In some embodiments, the inner shaft 135 of the drive shaft 130 rotates within the outer sheath 131, while the outer sheath 135 remains stationary.

The assembled handpiece 110 can then be connected to the control box 170 and used to micronize the aspirate as described above.

Those of ordinary skill in the art will, upon consideration of this disclosure understand that various modifications to the embodiments described herein are possible. The embodiments provided above are given by way of example only and are not intended to be limiting.

Amnion Cells from Cord Blood to Cultured Cells in HPL to Product.

In some embodiments, expanded amnion cells grown in media that is supplemented with HPL is provided. The cells grown in the supplemented media can be banked for future product development.

Marrow Aspirate Cultured in HPL and Expanded to Product.

In some embodiments, expanded cells grown in media that is supplemented with HPL is provided. The cells can originate from a marrow isolate banked for future product development. The marrow isolate originates from the subject to be treated.

PRP to Live Point of Care Cosmetic.

In some embodiments, megakaryocytes are collected from a subject desiring live point of care cosmetics. The megakaryocytes are expanded in media supplemented with HPL and as such, the PRP can be made into products in perpetuity.

In some embodiments, PTAC (personal treatment and care) provided to the subject in need, is a point of care cosmeceutical. The cosmeceutical can comprise cells that were developed for topical treatment of a subject in need. In some embodiments, the cell is selected from an aspirate, a marrow aspirate, fat aspirate, bone marrow aspirate, dental tissue and/or amnio/placental tissue. In some embodiments, the cell is provided in a formulation. The formulation can be topical formulation or a formulation for injection. In some embodiments, the formulation comprises platelet rich plasma (PRP). PRP, is a blood plasma that has been enriched with platelets, and aside from being a nutrient for the call, can be used to speed up and improve or enhance heeling of a subject in need. In some embodiments, the methods of the present application may be performed in part using one or more of a micronizer, tissue separator or tissue homogenizer. In some embodiments, the formulations described herein may be formed from the methods described in the present application. In some embodiments, one or more of a micronizer, tissue separator or tissue homogenizer may be used to make live pharmaceuticals from bone marrow. As such, a formulation comprising the PRP can be used to enhance healing of a wound, for example.

In some embodiments of the methods described herein, tissue or aspirate is micronized. The tissue or aspirate as described herein can be micronized by any one of the embodiments of the devices described herein. In some embodiments, the micronizer includes the systems and devices shown and described with reference to FIGS. 14-19. Without being limiting, the tissue and/or aspirate can also be micronized into small particles by several types of tissue homogenizers or tissue separators, which can include, for example, modular homogenizers, digital high-speed homogenizer, commercial tissue grinder, commercial tissue pulverizer, a tissue tearor variable speed homogenizer, ultrasonic tissue homogenizers and a batch process homogenizer. These types of homogenizers are also commercially available and are known to those skilled in the art. (i.e. Sigma Aldridge, Cole-Parmer, Thomas Scientific, Hielscher). Protocols for the homogenization of tissue and aspirate can be appreciated by those of skill in the art.

In some embodiments of the formulations described herein, the formulations can further comprise micronized tissue or fat for use in a formulation that is for topical application or as an injectable. In some embodiments, the formulation comprises tissue or fat that has been micronized by a commercially available tissue separator or a device for homogenization of tissue. The tissue or aspirate as described herein can be micronized by any one of the embodiments of the devices described herein. In some embodiments, the micronizer includes the systems and devices shown and described with reference to FIGS. 14-19. Without being limiting, the tissue and/or aspirate can be micronized into small particles by several types of tissue homogenizers or tissue separator, which can include modular homogenizers, digital high-speed homogenizer, commercial tissue grinder, commercial tissue pulverizer, a tissue tearor variable speed homogenizer, ultrasonic tissue homogenizers and a batch process homogenizer. The micronized tissue or aspirate can be used in the formulation as a dermal filler, for example.

"Tissue separator" or "homogenizer" as described herein, is a device for bringing a biological sample, such as a tissue or aspirate, into substantially equal or uniform composition in a sample.

"Platelet poor plasma" is a blood plasma with a very low number of platelets (less than $10 \times 10^3$ platelets/µL). However platelet poor plasma can have elevated levels of fibrinogen, which can have the ability to form a fibrin rich clot when activated. In some embodiments, PTAC (personal treatment and care) provided to the subject in need, is a point of care cosmeceutical. The cosmeceutical can comprise cells that were developed for topical treatment of a subject in need. In some embodiments, the cell is selected from an aspirate, a marrow aspirate, fat aspirate, bone marrow aspirate, dental tissue and/or amnio/placental tissue. In some embodiments, the cell is provided in a formulation. The formulation can be topical formulation or a formulation for injection. In some embodiments, the formulation further comprises platelet-poor plasma (PPP). Platelet poor plasma can be added to the formulation, if the subject is in need of fibrinogen.

"Platelet rich fibrin matrix," or (PRFM) as described herein, is PRP supplemented with calcium chloride. PRFM is marketed in the United States as Selphyl, TruPRP, Emcyte, Regen and Pure Spin. The method of making PRFM involves drawing blood from a subject in need and centrifuging the blood to separate out the platelets. The platelets can then be injected back into the skin as use as a dermal filler. Platelet rich fibrin matrix has been reported to stimulate bone and soft tissue growth for fast healing. Furthermore, the platelet rich fibrin matrix is known to promote wound healing and sealing, bone growth and graft stabilization. Platelet rich fibrin matrix can also be used for soft tissue regeneration. As it is from the subject in need, there is also no risk of the possibility of rejection.

In some embodiments, PTAC (personal treatment and care) provided to the subject in need, is a point of care cosmeceutical. The cosmeceutical can comprise cells that were developed for topical treatment of a subject in need. In some embodiments, the cell is selected from an aspirate, a marrow aspirate, fat aspirate, bone marrow aspirate, dental tissue and/or amnio/placental tissue. In some embodiments, the cell is provided in a formulation. In some embodiments, The formulation can be topical formulation or a formulation for injection. In some embodiments, the formulation can further comprise platelets from the subject in need. In some embodiments, the formulation comprises platelet-rich fibrin matrix (PFRM) from the subject in need. The PRFM can be manufactured from blood of the patient in need. In some embodiments, blood is obtained from a patient in need. The blood is then centrifuged at high speeds to separate out the platelets. In some embodiments, the centrifugation is performed twice. In some embodiments, the centrifugation is performed 2, 3, 4, 5 or more times. The platelets are then combined with the formulation. In some embodiments, the subject in need has wrinkles. In some embodiments, the subject suffers from dry or cracked skin. In some embodiment, the subject is in need of tissue heeling. In some embodiments, the tissue is skin tissue. In some embodiments, the skin issue is on the scalp. In some embodiments, the skin tissue is on the face. In some embodiments, the tissue is gum tissue. In some embodiments, the formulation is used for a subject who has just received oral surgery, such as periodontal surgery.

More Embodiments

A method of making a cell for treatment of a subject in need is provided. The method can include, for example, obtaining cells from the subject, placing cells in growth media, wherein the growth media includes human platelet lysate or human serum and growing the cells up to confluency. In some embodiments, obtaining cells from the subject comprises obtaining at least one of skin cells, fibroblasts, mesenchymal stem cells, stem cells and primary human cells. In some embodiments, obtaining cells from the subject comprises obtaining at least one of an aspirate, a marrow aspirate, fat aspirate or amnio/placental tissue. In some embodiments, the cell is selected from an aspirate, a marrow aspirate, fat aspirate, bone marrow aspirate, dental tissue and/or amnio/placental tissue. In some embodiments, the method further comprises micronizing the aspirate or amnio/placental tissue. In some embodiments, obtaining cells from the subject comprises obtaining cells from a kidney extract or a liver extract. In some embodiments, the aspirate or amnio/placental tissue is micronized. In some embodiments, the micronization includes the use of the systems and devices shown and described with reference to FIGS. 14-19. In some embodiments, the method further comprises micronizing the kidney extract or the liver extract. In some embodiments, the growth media includes human platelet lysate. In some embodiments, the growth media further comprises human serum or fibroblast differentiation media. In some embodiments, after growing the cells up to confluency, the method further comprises concentrating the cells. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the cell is from an aspirate, a marrow aspirate, fat aspirate and/or amnio/placenta. In some embodiments, the cell is selected from an organ extract. A flow diagram exemplifying the method of making a cell for treatment of a subject is shown in FIG. 20.

In some embodiments, a cell is provided. The cell can be manufactured by a method of any one of the described embodiments herein. The method can include, for example, obtaining cells from the subject, placing cells in growth media, wherein the growth media includes human platelet lysate or human serum and growing the cells up to confluency. In some embodiments, obtaining cells from the subject comprises obtaining at least one of skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, obtaining cells from the subject comprises obtaining at least one of an aspirate, a marrow aspirate, fat aspirate or amnio/placental tissue. In some embodiments, the method further comprises micronizing the aspirate or amnio/placental tissue. In some embodiments, obtaining cells from the subject comprises obtaining cells from a kidney extract or a liver extract. In some embodiments, the aspirate or amnio/placental tissue is micronized. In some embodiments, the micronization includes the use of the systems and devices shown and described with reference to FIGS. 14-19. In some embodiments, the method further comprises micronizing the kidney extract or the liver extract. In some embodiments, the growth media includes human platelet lysate. In some embodiments, the growth media further comprises human serum or fibroblast differentiation media. In some embodiments, after growing the cells up to confluency, the method further comprises concentrating the cells. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the cell is from an aspirate, a marrow aspirate, fat aspirate and/or amnio/placenta. In some embodiments, the cell is selected from an organ extract. In some embodiments, the micronizing is performed without an enzyme. In some embodiments, the enzyme is collagenase or elastase.

In some embodiments, a topical formulation is provided. The topical formulation can include, for example, the cells made by the methods of any of the embodiments described herein or the cell of any of the embodiments described herein and a pharmaceutical vehicle. The cell can be manufactured by a method of any of the described embodiments herein. The method can include, for example, obtaining cells from the subject, placing cells in growth media, wherein the growth media includes human platelet lysate or human serum and growing the cells up to confluency. In some embodiments, obtaining cells from the subject comprises obtaining at least one of skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, obtaining cells from the subject comprises obtaining at least one of an aspirate, a marrow aspirate, fat aspirate or amnio/placental tissue. In some embodiments, the method further comprises micronizing the aspirate or amnio/placental tissue. In some embodiments, obtaining cells from the subject comprises obtaining cells from a kidney extract or a liver extract. In some embodiments, the aspirate or amnio/placental tissue is micronized. In some embodiments, the micronization includes the use of the systems and devices shown and described with reference to FIGS. 14-19. In some embodiments, the method further comprises micronizing the kidney extract or the liver extract. In some embodiments, the growth media includes human platelet lysate. In some embodiments, the growth media further comprises human serum or fibroblast differentiation media. In some embodiments, after growing the cells up to confluency, the method further comprises concentrating the cells. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the cell is from an aspirate, a marrow aspirate, fat aspirate and/or amnio/placenta. In some embodiments, the cell is selected from an organ extract. In some embodiments, the micronizing is performed without an enzyme. In some embodiments, the enzyme is collagenase or elastase.

In some embodiments, a formulation for injection is provided. The formulation can have the cells made by the methods of any one of the embodiments described herein or the cell of any one or more of the embodiments described herein and an excipient. The method can include, for example, obtaining cells from the subject, placing cells in growth media, wherein the growth media includes human platelet lysate or human serum and growing the cells up to confluency. In some embodiments, obtaining cells from the subject comprises obtaining at least one of skin cells, fibroblasts, mesenchymal stem cells, stem cells and primary human cells. In some embodiments, the cell is selected from an aspirate, a marrow aspirate, fat aspirate, bone marrow aspirate, dental tissue and/or amnio/placental tissue. In some embodiments, obtaining cells from the subject comprises obtaining at least one of an aspirate, a marrow aspirate, fat aspirate or amnio/placental tissue. In some embodiments, the method further comprises micronizing the aspirate or amnio/placental tissue. In some embodiments, obtaining cells from the subject comprises obtaining cells from a kidney extract or a liver extract. In some embodiments, the aspirate or amnio/placental tissue is micronized. In some embodiments, the micronization includes the use of the systems and devices shown and described with reference to FIGS. 14-19. In some embodiments, the method further comprises micronizing the kidney extract or the liver extract. In some embodiments, the growth media includes human platelet lysate. In some embodiments, the growth media further comprises human serum or fibroblast differentiation media. In some embodiments, after growing the cells up to confluency, the method further comprises concentrating the cells. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the method further includes passaging the cells 1, 2, 3, 4 or 5 times. In some embodiments, the method further includes concentrating the cells. In some embodiments, the method further includes cryo-freezing the cells for storage. In some embodiments, the cell is a skin cell, fibroblast, mesenchymal stem cell, stem cell or primary human cell. In some embodiments, the cell is from an aspirate, a marrow aspirate, fat aspirate and/or amnio/placenta. In some embodiments, the cell is selected from an organ extract. In some embodiments, the cell is from fat aspirate. In some embodiments, the formulation further comprises a pharmaceutical vehicle. In some embodiments, the micronizing is performed without an enzyme. In some embodiments, the enzyme is collagenase or elastase.

In some embodiments, a method of treating a subject suffering from a skin disorder is provided. The method can include, for example, obtaining cells from the subject, placing cells in growth media, wherein the growth media comprises human platelet lysate or human serum, growing the cells up to confluency, providing the cells to the subject alone or in a topical formulation to the subject and applying the cell or topical formulation to the subject, wherein the cell or topical formulation is applied onto skin. In some embodiments, the cell or topical formulation is applied onto skin. The cell can be manufactured by a method of any of the embodiments described herein. The method can include obtaining cells from the subject, placing cells in growth media, wherein the growth media includes human platelet lysate or human serum and growing the cells up to confluency. In some embodiments, the cell is selected from a group consisting of skin cells, fibroblasts, mesenchymal stem cells, stem cells and primary human cells. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media comprises human platelet lysate. In some embodiments, the growth media includes human serum. In some embodiments, the growth media includes fibroblast differentiation media. In some embodiments, the skin disorder is selected from a group consisting of psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, and impetigo. In some embodiments, the applying is performed 1, 2, 3 or 4 times a day. In some embodiments, the applying is performed one or more times a day for 1 day, 3 days, 7 days, 14 days, 21 days or 28 days or any number of days in between any two aforementioned numbers of days, for example, 1, 2, 3, 4, 5, 6, 7, 8, 9, 10, 11, 12, 13, 14, 15, 16, 17, 18, 19, 20, 21, 22, 23, 24, 25, 26, 27, or 28 days. A flow diagram exemplifying the method of treating a subject suffering from a skin disorder is shown in FIG. 21.

In some embodiments, a method of treating a subject suffering from pain is provided, the method can include, for example, obtaining cells from the subject, placing cells in growth media, wherein the growth media comprises human platelet lysate or human serum, growing the cells up to confluency, providing the cells to the subject alone or in a topical formulation to the subject and applying the cell or topical formulation to the subject, wherein the cell or topical formulation is applied onto skin. The cell can be manufactured by a method of any of the described embodiments herein. The method can include obtaining cells from the subject, placing cells in growth media, wherein the growth media includes human platelet lysate or human serum and growing the cells up to confluency. In some embodiments, the cell is selected from a group consisting of skin cells, fibroblasts, mesenchymal stem cells, stem cells and primary human cells. In some embodiments, the growth media includes human platelet lysate. In some embodiments, the growth media includes human serum. In some embodiments, the growth media includes fibroblast differentiation media. In some embodiments, the cells are grown for 2, 3, 4, 5, 6, 7, 8, 9 or 10 hours, or any time between any two aforementioned values. In some embodiments, the cells are grown to 40%, 50%, 60%, 70%, 80% or 90%, confluency. In some embodiments, the cell is a skin cell, fibroblast, mesenchymal stem cell, stem cell or primary human cell. In some embodiments, the topical formulation further includes a nutrient for the cell. In some embodiments, the topical formulation further includes growth media. In some embodiments, the growth media includes human platelet lysate. In some embodiments, the growth media includes human serum. In some embodiments, the growth media includes fibroblast differentiation media. In some embodiments, the pain is from arthritis. In some embodiments, the pain is from a disease. In some embodiments, the applying is performed 1, 2, 3 or 4 times a day. In some embodiments, the applying is performed for 1 day, 3 days, 7 days, 14 days, 21 days or 28 days or any number of days in between any two aforementioned numbers of days. A flow diagram exemplifying the method of treating a subject suffering from pain is shown in FIG. 21.

In some embodiments, a method of treating skin is provided. The method can include injecting of the formulation of any one of the embodiments herein, such as into a facial region or neck region. In some embodiments, the method can include obtaining cells from the subject, placing the cells in growth media, wherein the growth media comprises human platelet lysate or human serum, growing the cells up to confluency, providing the cells in an injectable formulation to the subject and injecting the formulation into a facial region or neck region of the subject. In some embodiments, the method comprises obtaining cells from the subject, placing the cells in growth media, wherein the growth media comprises human platelet lysate or human serum, growing the cells up to confluency, providing the cells in an injectable formulation to the subject and injecting the formulation into a facial region or neck region of the subject. In some embodiments, the applying is performed once every 3, 6 or 12 months or any range of time in between any two aforementioned number of months. In some embodiments, a formulation for injection is provided, wherein the formulation comprises cells and a pharmaceutical vehicle. In some embodiments, the cells can be micronized for injection into a specific site for a patient in need as a personalized medicine or personalized treatment. In some embodiments, the micronization includes the use of the systems and devices shown and described with reference to FIGS. 14-19. In some embodiments, the injectable formulation can be prepared in conventional forms, either as liquid solutions or suspensions, solid forms suitable for solution or suspension in liquid prior to injection, or as emulsions. The fat aspirate containing the cells for injection can be micronized for injection so that the fat can be emulsified in order to help inject it into small areas such as the face and neck. In some embodiments, the micronization includes the use of the systems and devices shown and described with reference to FIGS. 14-19. Without being limiting, this can be used, for example with fat from a liposuction technique from a patient and then used again on the same patient for a live personalized cosmeceutical. Micronizing can also be performed with platelet rich plasma. In some embodiments, the subject has wrinkles and/or saggy skin. In some embodiments, the subject has tear troughs and/or fat loss in facial and neck regions. In some embodiments, the injecting comprises injecting the formulation into a tear trough or a wrinkle. In some embodiments, the micronizing is performed without an enzyme. In some embodiments, the enzyme is collagenase or elastase. A flow diagram exemplifying the method of treating skin of a subject is shown in FIG. 22.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

What is claimed is:

1. A method of diminishing pore size, red areas or porphyrins on a subject's skin, the method consisting of:
applying a topical formulation to the skin of the subject to improve the pore size, the red areas or the porphyrins on the skin of the subject, the topical formulation consisting of a pharmaceutical vehicle combined with dermal fibroblasts obtained from the subject and grown in a growth medium consisting of minimum essential medium (MEM) and 5% to 10% v/v human platelet lysate.

2. A method of diminishing pore size, red areas, bacteria damage or porphyrins in a subject, the method consisting of:
obtaining dermal fibroblasts from the skin of the subject;
growing the dermal fibroblasts in a growth medium consisting of a culture medium and 5% to 10% v/v human platelet lysate;
combining the grown dermal fibroblasts and a pharmaceutical vehicle to form a topical formulation; and
providing the topical formulation to the subject to treat the skin condition,
wherein the culture medium is selected from the group consisting of alpha-minimum essential medium (MEM), Dulbecco's Modified Eagle's Medium (DMEM) and DMEM/F-12.

3. The method of claim 2, wherein the culture medium is alpha-minimum essential medium (MEM).

4. The method of claim 2, wherein the culture medium is Dulbecco's Modified Eagle's Medium (DMEM).

5. The method of claim 2, wherein the culture medium is DMEM/F-12.

6. The method of claim 2, wherein the human platelet lysate is 10% good manufacturing practice (GMP) human platelet lysate.

7. The method of claim 1, wherein the subject is female, and wherein applying the topical formulation diminishes pore size, or diminishes bacteria damage.

8. The method of claim 7, wherein the applying the topical formulation comprises applying 5 ml of the topical formulation.

9. The method of claim 7, wherein the applying the topical formulation comprises spreading the topical formulation on the forehead, undereye area, cheeks, nose or chin.

10. The method of claim 7, wherein the applying is performed twice per day for twenty days.

11. The method of claim 1, wherein the subject is male and wherein applying the topical formulation diminishes pore size, or diminishes red areas.

12. The method of claim 11, wherein the applying the topical formulation comprises applying 5 ml of the topical formulation.

13. The method of claim 11, wherein the applying the topical formulation comprises spreading the topical formulation on the forehead, undereye area, cheeks, nose or chin.

14. The method of claim 11, wherein the applying is performed twice per day for twenty days.

15. A method of diminishing pore size, bacteria damage, or red areas in a subject, the method consisting of:
applying to the skin of the subject suffering from enlarged pore size, bacteria damage, or red areas a topical formulation consisting of dermal fibroblasts grown in a growth medium consisting of minimum essential medium (MEM) supplemented with 10% human platelet lysate,
wherein the applying the topical formulation comprises spreading the topical formulation on the forehead, undereye area, cheeks, nose or chin, and
wherein the applying is performed twice per day for twenty days.

16. The method of claim 15, wherein the spreading the topical formulation comprises spreading 5 ml of the topical formulation.

17. The method of claim 1, wherein the human platelet lysate is 10% good manufacturing practice (GMP) human platelet lysate.

18. The method of claim 15, wherein the human platelet lysate is 10% good manufacturing practice (GMP) human platelet lysate.

* * * * *

UNITED STATES PATENT AND TRADEMARK OFFICE
CERTIFICATE OF CORRECTION

PATENT NO. : 10,420,802 B2
APPLICATION NO. : 15/373325
DATED : September 24, 2019
INVENTOR(S) : Farhan Taghizadeh It is certified that error appears in the above-identified patent and that said Letters Patent is hereby corrected as shown below:

In the Drawings

In Drawing sheet 7 of 24, FIG. 7, Y Axis, Line 1, "Ploliferation" should read --Proliferation--.

In the Specification

Column 1, Line 35, "Juvaderm®," should read --Juvederm®,--.

Column 8, Line 47, "Macopharama" should read --Macopharma--.

Column 11, Line 5, "keloidis" should read --keloidalis--.

Column 11, Line 41, "keloidis" should read --keloidalis--.

Column 12, Line 36, "onchyocryptosis," should read --onychocryptosis,--.

Column 12, Line 36, "onychogryposis," should read --onychogryphosis,--.

Column 12, Line 37, "onchorrhexis," should read --onychorrhexis,--.

Column 12, Line 48, "onchyocryptosis," should read --onychocryptosis,--.

Column 12, Line 49, "onychogryposis," should read --onychogryphosis,--.

Column 12, Line 51, "onchorrhexis," should read --onychorrhexis,--.

Column 12, Line 64, "karatoacanthoma," should read --keratoacanthoma,--.

Column 13, Line 11, "karatoacanthoma," should read --keratoacanthoma,--.

Signed and Sealed this
Twenty-fourth Day of December, 2019

Andrei Iancu
*Director of the United States Patent and Trademark Office*

CERTIFICATE OF CORRECTION (continued)
U.S. Pat. No. 10,420,802 B2

Column 14, Line 41, "Minimimal" should read --Minimal--.

Column 14, Line 44, "Optimim," should read --Optimum,--.

Column 14, Line 46, "(AciCHO P)." should read --(ActiCHO P).--.

Column 15, Lines 43-44, "(J Vis Exp. 2009 Oct 30 ;(32)," should read --(J Vis Exp. 2009 Oct 30; (32)),--.

Column 17, Line 46, "seborrheoeic" should read --seborrheic--.

Column 17, Line 48, "Hidradentitis" should read --Hidradenitis--.

Column 17, Line 52, "pedifulosis," should read --pediculosis,--.

Column 17, Line 63, "keloidis" should read --keloidalis--.

Column 21, Line 56 approx., "pnenoxytthanol," should read --phenoxyethanol,--.

Column 21, Line 59 approx., "pnenoxytthanol," should read --phenoxyethanol,--.

Column 23, Line 7, "paronchia," should read --paronychia,--.

Column 23, Line 39, "keloidis" should read --keloidalis--.

Column 26, Lines 14-15, "mesencolhymal" should read --mesenchymal--.

Column 34, Line 27, "(13 days after the biopsy" should read --(13 days after the biopsy)--.

Column 35, Line 42, "(for" should read --for--.

Column 42, Line 37, "(for" should read --for--.

Column 46, Line 57, "and/or" should read --(and/or--.

Column 47, Line 50, "135" should read --135,--.